(12) United States Patent
Hinkle

(10) Patent No.: US 10,745,702 B2
(45) Date of Patent: Aug. 18, 2020

(54) COMPOSITIONS AND METHODS FOR INHIBITING EXPRESSION OF THE LECT2 GENE

(71) Applicant: ALNYLAM PHARMACEUTICALS, INC., Cambridge, MA (US)

(72) Inventor: Gregory Hinkle, Plymouth, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/564,288

(22) PCT Filed: Apr. 8, 2016

(86) PCT No.: PCT/US2016/026676
§ 371 (c)(1),
(2) Date: Oct. 4, 2017

(87) PCT Pub. No.: WO2016/164746
PCT Pub. Date: Oct. 13, 2016

(65) Prior Publication Data
US 2018/0135057 A1 May 17, 2018

Related U.S. Application Data

(60) Provisional application No. 62/144,695, filed on Apr. 8, 2015.

(51) Int. Cl.
| | | |
|---|---|---|
| *C07H 21/04* | (2006.01) | |
| *C12N 15/113* | (2010.01) | |
| *A61P 25/28* | (2006.01) | |
| *A61P 17/00* | (2006.01) | |
| *A61K 31/712* | (2006.01) | |
| *A61K 31/7125* | (2006.01) | |
| *A61K 47/26* | (2006.01) | |
| *A61P 1/16* | (2006.01) | |

(52) U.S. Cl.
CPC ........ *C12N 15/1136* (2013.01); *A61K 31/712* (2013.01); *A61K 31/7125* (2013.01); *A61K 47/26* (2013.01); *A61P 17/00* (2018.01); *A61P 25/28* (2018.01); *A61P 1/16* (2018.01); *C12N 2310/11* (2013.01); *C12N 2310/315* (2013.01); *C12N 2310/321* (2013.01); *C12N 2310/322* (2013.01); *C12N 2310/335* (2013.01); *C12N 2310/351* (2013.01); *C12N 2310/3521* (2013.01); *C12N 2310/3533* (2013.01)

(58) Field of Classification Search
None
See application file for complete search history.

(56) References Cited

U.S. PATENT DOCUMENTS

| | | | |
|---|---|---|---|
| 7,399,852 B2* | 7/2008 | Becker | C07H 21/00 435/6.1 |
| 8,106,022 B2 | 1/2012 | Manoharan et al. | |
| 10,077,444 B2 | 9/2018 | Fitzgerald et al. | |
| 2002/0086356 A1 | 7/2002 | Tuschl et al. | |
| 2005/0246794 A1 | 11/2005 | Khvorova et al. | |
| 2005/0255487 A1 | 11/2005 | Khvorova et al. | |
| 2009/0281167 A1 | 11/2009 | Shen et al. | |
| 2010/0120893 A1 | 5/2010 | Sah et al. | |
| 2010/0322928 A1* | 12/2010 | Mozes | G01N 33/564 424/134.1 |
| 2011/0287424 A1* | 11/2011 | Chen | C12Q 1/6851 435/6.11 |
| 2012/0225927 A1 | 9/2012 | Sah et al. | |
| 2013/0330717 A1 | 12/2013 | Dovzhenko et al. | |
| 2014/0343123 A1 | 11/2014 | Prakash et al. | |
| 2016/0264966 A1 | 9/2016 | Fitzgerald et al. | |
| 2018/0135057 A1 | 5/2018 | Hinkle | |
| 2019/0119674 A1 | 4/2019 | Bettencourt et al. | |

FOREIGN PATENT DOCUMENTS

| | | |
|---|---|---|
| CN | 102552882 A | 7/2012 |
| WO | 2010006342 A2 | 1/2010 |
| WO | 2011076095 A1 | 6/2011 |
| WO | 2012009567 A2 | 1/2012 |
| WO | 2012135246 A2 | 10/2012 |
| WO | 2013075035 A1 | 5/2013 |
| WO | 2015050990 A1 | 4/2015 |
| WO | 2016164746 A1 | 10/2016 |
| WO | 2020037125 A1 | 2/2020 |

OTHER PUBLICATIONS

Vickers et al. (J. Biol Chem 278; 7108-7118 2003).*
Damlaj, Moussab, et al. ("Hepatic ALECT-2 amyloidosis causing portal hypertension and recurrent variceal bleeding: a case report and review of the literature." American journal of clinical pathology 141.2 (2014): 288-291).*
L'hermitte, Antoine, et al. "Lect2 Controls Inflammatory Monocytes to Constrain the Growth and Progression of Hepatocellular Carcinoma." Hepatology 69.1 (2019): 160-178.*
"Poster Session 4: HCV: Virology, Pathogenesis, and Immunology" Hepatology (2014) vol. 60, pp. 1048A-1087A.
Benson et al., "Leukocyte Chemotactic Factor 2: A Novel Renal Amyloid Protein", Kidney International, vol. 74, No. 2, Apr. 30, 2008, pp. 218-222.
Benson, Merrill D., "LECT2 Amyloidosis", Kidney International, vol. 77, No. 9, May 1, 2010, pp. 757-759.
International Search Report and Written Opinion for International Application No. PCT/US2016/026676 dated Jul. 12, 2016.
International Search Report and Written Opinion in International Application No. PCT/US2014/058624 dated Jan. 13, 2015.

(Continued)

*Primary Examiner* — Kimberly Chong
(74) *Attorney, Agent, or Firm* — Lando & Anastasi, LLP

(57) ABSTRACT

The invention relates to antisense polynucleotide agents targeting the LECT2 gene, and methods of using such antisense polynucleotide agents to inhibit expression of LECT2 and to treat subjects having a LECT2-associated disease, e.g., amyloidosis.

28 Claims, No Drawings
Specification includes a Sequence Listing.

(56) References Cited

OTHER PUBLICATIONS

Larsen et al., "Prevalence and Morphology of Leukocyte Chemotactic Factor 2-Associated Amyloid in Renal Biopsies", Kidney International, vol. 77, No. 9, Feb. 24, 2010, pp. 816-819.
Wu et al. "The Roles of Leukocyte Cell-Derived Chemotaxin 2 Gene in Hepatocellular Carcinoma Invasion and Angiogenesis" Proceedings of the American Association for Cancer Research Annual Meeting (2008) pp. 1-35.
Yamagoe et al., "Molecular Cloning of Human and Bovine LECT2 Having a Neutrophil Chemotactic Activity and Its Specific Expression in the Live", Biochimica Et Biophysica Acta, Elsevier, NL, vol. 1396, No. 1, Mar. 4, 1998, pp. 105-113.
Chen et al. "Leukocyte cell-derived chemotaxin 2 antagonizes MET receptor activation to suppress hepatocellular carcinoma vascular invasion by protein tyrosine phosphatase 1B recruitment" Hepatology (2014) vol. 59, No. 3, pp. 974-985.
International Search Report and Written Opinion for International Application No. PCT/US2019/046657 dated Jan. 23, 2020.
Zhu et al. "Dicer partner protein tunes the length of miRNAs using base-mismatch in the pre-miRNA stem" Nucleic Acids Research (2018) vol. 46, No. 7, pp. 3726-3741.

\* cited by examiner

SEQUENCE LISTING

<160> NUMBER OF SEQ ID NOS: 300

<210> SEQ ID NO 1
<211> LENGTH: 1077
<212> TYPE: DNA
<213> ORGANISM: Homo sapiens

<400> SEQUENCE: 1

```
aaatcaaata gctatccatg gaatattaga acttgacttg ctccatcctc ttaaactttt    60
tgtgtctcac actaaagaaa tgagagatgc agaattctaa ggctaaatag ctaggaagta   120
ttcattcaaa cttgaatatt cttcaaagag agtgtggggg caactctaat cagaggaaga   180
aactaaagga agtaaaacca gatgttttcc accaaagccc tccttttggc tggtctgatt   240
tctaccgcac tggcagggcc atgggctaat atatgtgctg gcaagtcttc caatgagatc   300
cggacgtgtg accgccatgg ctgtggacag tactctgctc aaagaagtca gaggcctcac   360
cagggtgtgg acatcttgtg ctctgctgga tctactgtgt acgcaccatt cactggaatg   420
attgtgggcc aggagaaacc ttatcaaaac aagaatgcta tcaataatgg tgttcgaata   480
tctggaagag gtttttgtgt caaaatgttc tacattaagc caattaagta taaaggtcct   540
attaagaagg gagaaaaact tggaactcta ttgcccttgc agaaagttta tcctggcata   600
caatcgcatg tgcacattga aaactgtgac tcgagtgacc ctactgcata cctgtaaatc   660
gaaggccaat ggtcagatct tcaaaataaa aagtcatctt aaaaacctgg atgcataccc   720
ttctcttcaa gaaatttgtg ttcacaaagg aaaaatgcat gaagggatgg ataccccatt   780
ttccatgaca tgattattac acattgcatg cctgtatcaa aacatctcac gtacctcata   840
aacatataca cctatgtacc cacaaaaatt ttttaattaa aaaaggaaa tttgagttta   900
aatagaaaca tgataaatgc aagaaagaaa acattttgat tttaactcat tgtcactctg   960
atgttcatgt gaactggttg cttcgggctc tttgatctgt cacctatgga atctgagtgg  1020
ttttattttt tagatttctc agtcccaaag atctaagata aataaacaag agaactt    1077
```

<210> SEQ ID NO 2
<211> LENGTH: 849
<212> TYPE: DNA
<213> ORGANISM: Macaca mulatta

<400> SEQUENCE: 2

```
ttagaacttg acttgctcca tactcttata ttttttgtgt ctcacactaa agaaatgaaa    60
gatgcatgat tctaaggcta aatagctagg aagtattcat tcaaacttga atattcttca   120
agagagtgt gggggcaact ctaatcggag gaagaaacat aaaggaagta aacccagatg   180
ttttccacca aagtcctcct ttggctggt ctgattctc tgcactggc agggccatgg   240
gctaatatat gtgctggcaa gtcttccaac gagatccgga cgtgtgaccg ccatggctgt   300
ggacagtact ctgctcaaag aagtcagagg cctcaccagg gtgtggacat cttgtgctct   360
gctggatcta ctgtgtatgc accattcact ggaatgattg tgggccagga gaaaccttat   420
caaaacaaaa atgctatcaa taatggtgtt cgaatatctg gaagaggttt ttgtgtcaaa   480
atgttctaca ttaagccaat taagtataaa ggtcctgtta agaagggaga aaaacttgga   540
actctattgc ccttgcagaa agtttatcct ggcatacagt cgcacgtgca cattgaaaac   600
tgtgacttga gtgaccctac tgcatacctg taaatggaag gccaatggtc agatcttcaa   660
aataaaaagt catcttaaaa acctggatgc ataccccgct cttcaagaaa tttgtattca   720
caaaggaaaa atgcatgaag ggatggatac tccattttcc aggacttggt tattatacat   780
tgcgtgcttg tatcaaaaaa tctcacgtac ctcatatatg tatacacttg tgtacccaca   840
aaatttttt                                                           849
```

<210> SEQ ID NO 3

<211> LENGTH: 889
<212> TYPE: DNA
<213> ORGANISM: Mus musculus

<400> SEQUENCE: 3

```
ggatcagaca gctctccacg gaatgttaca gtttaacccg actcatcttg ctttctgtgt      60
ctcttactag atctcggaga gacataaatt accagagaag attcactcat tccgggggtg     120
accctgtgtg catggagcag gtctaactag aggaagaaac aagaagcaga acctagatga     180
ttcccacaac aatcctcatt tcagctgctt tgctttcctc tgccctagca ggaccatggg     240
ctaacatatg tgccagcaaa tcttccaacg agatccggac gtgtgacagc tatggctgtg     300
gacagtactc tgctcaaaga acccaaaggc atcacccagg tgtggacgtc ctgtgctcgg     360
atggatctgt ggtgtatgca ccattcactg ggaagatagt gggccaggag aaaccctata     420
gaaacaaaaa tgccatcaat gatggcattc gactgtctgg aagaggtttt tgtgtcaaaa     480
ttttctacat taagccaatt aagtataaag gttctatcaa aaggggggag aagctgggca     540
ccttgctgcc cctgcagaaa gtttacccgg gcatccagtc gcatgtacac gttgaaaact     600
gcgactccag tgaccccaca gcatacctgt aagcagagac aaaggccaga tcttctaaat     660
tcaaagccat ctcagaaact gggacatgcc ctgctcccga gaaacgtgc attctaacag      720
aaacataaat ctgtgtaaac actcacaacc ctgattccaa gtcatcaccg ctctgacggg     780
tgggctctgg tcggcctgcc acctcaaggg ccagggagtt tgacatttc gattttagg       840
ttctggtgac tgagataaat gaatgacctc tcatgtgaaa aaaaaaaaa                 889
```

<210> SEQ ID NO 4
<211> LENGTH: 820
<212> TYPE: DNA
<213> ORGANISM: Rattus norvegicus

<400> SEQUENCE: 4

```
tgactcattt tgttttccgt gtctcgtact aaacctcgga gaaacacggg attccaaagc      60
ttaattacca gagaaggtgg actcagtcgt ggactgtgtg tgcatgggag caattctaac     120
cagaggaaga aacggaagc agaatccaga tgtttcccac aagaatcctc atgtcagctg      180
ctttgatttc cactgccctg gcaggaccat gggctaacat atgtgccagc agatcttcca     240
acgagatccg gacatgtgac agctatggct gtggacagta ctctactcaa agaacccaaa     300
ggcatcatcc aggtgtggac gtcctgtgct cagatggatc tgtggtgtat gcgccattca     360
cggggaagat agtgggccag gagaaaccct atagaaacaa aaacgccatc aatgatggcg     420
tccgactgtc gggaagaggt ttctgcgtca aaattttcta cattaagcca attaagtata     480
agggctctat cagaaaggga gagaagctgg gcaccttgct gccccctgcag aaagtttacc    540
ctggcataca gtcgcatgta cacattgaaa actgtgactc cagtgatccc acggcatacc     600
tgtaagcaga gacagaggcc agatcttctc aaattcccag aaactggaac acgtcctgct     660
cctgaagaaa cgtgcattct aacagacgtg ccatcagtgt ggacacaatt ctgattccga     720
ctcagcgtca ctctgatggg cgggctctga tctgcctgct gcctggaggg ccagggagtt     780
ttatgtttcc gatttttaag ttctggggac tgaaattaaa                           820
```

<210> SEQ ID NO 5
<211> LENGTH: 1077
<212> TYPE: DNA
<213> ORGANISM: Homo sapiens

<400> SEQUENCE: 5

```
aagttctctt gtttatttat cttagatctt tgggactgag aaatctaaaa aataaaacca        60
ctcagattcc ataggtgaca gatcaaagag cccgaagcaa ccagttcaca tgaacatcag       120
agtgacaatg agttaaaatc aaaatgtttt ctttcttgca tttatcatgt ttctatttaa       180
actcaaattt cctttttta attaaaaaat ttttgtgggt acataggtgt atatgtttat        240
gaggtacgtg agatgttttg atacaggcat gcaatgtgta ataatcatgt catggaaaat      300
ggggtatcca tcccttcatg cattttcct ttgtgaacac aaattcttg aagagaaggg         360 tatgcatcca ggttttaag atgactttt attttgaaga tctgaccatt ggccttcgat         420
ttacaggtat gcagtagggt cactcgagtc acagttttca atgtgcacat gcgattgtat      480
gccaggataa actttctgca agggcaatag agttccaagt ttttctccct tcttaatagg      540
acctttatac ttaattggct taatgtagaa cattttgaca caaaacctc ttccagatat        600 tcgaacacca ttattgatag cattcttgtt ttgataaggt ttctcctggc ccacaatcat      660
tccagtgaat ggtgcgtaca cagtagatcc agcagagcac aagatgtcca caccctggtg      720
aggcctctga cttctttgag cagagtactg tccacagcca tggcggtcac acgtccggat      780
ctcattggaa gacttgccag cacatatatt agcccatggc cctgccagtg cggtagaaat      840
cagaccagcc aaaaggaggg ctttggtgga aaacatctgg ttttacttcc tttagtttct    900
tcctctgatt agagttgccc ccacactctc tttgaagaat attcaagttt gaatgaatac       960
ttcctagcta tttagcctta gaattctgca tctctcattt ctttagtgtg agacacaaaa    1020
agtttaagag gatggagcaa gtcaagttct aatattccat ggatagctat ttgattt        1077

<210> SEQ ID NO 6
<211> LENGTH: 849
<212> TYPE: DNA
<213> ORGANISM: Macaca mulatta

<400> SEQUENCE: 6
aaaaaatttt gtgggtacac aagtgtatac atatatgagg tacgtgagat ttttgatac         60 aagcacgcaa tgtataataa ccaagtcctg gaaaatggag tatccatccc ttcatgcatt     120
tttcctttgt gaatacaaat ttcttgaaga gcggggtatg catccaggtt tttaagatga    180 cttttatt tgaagatctg accattggcc ttccatttac aggtatgcag tagggtcact        240
caagtcacag ttttcaatgt gcacgtgcga ctgtatgcca ggataaactt tctgcaaggg    300
caatagagtt ccaagttttt ctcccttctt aacaggacct ttatacttaa ttggcttaat    360
gtagaacatt ttgacacaaa aacctcttcc agatattcga acaccattat tgatagcatt    420
tttgttttga taaggtttct cctggcccac aatcattcca gtgaatggtg catacacagt     480
agatccagca gagcacaaga tgtccacacc ctggtgaggc ctctgacttc tttgagcaga    540
gtactgtcca gccatggc ggtcacacgt ccggatctcg ttggaagact tgccagcaca      600
tatattagcc catggccctg ccagtgcagt agaaatcaga ccagccaaaa ggaggacttt    660
ggtggaaaac atctgggttt acttccttta tgtttcttcc tccgattaga gttgccccca    720
cactctcttt gaagaatatt caagtttgaa tgaatacttc ctagctattt agccttagaa    780
tcatgcatct ttcatttctt tagtgtgaga cacaaaaaat ataagagtat ggagcaagtc     840
aagttctaa                                                                    849

<210> SEQ ID NO 7
<211> LENGTH: 889
<212> TYPE: DNA
```

<213> ORGANISM: Mus musculus

<400> SEQUENCE: 7

```
tttttttttt ttcacatgag aggtcattca tttatctcag tcaccagaac ctaaaaatcg      60
aaaatgtcaa actccctggc ccttgaggtg gcaggccgac cagagcccac ccgtcagagc     120
ggtgatgact tggaatcagg gttgtgagtg tttacacaga tttatgtttc tgttagaatg     180
cacgtttctt cgggagcagg gcatgtccca gtttctgaga tggctttgaa tttagaagat     240
ctggcctttg tctctgctta caggtatgct gtggggtcac tggagtcgca gttttcaacg     300
tgtacatgcg actggatgcc cgggtaaact ttctgcaggg gcagcaaggt gcccagcttc     360
tccccctttt tgatagaacc tttatactta attggcttaa tgtagaaaat tttgacacaa     420
aaacctcttc cagacagtcg aatgccatca ttgatggcat ttttgtttct atagggtttc     480
tcctggccca ctatcttccc agtgaatggt gcatacacca cagatccatc cgagcacagg     540
acgtccacac ctgggtgatg cctttgggtt ctttgagcag agtactgtcc acagccatag     600
ctgtcacacg tccggatctc gttggaagat ttgctggcac atatgttagc ccatggtcct     660
gctagggcag aggaaagcaa agcagctgaa atgaggattg ttgtgggaat catctaggtt     720
ctgcttcttg tttcttcctc tagttagacc tgctccatgc acacagggtc accccggaa      780
tgagtgaatc ttctctggta atttatgtct ctccgagatc tagtaagaga cacagaaagc     840
aagatgagtc gggttaaact gtaacattcc gtggagagct gtctgatcc                 889
```

<210> SEQ ID NO 8
<211> LENGTH: 820
<212> TYPE: DNA
<213> ORGANISM: Rattus norvegicus

<400> SEQUENCE: 8

```
tttaatttca gtccccagaa cttaaaaatc ggaaacataa aactccctgg ccctccaggc      60
agcaggcaga tcagagcccg cccatcagag tgacgctgag tcggaatcag aattgtgtcc     120
acactgatgg cacgtctgtt agaatgcacg tttcttcagg agcaggacgt gttccagttt     180
ctgggaattt gagaagatct ggcctctgtc tctgcttaca ggtatgccgt gggatcactg     240
gagtcacagt tttcaatgtg tacatgcgac tgtatgccag ggtaaacttt ctgcagggc      300
agcaaggtgc ccagcttctc tccctttctg atagagccct tatacttaat tggcttaatg     360
tagaaaattt tgacgcagaa acctcttccc gacagtcgga cgccatcatt gatggcgttt     420
ttgtttctat agggtttctc ctggcccact atcttcccg  tgaatggcgc atacaccaca     480
gatccatctg agcacaggac gtccacacct ggatgatgcc tttgggttct tgagtagag      540
tactgtccac agccatagct gtcacatgtc cggatctcgt tggaagatct gctggcacat     600
atgttagccc atggtcctgc cagggcagtg gaaatcaaag cagctgacat gaggattctt     660
gtgggaaaca tctggattct gcttcccgtt tcttcctctg gttagaattg ctcccatgca     720
cacacagtcc acgactgagt ccaccttctc tggtaattaa gctttggaat cccgtgtttc     780
tccgaggttt agtacgagac acggaaaaca aaatgagtca                           820
```

<210> SEQ ID NO 9
<211> LENGTH: 16
<212> TYPE: PRT
<213> ORGANISM: Unknown
<220> FEATURE:
<221> NAME/KEY: source
<223> OTHER INFORMATION: /note="Description of Unknown:
    RFGF peptide"

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 10

Ala Ala Leu Leu Pro Val Leu Leu Ala Ala Pro
1               5                   10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Arg Pro Pro Gln
1               5                   10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
uucuaatatt ccatggauag                                            20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
gagcaagtca agttcuaaua                                            20

```
<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
aagaggatgg agcaagucaa                                            20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
acaaaaagtt taagaggaug                                            20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
uuuagtgtga gacacaaaaa                                            20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
ucucatttct ttagtgugag                                            20

<210> SEQ ID NO 19
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
gaauuctgca tctctcauuu                                                  20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20
uauuuagcct tagaauucug                                                  20

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21
acuucctagc tatttagccu                                                  20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
guuugaatga atactuccua                                                  20

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 23
aauautcaag tttgaaugaa                                               20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24
ucucuttgaa gaatauucaa                                               20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 25
guugccccca cactcucuuu                                               20

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
cugautagag ttgcccccac                                               20

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
uaguutcttc ctctgauuag                                               20

<210> SEQ ID NO 28
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
uuuacttcct ttagtuucuu                                             20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
aacauctggt tttacuuccu                                             20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
ggcuutggtg gaaaacaucu                                             20

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 31
gccaaaagga gggctuuggu                                             20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 32
aaucagacca gccaaaagga                                                     20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
gugcggtaga aatcagacca                                                     20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 34
auggccctgc cagtgcggua                                                     20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
uauautagcc catggcccug                                                     20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
cuugccagca catatauuag                                                     20
```

```
<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 37
cauuggaaga cttgccagca                                             20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 38
acguccggat ctcatuggaa                                             20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 39
auggcggtca cacgtccgga                                             20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 40
guccacagcc atggcgguca                                             20

<210> SEQ ID NO 41
<211> LENGTH: 20
<212> TYPE: DNA
<213> ORGANISM: Artificial Sequence
<220> FEATURE:
```

<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 41
gagcagagta ctgtccacag                                              20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 42
ugacutcttt gagcagagua                                              20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 43
gugaggcctc tgactucuuu                                              20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 44
uccacaccct ggtgaggccu                                              20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
gagcacaaga tgtccacacc                                              20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 46
agauccagca gagcacaaga                                              20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 47
ugcguacaca gtagauccag                                              20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 48
cagugaatgg tgcgtacaca                                              20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
cacaatcatt ccagtgaaug                                              20

<210> SEQ ID NO 50

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 50
uucucctggc ccacaaucau                                              20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 51
guuuugataa ggtttcuccu                                              20

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 52
uagcattctt gttttgauaa                                              20

<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 53
ccauuattga tagcauucuu                                              20

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 54 gauaucgaa caccauuauu                                                    20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 55
aaacctcttc cagatauucg                                                   20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 56
uuuugacaca aaaaccucuu                                                   20

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 57
uguagaacat tttgacacaa                                                   20

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 58
```
uuaautggct taatguagaa                                              20

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 59
ccuuuatact taattggcuu                                              20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 60
uucuuaatag gacctuuaua                                              20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 61
aguuuttctc ccttcuuaau                                              20

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 62
auagagttcc aagttuuucu                                              20

<210> SEQ ID NO 63
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 63
gcaagggcaa tagaguucca                                                  20

<210> SEQ ID NO 64
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 64
auaaactttc tgcaagggca                                                  20

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 65
auuguatgcc aggataaacu                                                  20

<210> SEQ ID NO 66
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 66
gcacatgcga ttgtaugcca                                                  20

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 67
aguuutcaat gtgcacaugc                                           20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 68
acucgagtca cagttuucaa                                           20

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 69
caguagggtc actcgaguca                                           20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 70
uuuacaggta tgcaguaggg                                           20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
uggccttcga tttacaggua                                           20

-continued

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 72
aagauctgac cattggccuu                                              20

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 73
uuuuuatttt gaagaucuga                                              20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 74
uuaagatgac tttttauuuu                                              20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 75
cauccaggtt tttaagauga                                              20

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

```
                              Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 76
gaagggtatg catccagguu                                                  20

<210> SEQ ID NO 77
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 77
aauuucttga agagaagggu                                                  20

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 78
gugaacacaa atttcuugaa                                                  20

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 79
cauuuttcct ttgtgaacac                                                  20

<210> SEQ ID NO 80
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 80
```
cauccctuca tgcatuuuuc                                           20

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 81 augggtatc catcccuuca                                            20

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 82
augucatgga aaatggggua                                           20

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 83
guaauaatca tgtcauggaa                                           20

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 84
aggcatgcaa tgtgtaauaa                                           20

<210> SEQ ID NO 85
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 85
guuuugauac aggcaugcaa                                                    20

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 86
guacgtgaga tgtttugaua                                                    20

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 87
uauguuuatg aggtacguga                                                    20

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 88
cauaggtgta tatgtuuaug                                                    20

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

-continued

```
<223> OTHER INFORMATION: /note="Description of Combined DNA/RNA
      Molecule: Synthetic oligonucleotide"

<400> SEQUENCE: 89 uuuguggta cataggugua                                                  20

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 90
auuaaaaaat ttttgugggu                                                 20

<210> SEQ ID NO 91
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 91
uuccuttttt taattaaaaa                                                 20

<210> SEQ ID NO 92
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 92
aaacucaaat ttcctuuuuu                                                 20

<210> SEQ ID NO 93
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 93
uguuuctatt taaacucaaa                                                 20
```

```
<210> SEQ ID NO 94
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 94
cuugcattta tcatguuucu                                              20

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 95
auguuttctt tcttgcauuu                                              20

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 96
aaaaucaaaa tgtttucuuu                                              20

<210> SEQ ID NO 97
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 97
gacaatgagt taaaaucaaa                                              20

<210> SEQ ID NO 98
<211> LENGTH: 20
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 98
gaacatcaga gtgacaauga                                              20

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 99
caguucacat gaacaucaga                                              20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 100
agcccgaagc aaccaguuca                                              20

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 101
cagaucaaag agcccgaagc                                              20

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

```
<400> SEQUENCE: 102
uccauaggtg acagaucaaa                                              20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 103
accactcaga ttccauaggu                                              20

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 104
aaaaaataaa accacucaga                                              20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 105
cugagaaatc taaaaaauaa                                              20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 106
uagauctttg ggactgagaa                                              20

<210> SEQ ID NO 107
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 107
uuauutatct tagatcuuug                                              20

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 108
guucucttgt ttattuaucu                                              20

<210> SEQ ID NO 109
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cuauccaugg aauauuagaa                                              20

<210> SEQ ID NO 110
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
uauuagaacu ugacuugcuc                                              20

<210> SEQ ID NO 111
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
uugacuugcu ccauccucuu                                              20

<210> SEQ ID NO 112
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
cauccucuua aacuuuuugu                                              20

<210> SEQ ID NO 113
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
uuuuuguguc ucacacuaaa                                              20

<210> SEQ ID NO 114
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
cucacacuaa agaaaugaga                                              20

<210> SEQ ID NO 115
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
aaaugagaga ugcagaauuc                                              20

<210> SEQ ID NO 116
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
cagaauucua aggcuaaaua                                              20

<210> SEQ ID NO 117
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
aggcuaaaua gcuaggaagu                                              20
```

```
<210> SEQ ID NO 118
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
uaggaaguau ucauucaaac                                             20

<210> SEQ ID NO 119
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
uucauucaaa cuugaauauu                                             20

<210> SEQ ID NO 120
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
uugaauauuc uucaaagaga                                             20

<210> SEQ ID NO 121
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
aaagagagug uggggcaac                                              20

<210> SEQ ID NO 122
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122 guggggcaa cucuaaucag                                              20

<210> SEQ ID NO 123
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 123
cuaaucagag gaagaaacua                                               20

<210> SEQ ID NO 124
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
aagaaacuaa aggaaguaaa                                               20

<210> SEQ ID NO 125
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
aggaaguaaa accagauguu                                               20

<210> SEQ ID NO 126
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
agauguuuuc caccaaagcc                                               20

<210> SEQ ID NO 127
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
accaaagccc uccuuuuggc                                               20

<210> SEQ ID NO 128
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
uccuuuuggc uggucugauu                                               20

<210> SEQ ID NO 129
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
uggucugauu ucuaccgcac                                                    20

<210> SEQ ID NO 130
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
uaccgcacug gcagggccau                                                    20

<210> SEQ ID NO 131
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
cagggccaug ggcuaauaua                                                    20

<210> SEQ ID NO 132
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
cuaauauaug ugcuggcaag                                                    20

<210> SEQ ID NO 133
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
ugcuggcaag ucuuccaaug                                                    20

<210> SEQ ID NO 134
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
```
uuccaaugag auccggacgu                                          20

<210> SEQ ID NO 135
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
uccggacgug ugaccgccau                                          20

<210> SEQ ID NO 136
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
ugaccgccau ggcuguggac                                          20

<210> SEQ ID NO 137
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cuguggacag uacucugcuc                                          20

<210> SEQ ID NO 138
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
uacucugcuc aaagaaguca                                          20

<210> SEQ ID NO 139
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
aaagaaguca gaggccucac                                          20

<210> SEQ ID NO 140
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 140
aggccucacc agggugugga                                              20

<210> SEQ ID NO 141
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141 ggguggaca ucuugugcuc                                               20

<210> SEQ ID NO 142
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ucuugugcuc ugcuggaucu                                              20

<210> SEQ ID NO 143
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
cuggaucuac uguguacgca                                              20

<210> SEQ ID NO 144
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
uguguacgca ccauucacug                                              20

<210> SEQ ID NO 145
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
cauucacugg aaugauugug                                              20

<210> SEQ ID NO 146
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
augauugugg gccaggagaa                                             20

<210> SEQ ID NO 147
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
aggagaaacc uuaucaaaac                                             20

<210> SEQ ID NO 148
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
uuaucaaaac aagaaugcua                                             20

<210> SEQ ID NO 149
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
aagaaugcua ucaauaaugg                                             20

<210> SEQ ID NO 150
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
aauaauggug uucgaauauc                                             20

<210> SEQ ID NO 151
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
```

```
cgaauaucug gaagagguuu                                               20

<210> SEQ ID NO 152
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
aagagguuuu ugugucaaaa                                               20

<210> SEQ ID NO 153
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
uugugucaaa auguucuaca                                               20

<210> SEQ ID NO 154
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
uucuacauua agccaauuaa                                               20

<210> SEQ ID NO 155
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
aagccaauua aguauaaagg                                               20

<210> SEQ ID NO 156
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
uauaaagguc cuauuaagaa                                               20

<210> SEQ ID NO 157
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 157
auuaagaagg gagaaaaacu                                                  20

<210> SEQ ID NO 158
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
agaaaaacuu ggaacucuau                                                  20

<210> SEQ ID NO 159
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
uggaacucua uugcccuugc                                                  20

<210> SEQ ID NO 160
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
ugcccuugca gaaaguuuau                                                  20

<210> SEQ ID NO 161
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
aguuuauccu ggcauacaau                                                  20

<210> SEQ ID NO 162
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
uggcauacaa ucgcaugugc                                                  20
```

<210> SEQ ID NO 163
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gcaugugcac auugaaaacu                                              20

<210> SEQ ID NO 164
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
uugaaaacug ugacucgagu                                              20

<210> SEQ ID NO 165
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
ugacucgagu gacccuacug                                              20

<210> SEQ ID NO 166
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
cccuacugca uaccuguaaa                                              20

<210> SEQ ID NO 167
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
uaccuguaaa ucgaaggcca                                              20

<210> SEQ ID NO 168
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 168
aaggccaaug gucagaucuu                                               20

<210> SEQ ID NO 169
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
ucagaucuuc aaaauaaaaa                                               20

<210> SEQ ID NO 170
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aaaauaaaaa gucaucuuaa                                               20

<210> SEQ ID NO 171
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ucaucuuaaa aaccuggaug                                               20

<210> SEQ ID NO 172
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
aaccuggaug cauacccuuc                                               20

<210> SEQ ID NO 173
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
acccuucucu ucaagaaauu                                               20

<210> SEQ ID NO 174
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 174
uucaagaaau uuguguucac                                              20

<210> SEQ ID NO 175
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
guguucacaa aggaaaaaug                                              20

<210> SEQ ID NO 176
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gaaaaaugca ugaagggaug                                              20

<210> SEQ ID NO 177
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
ugaagggaug gauaccccau                                              20

<210> SEQ ID NO 178
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
uaccccauuu uccaugacau                                              20

<210> SEQ ID NO 179
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
uuccaugaca ugauuauuac                                              20
```

```
<210> SEQ ID NO 180
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
uuauuacaca uugcaugccu                                                    20

<210> SEQ ID NO 181
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
uugcaugccu guaucaaaac                                                    20

<210> SEQ ID NO 182
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
uaucaaaaca ucucacguac                                                    20

<210> SEQ ID NO 183
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ucacguaccu cauaaacaua                                                    20

<210> SEQ ID NO 184
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
cauaaacaua uacaccuaug                                                    20

<210> SEQ ID NO 185
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 185
uacaccuaug uacccacaaa                                                    20

<210> SEQ ID NO 186
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
acccacaaaa auuuuuaau                                                     20

<210> SEQ ID NO 187
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
uuuuuaauua aaaaaaggaa                                                    20

<210> SEQ ID NO 188
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aaaaaaggaa auuugaguuu                                                    20

<210> SEQ ID NO 189
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
uuugaguuua aauagaaaca                                                    20

<210> SEQ ID NO 190
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
agaaacauga uaaaugcaag                                                    20

<210> SEQ ID NO 191
<211> LENGTH: 20
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
aaaugcaaga aagaaaacau                                              20

<210> SEQ ID NO 192
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
aaagaaaaca uuuugauuuu                                              20

<210> SEQ ID NO 193
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
uuugauuuua acucauuguc                                              20

<210> SEQ ID NO 194
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
ucauugucac ucugauguuc                                              20

<210> SEQ ID NO 195
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
ucugauguuc augugaacug                                              20

<210> SEQ ID NO 196
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ugaacugguu gcuucgggcu                                              20
```

-continued

```
<210> SEQ ID NO 197
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
gcuucgggcu cuuugaucug                                                       20

<210> SEQ ID NO 198
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
uuugaucugu caccuaugga                                                       20

<210> SEQ ID NO 199
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
accuauggaa ucgaguggu                                                        20

<210> SEQ ID NO 200
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200 ucgaguggu uuuauuuuuu                                                        20

<210> SEQ ID NO 201
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
uuauuuuuua gauuucucag                                                       20

<210> SEQ ID NO 202
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 202
uucucagucc caaagaucua                                               20

<210> SEQ ID NO 203
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
caaagaucua agauaaauaa                                               20

<210> SEQ ID NO 204
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
agauaaauaa acaagagaac                                               20

<210> SEQ ID NO 205
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
uucuaauauu ccauggauag                                               20

<210> SEQ ID NO 206
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gagcaaguca aguucuaaua                                               20

<210> SEQ ID NO 207
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
aagaggaugg agcaagucaa                                               20

<210> SEQ ID NO 208
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
acaaaaaguu uaagaggaug                                                 20

<210> SEQ ID NO 209
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
uuuaguguga gacacaaaaa                                                 20

<210> SEQ ID NO 210
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ucucauuucu uuagugugag                                                 20

<210> SEQ ID NO 211
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gaauucugca ucucucauuu                                                 20

<210> SEQ ID NO 212
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
uauuuagccu uagaauucug                                                 20

<210> SEQ ID NO 213
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
```
acuuccuagc uauuuagccu					20

<210> SEQ ID NO 214
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
guuugaauga auacuuccua					20

<210> SEQ ID NO 215
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aauauucaag uuugaaugaa					20

<210> SEQ ID NO 216
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
ucucuuugaa gaauauucaa					20

<210> SEQ ID NO 217
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
guugccccca cacucucuuu					20

<210> SEQ ID NO 218
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
cugauuagag uugcccccac					20

<210> SEQ ID NO 219
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 219
uaguuucuuc cucugauuag                                                   20

<210> SEQ ID NO 220
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
uuuacuuccu uuaguuucuu                                                   20

<210> SEQ ID NO 221
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
aacaucuggu uuuacuuccu                                                   20

<210> SEQ ID NO 222
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
ggcuuuggug gaaaacaucu                                                   20

<210> SEQ ID NO 223
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gccaaaagga gggcuuuggu                                                   20

<210> SEQ ID NO 224
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
aaucagacca gccaaaagga                                                   20

<210> SEQ ID NO 225
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gugcgguaga aaucagacca                                               20

<210> SEQ ID NO 226
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
auggcccugc cagugcggua                                               20

<210> SEQ ID NO 227
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
uauauuagcc cauggcccug                                               20

<210> SEQ ID NO 228
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
cuugccagca cauauauuag                                               20

<210> SEQ ID NO 229
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
cauuggaaga cuugccagca                                               20

<210> SEQ ID NO 230
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
```
acguccggau cucauuggaa                                              20

<210> SEQ ID NO 231
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
auggcgguca cacguccgga                                              20

<210> SEQ ID NO 232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
guccacagcc auggcgguca                                              20

<210> SEQ ID NO 233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
gagcagagua cuguccacag                                              20

<210> SEQ ID NO 234
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ugacuucuuu gagcagagua                                              20

<210> SEQ ID NO 235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gugaggccuc ugacuucuuu                                              20

<210> SEQ ID NO 236
<211> LENGTH: 20
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 236
uccacacccu ggugaggccu                                                    20

<210> SEQ ID NO 237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
gagcacaaga uguccacacc                                                    20

<210> SEQ ID NO 238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
agauccagca gagcacaaga                                                    20

<210> SEQ ID NO 239
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
ugcguacaca guagauccag                                                    20

<210> SEQ ID NO 240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
cagugaaugg ugcguacaca                                                    20

<210> SEQ ID NO 241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
cacaaucauu ccagugaaug                                                    20

```
<210> SEQ ID NO 242
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
uucuccuggc ccacaaucau                                              20

<210> SEQ ID NO 243
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
guuuugauaa gguuucuccu                                              20

<210> SEQ ID NO 244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
uagcauucuu guuuugauaa                                              20

<210> SEQ ID NO 245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ccauuauuga uagcauucuu                                              20

<210> SEQ ID NO 246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gauauucgaa caccauuauu                                              20

<210> SEQ ID NO 247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 247
aaaccucuuc cagauauucg                                               20

<210> SEQ ID NO 248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
uuuugacaca aaaccucuu                                                20

<210> SEQ ID NO 249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
uguagaacau uuugacacaa                                               20

<210> SEQ ID NO 250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
uuaauuggcu uaauguagaa                                               20

<210> SEQ ID NO 251
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ccuuuauacu uaauuggcuu                                               20

<210> SEQ ID NO 252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
uucuuaauag gaccuuuaua                                               20

<210> SEQ ID NO 253
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 253 aguuuucuc ccuucuuaau                                              20

<210> SEQ ID NO 254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
auagaguucc aaguuuuucu                                             20

<210> SEQ ID NO 255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gcaagggcaa uagaguucca                                             20

<210> SEQ ID NO 256
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
auaaacuuuc ugcaagggca                                             20

<210> SEQ ID NO 257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
auuguaugcc aggauaaacu                                             20

<210> SEQ ID NO 258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gcacaugcga uuguaugcca                                             20
```

```
<210> SEQ ID NO 259
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
aguuuucaau gugcacaugc                                              20

<210> SEQ ID NO 260
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
acucgaguca caguuuucaa                                              20

<210> SEQ ID NO 261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
caguaggguc acucgaguca                                              20

<210> SEQ ID NO 262
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
uuuacaggua ugcaguaggg                                              20

<210> SEQ ID NO 263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
uggccuucga uuuacaggua                                              20

<210> SEQ ID NO 264
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 264
aagaucugac cauuggccuu                                              20

<210> SEQ ID NO 265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
uuuuuauuuu gaagaucuga                                              20

<210> SEQ ID NO 266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
uuaagaugac uuuuuauuuu                                              20

<210> SEQ ID NO 267
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
cauccagguu uuuaagauga                                              20

<210> SEQ ID NO 268
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gaaggguaug cauccagguu                                              20

<210> SEQ ID NO 269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
aauuucuuga agagaagggu                                              20

<210> SEQ ID NO 270
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
gugaacacaa auuucuugaa                                                      20

<210> SEQ ID NO 271
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271 cauuuuccu uugugaacac                                                       20

<210> SEQ ID NO 272
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
caucccuuca ugcauuuuuc                                                      20

<210> SEQ ID NO 273
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
augggguauc caucccuuca                                                      20

<210> SEQ ID NO 274
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
augucaugga aaaugggua                                                       20

<210> SEQ ID NO 275
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
guaauaauca ugucauggaa                                                      20
```

```
<210> SEQ ID NO 276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
aggcaugcaa uguguaauaa                                              20

<210> SEQ ID NO 277
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
guuuugauac aggcaugcaa                                              20

<210> SEQ ID NO 278
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
guacgugaga uguuuugaua                                              20

<210> SEQ ID NO 279
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
uauguuuaug agguacguga                                              20

<210> SEQ ID NO 280
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
cauaggugua uauguuuaug                                              20

<210> SEQ ID NO 281
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 281
uuugugggua cauaggugua                                          20

<210> SEQ ID NO 282
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
auuaaaaaau uuugugggu                                           20

<210> SEQ ID NO 283
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
uuccuuuuuu uaauuaaaaa                                          20

<210> SEQ ID NO 284
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
aaacucaaau uuccuuuuuu                                          20

<210> SEQ ID NO 285
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
uguuucuauu uaaacucaaa                                          20

<210> SEQ ID NO 286
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
cuugcauuua ucauguuucu                                          20

<210> SEQ ID NO 287
<211> LENGTH: 20

-continued

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
auguuuucuu ucuugcauuu                                           20

<210> SEQ ID NO 288
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
aaaaucaaaa uguuuucuuu                                           20

<210> SEQ ID NO 289
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
gacaaugagu uaaaaucaaa                                           20

<210> SEQ ID NO 290
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
gaacaucaga gugacaauga                                           20

<210> SEQ ID NO 291
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
caguucacau gaacaucaga                                           20

<210> SEQ ID NO 292
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292

-continued agcccgaagc aaccaguuca         20

<210> SEQ ID NO 293
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
cagaucaaag agcccgaagc         20

<210> SEQ ID NO 294
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
uccauaggug acagaucaaa         20

<210> SEQ ID NO 295
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
accacucaga uuccauaggu         20

<210> SEQ ID NO 296
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
aaaaaauaaa accacucaga         20

<210> SEQ ID NO 297
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 297
cugagaaauc uaaaaaauaa                                              20

<210> SEQ ID NO 298
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
uagaucuuug ggacugagaa                                              20

<210> SEQ ID NO 299
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
uuauuuaucu uagaucuuug                                              20

<210> SEQ ID NO 300
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
guucucuugu uuauuuaucu                                              20
```

COMPOSITIONS AND METHODS FOR INHIBITING EXPRESSION OF THE LECT2 GENE

CROSS-REFERENCE TO RELATED APPLICATIONS

This application is a U.S. National Stage Application under 35 U.S.C. § 371 of International Application No. PCT/US2016/026676, filed Apr. 8, 2016, which claims the benefit of U.S. Provisional Application No. 62/144,695, filed Apr. 8, 2015, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 6, 2016, is named A2038-7221WO_SL.txt and is 96,680 bytes in size.

FIELD OF THE INVENTION

The invention relates to the specific inhibition of the expression of the LECT2 gene.

BACKGROUND OF THE INVENTION

Amyloidosis is a group of diseases characterized by deposition of insoluble fibrous protein aggregates, called amyloids, in organs or tissues. Amyloids can form from mutant or wild type proteins. One system of nomenclature for amyloid diseases uses an abbreviation for the protein that forms amyloid deposits, preceded by the letter "A." Thus, for example, ALECT2 is the abbreviation for an amyloidosis involving deposit of amyloids formed from leukocyte cell derived chemotactic factor-2 (ALECT2).

LECT2 amyloidosis (ALECT2) is one of the most recently discovered types of amyloidosis. LECT2 amyloidosis has been observed in individuals with renal or hepatic amyloidosis. This form of amyloidosis can present with nephrotic syndrome or with liver involvement (e.g., hepatitis, e.g., chronic hepatitis). It may be particularly prevalent in Mexican Americans and/or individuals who are homozygous for the G allele encoding valine at position 40 in the mature LECT2 protein (or at position 58 in the unprocessed protein). Treatments for LECT2 amyloidosis are limited, and new treatments are needed.

SUMMARY OF THE INVENTION

The present invention provides antisense polynucleotide agents and compositions comprising such agents which target nucleic acids encoding a LECT2 gene and interfere with the normal function of the targeted nucleic acid. The LECT2 nucleic acid may be within a cell, e.g., a cell within a subject, such as a human. The present invention also provides methods and combination therapies for treating a subject having a disorder that would benefit from inhibiting or reducing the expression of a LECT2 mRNA, e.g., a LECT2-associated disease, such as amyloidosis, e.g., a LECT2 amyloidosis (ALECT2) using the antisense polynucleotide agents and compositions of the invention.

Accordingly, in one aspect, the present invention provides antisense polynucleotide agents for inhibiting expression of a LECT2 gene. The agents comprise about 4 to about 50 contiguous nucleotides, wherein the nucleotide sequence of the agent is about 80% complementary over its entire length to the equivalent region of the nucleotide sequence of any one of SEQ ID NOs: 1-4.

In one embodiment, the equivalent region is one of the target regions of SEQ ID NO: 1 provided in Table 3, e.g., SEQ ID NOs: 109-204.

In one embodiment, the nucleotides of an antisense polynucleotide agent of the invention are un-modified, and do not comprise, e.g., chemical modifications and/or conjugations known in the art and described herein (e.g., as shown in Table 3). In another embodiment, one or more (e.g., at least 5, 10, 11, 12, 13, 14, 15, 16, 17, 18, 19, 20 or more) of the nucleotides of an antisense polynucleotide agent of the invention is chemically modified (e.g., as shown in Table 3).

In another aspect, the present invention provides antisense polynucleotide agents for inhibiting expression of a LECT2 gene, wherein the agent comprises at least 8 contiguous nucleotides differing by no more than 3 nucleotides from any one of the nucleotide sequences listed in Table 3.

In some embodiments, substantially all of the nucleotides of the antisense polynucleotide agents of the invention are modified nucleotides. In other embodiment, all of the nucleotides of the antisense polynucleotide agent are modified nucleotides.

The antisense polynucleotide agent may be 10 to 40 nucleotides in length; 10 to 30 nucleotides in length; 18 to 30 nucleotides in length; 10 to 24 nucleotides in length; 18 to 24 nucleotides in length; 14-20 nucleotides in length; or 14 or 20 nucleotides in length.

In one embodiment, the modified nucleotide comprises a modified sugar moiety selected from the group consisting of: a 2'-O-methoxyethyl modified sugar moiety, a 2'-methoxy modified sugar moiety, a 2'-O-alkyl modified sugar moiety, and a bicyclic sugar moiety.

In one embodiment, the bicyclic sugar moiety has a (—CH2-)n group forming a bridge between the 2' oxygen and the 4' carbon atoms of the sugar ring, wherein n is 1 or 2.

In another embodiment, the modified nucleotide is a 5-methylcytosine.

In one embodiment, the modified nucleotide comprises a modified internucleoside linkage, such as a phosphorothioate internucleoside linkage.

In one embodiment, an agent of the invention comprises a plurality of 2'-deoxynucleotides flanked on each side by at least one nucleotide having a modified sugar moiety.

In one embodiment, the agent is a gapmer comprising a gap segment comprised of linked 2'-deoxynucleotides positioned between a 5' and a 3' wing segment.

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In one embodiment, the 5'-wing segment is 1 to 6 nucleotides in length, e.g., 2, 3, 4, or 5 nucleotides in length.

In one embodiment, the 3'-wing segment is 1 to 6 nucleotides in length, e.g., 2, 3, 4, or 5 nucleotides in length.

In one embodiment, the gap segment is 5 to 14 nucleotides in length, e.g., 10 nucleotides in length.

In one aspect, the present invention provides antisense polynucleotide agent for inhibiting LECT2 gene expression, comprising a gap segment consisting of linked deoxynucleotides; a 5'-wing segment consisting of linked nucleotides; a 3'-wing segment consisting of linked nucleotides; wherein the gap segment is positioned between the 5'-wing segment and the 3'-wing segment and wherein each nucleotide of each wing segment comprises a modified sugar.

In one embodiment, the gap segment is ten 2'-deoxynucleotides in length and each of the wing segments is five nucleotides in length.

In another embodiment, the gap segment is ten 2'-deoxynucleotides in length and each of the wing segments is four nucleotides in length.

In yet another embodiment, the gap segment is ten 2'-deoxynucleotides in length and each of the wing segments is three nucleotides in length.

In another embodiment, the gap segment is ten 2'-deoxynucleotides in length and each of the wing segments is two nucleotides in length.

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In some embodiments, the agents of the invention further comprise a ligand.

In one embodiment, the agent is conjugated to the ligand at the 3'-terminus.

In one embodiment, the ligand is an N-acetylgalactosamine (GalNAc) derivative.

In one embodiment, the ligand is

RNA carrying an allelic variant). For example, an antisense polynucleotide agent featured in the invention can target a polymorphic variant, such as a single nucleotide polymorphism (SNP), of LECT2.

In one aspect, the present invention provides pharmaceutical compositions for inhibiting expression of a LECT2 gene comprising the agents of the invention.

In one embodiment, the agent is present in an unbuffered solution, such as saline or water.

In another embodiment, the agent is present in a buffer solution, such as a buffer comprising acetate, citrate, prolamine, carbonate, or phosphate or any combination thereof.

In one embodiment, the buffer solution is phosphate buffered saline (PBS).

In another aspect, the present invention provides pharmaceutical composition comprising an agent of the invention and a lipid formulation, such as a lipid formulation comprising an LNP or a MC3.

In one aspect, the present invention provides methods of inhibiting LECT2 gene expression in a cell. The methods include contacting the cell with the agent of the invention or a pharmaceutical composition of the invention; and maintaining the cell for a time sufficient to obtain antisense inhibition of a LECT2 gene, thereby inhibiting expression of the LECT2 gene in the cell.

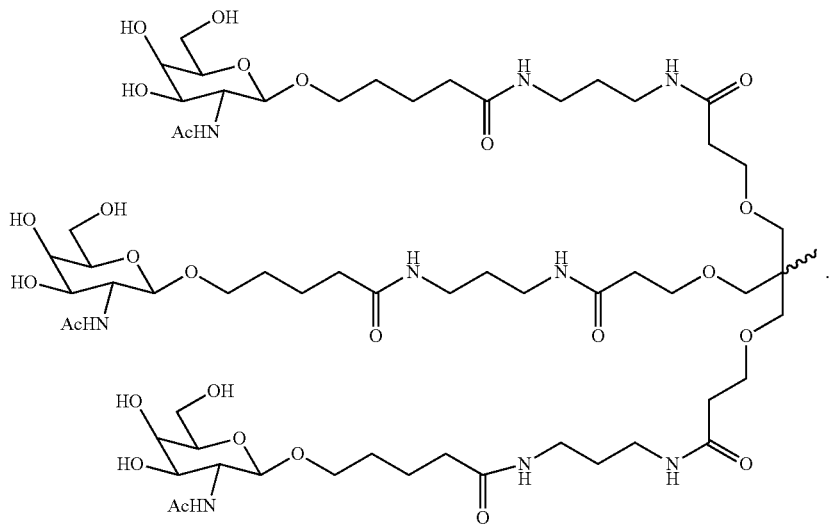

In one embodiment, the antisense polynucleotide agent has a region that is substantially complementary to a portion of a LECT2 mRNA, e.g., a human LECT2 mRNA (e.g., a human LECT2 mRNA as provided in NM_002302.2 (SEQ ID NO: 1).

In embodiments, the antisense polynucleotide agent has a region that is substantially complementary to a portion of a LECT2 mRNA transcript that has a A to G substitution at nucleotide position 373 of SEQ ID NO: 1. In embodiments, the mRNA transcript encodes valine at position 40 in the mature LECT2 protein (or amino acid 58 in the unprocessed protein). In embodiments, the mRNA transcript encodes isoleucine at position 40 in the mature LECT2 protein (or amino acid 58 in the unprocessed protein).

In one embodiment, an antisense polynucleotide agent as described herein targets a wildtype LECT2 RNA transcript variant, and in another embodiment, the antisense polynucleotide agent targets a mutant transcript (e.g., a LECT2

In one embodiment, the cell is within a subject.

In one embodiment, the subject is a human.

In one embodiment, the LECT2 gene expression is inhibited by at least about 30%, about 40%, about 50%, about 60%, about 70%, about 80%, about 90%, about 95%, about 98% or about 100%.

In another aspect, the present invention provides methods of treating a subject having a disease or disorder that would benefit from reduction in LECT2 gene expression. The methods include administering to the subject a therapeutically effective amount of an agent of the invention or a pharmaceutical composition of the invention, thereby treating the subject.

In yet another aspect, the present invention provides methods of preventing at least one symptom in a subject having a disease or disorder that would benefit from reduction in LECT2 gene expression. The methods include administering to the subject a prophylactically effective amount of the agent of the invention or a pharmaceutical composition of the invention, thereby preventing at least one symptom in the subject having a disorder that would benefit from reduction in LECT2 gene expression.

In one embodiment, the administration of the antisense polynucleotide agent to the subject causes a decrease in amyloid deposition (e.g., by preventing amyloid deposition or reducing amyloid deposition, e.g., by reducing size, number, or extent of amyloid deposits) or symptoms associated with amyloid deposition and/or a decrease in LECT2 protein levels.

In one embodiment, the administration of the antisense polynucleotide agent to the subject inhibits amyloid deposition (e.g., by preventing amyloid deposition or reducing amyloid deposition, e.g., by reducing size, number, or extent of amyloid deposits). The inhibition optionally involves an inhibition of at least 5%, 10%, 15%, 20%, 25%, 30%, 35%, 40%, 45%, 50% or more compared to a reference, (e.g., a control that is untreated or treated with a non-targeting dsRNA (e.g., a dsRNA that does not target LECT2)).

In one embodiment, the disorder is a LECT2-associated disease, e.g., a LECT2 amyloidosis. In some embodiments, the LECT2 amyloidosis is a renal amyloidosis. In some embodiments, the LECT2 amyloidosis involves amyloid deposition in the kidney. In some embodiments, LECT2 amyloidosis is associated with renal disease (e.g., nephrotic syndrome). In some embodiments, the amyloidosis is associated with proteinuria. In some embodiments, proteinuria is absent. In some embodiments, the LECT2 amyloidosis is a hepatic amyloidosis. In some embodiments, the LECT2 amyloidosis involves amyloid deposition in the liver. In some embodiments, the LECT2 amyloidosis is associated with inflammation in the liver (e.g., hepatitis, e.g., chronic hepatitis).

In one embodiment the subject is human. In some embodiments, the subject is of Mexican descent (e.g., a Mexican American).

In embodiments, the subject carries the G allele of the LECT2 gene that encodes valine at position 40 in the mature protein (or amino acid 58 in the unprocessed protein). In embodiments, the subject is homozygous for the G allele (G/G genotype). In embodiments, a LECT2 protein expressed in the subject has valine at position 40 in the mature protein (or at amino acid 58 in the unprocessed protein).

In one embodiment, the agent is administered at a dose of about 0.01 mg/kg to about 10 mg/kg or about 0.5 mg/kg to about 50 mg/kg.

In one embodiment, the agent is administered at a dose of about 10 to 100 mg/kg or 0.5 to 10 mg/kg.

In one embodiment, the agent is administered to the subject once a week.

In another embodiment, the agent is administered to the subject twice a week.

In yet another embodiment, the agent is administered to the subject twice a month.

In one embodiment, the agent is administered to the subject subcutaneously.

In another embodiment, a composition the agent featured in the invention is administered in conjunction with a second therapy for a disorder related to LECT2 expression (e.g., a LECT2 amyloidosis). The agent can be administered before, after, or concurrent with a second therapy. In embodiments, the agent is administered before the second therapy. In embodiments, the agent is administered after the second therapy. In embodiments, the agent is administered concurrent with the second therapy.

In some embodiments, the second therapy is a non-antisense polynucleotide therapeutic agent that is effective to treat the disorder or symptoms of the disorder.

In some embodiments, the disorder to be treated by the compositions or methods disclosed herein is a LECT2 amyloidosis that affects kidney function, e.g., through amyloid deposition in the kidney. In some such embodiments, the agent is administered in conjunction with a therapy that supports kidney function (e.g., dialysis). In embodiments, the agent is administered in conjunction with a diuretic, an ACE (angiotensin converting enzyme) inhibitor, an angiotensin receptor blocker, and/or dialysis, e.g., to support or manage kidney function.

In some embodiments, the disorder to be treated by the compositions or methods disclosed herein is a LECT2 amyloidosis involving amyloid deposits in the liver. In some such embodiments, the agent is administered in conjunction with a therapy that supports liver function.

In some embodiments, the disorder to be treated by the compositions or methods disclosed herein is a LECT2 amyloidosis, and the agent is administered in conjunction with removal of all or part of the organ(s) affected by the amyloidosis (e.g., resection of all or part of kidney or liver tissue affected by the amyloidosis). The removal is optionally conducted in conjunction with a replacement of all or part of the organ removed (e.g., in conjunction with a kidney or liver organ transplant).

In one embodiment, the methods of the invention further include administering an anti-LECT2 antibody, or antigen-binding fragment thereof, to the subject.

DETAILED DESCRIPTION OF THE INVENTION

The present invention provides antisense polynucleotide agents and compositions comprising such agents which target nucleic acids encoding LECT2 (e.g., mRNA encoding LECT2 as provided in, for example, any one of SEQ ID NOs: 1-4). The antisense polynucleotide agents bind to nucleic acids encoding LECT2 via, e.g., Watson-Crick base pairing, and interfere with the normal function of the targeted nucleic acid.

The antisense polynucleotide agents of the invention include a nucleotide sequence which is about 4 to about 50 nucleotides or less in length and which is about 80% complementary to at least part of an mRNA transcript of a LECT2 gene. The use of these antisense polynucleotide agents enables the targeted inhibition of RNA expression and/or activity of a LECT2 gene in mammals.

The present inventors have demonstrated that antisense polynucleotide agents targeting LECT2 can mediate antisense inhibition in vitro resulting in significant inhibition of expression of a LECT2 gene. Thus, methods and compositions including these antisense polynucleotide agents are useful for treating a subject who would benefit by a reduction in the levels and/or activity of a LECT2 protein, such as a subject having a LECT2-associated disease, such as e.g., amyloidosis, e.g., LECT2 amyloidosis.

The present invention also provides methods and combination therapies for treating a subject having a disorder that would benefit from inhibiting or reducing the expression of a LECT2 gene, e.g., a LECT2-associated disease, such as amyloidosis, e.g. a LECT2 amyloidosis (ALECT2) using the antisense polynucleotide agents and compositions of the invention.

The present invention also provides methods for preventing at least one symptom, e.g., amyloid deposition, in a subject having a disorder that would benefit from inhibiting or reducing the expression of a LECT2 gene, e.g., a LECT2-associated disease, such as amyloidosis, e.g. a LECT2 amyloidosis (ALECT2). The present invention further provides compositions comprising antisense polynucleotide agents which effect antisense inhibition of a LECT2 gene. The LECT2 gene may be within a cell, e.g., a cell within a subject, such as a human.

The following detailed description discloses how to make and use antisense polynucleotide agents to inhibit the mRNA and/or protein expression of a LECT2 gene, as well as compositions, uses, and methods for treating subjects having diseases and disorders that would benefit from inhibition and/or reduction of the expression of this gene.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "LECT2" refers to leukocyte chemotactic factor 2 (also known as leukocyte cell-derived chemotaxin 2, chondromodulin-II, chm-II or chm2). See, e.g., Yamagoe S et al. *Genomics*, 1998 Mar. 15; 48(3):324-9. LECT2 was first identified as a novel neutrophil chemotactic protein and is identical with chondromodulin II, a growth stimulator for chondrocytes and osteoblasts. The human LECT2 gene was mapped to chromosome 5q31.1-q32. Ibid.

The sequence of a human LECT2 mRNA transcript can be found at NM_002302.2 (SEQ ID NO: 1). The sequence of a macaque LECT2 mRNA can be found at NM_001194884.2 (SEQ ID NO: 2). The sequence of a mouse LECT2 mRNA can be found at NM_010702.1 and at NM_010702.2 (SEQ ID NO: 3), and the sequence of a rat LECT2 mRNA can be found at NM_001108405.1 (SEQ ID NO: 4).

The human LECT2 protein is a secreted, 16 kDa protein. The LECT2 protein is secreted by the liver. It has high sequence similarity to the chondromodulin repeat regions of the chicken myb-induced myeloid 1 protein. Polymorphism in the LECT2 gene has been associated with rheumatoid arthritis. Ibid.

LECT2 is expressed in various tissues, including the brain and stomach as well as the liver. Koshimizu, Y & Ohtomi, M. (2010) *Brain Res*. 1311:1-11. In a study using indirect immunoperoxidase staining to investigate the expression of LECT2 in normal and diseased human organs and tissues other than liver, it was found that LECT2 was generally expressed in vascular, endothelial and smooth muscle cells, adipocytes, cerebral nerve cells, apical squamous epithelia, parathyroid cells, sweat and sebaceous glandular epithelia, Hassall bodies and some mononuclear cells in immunohematopoeietic tissue. This protein was generally negative, although occasionally positively stained in osteoblasts, chondrocytes, cardiac and skeletal muscle cells, smooth mucle cells of the gastrointestinal tract, and the epithelial cells of some tissues. Nagai et al. (1998) *Pathol Int*. 48(11): 882-6.

The human LECT2 gene codes for 151 amino acids including an 18 amino acid signal peptide. The secreted protein has 133 residues. A G/A polymorphism at nucleotide 172 in exon 3 of the gene (codon change GTC to ATC) has been identified and accounts for the presence of either valine or isoleucine at position 58 of the unprocessed protein (or position 40 of the mature protein). The G allele has an overall frequency of 0.477 and a frequency range of 0.6-0.7 in individuals of European descent. See Benson, M. D. et al. (2008) *Kidney International*, 74: 218-222; Murphy, C. L. et al. (2010) *Am J Kidney Dis*, 56(6):1100-1107. Patients with LECT2 amyloidosis typically are homozygous for the G allele. Without wishing to be bound by theory, it has been suggested that replacement of the buried isoleucine (A allele) side chain with valine (G allele) could destabilize the protein and possibly account for the amyloidogenic propensity of this LECT2 variant. Murphy, C. L. et al. (2010) *Am J Kidney Dis*, 56(6):1100-1107.

As used herein, a "LECT2 amyloidosis" or "ALECT2" includes an amyloidosis involving deposits of amyloid or amyloid fibrils that contain a LECT2 protein (e.g., any polymorphic variant of a LECT2 protein) or a portion of a LECT2 protein. The LECT2 protein can be a variant (e.g., a mutant) LECT2 protein. The amyloidosis can be systemic or local. In embodiments, the LECT2 amyloidosis involves amyloid deposits in the kidney and/or liver.

The terms "antisense polynucleotide agent" "antisense compound", and "agent" as used interchangeably herein, refer to an agent comprising a single-stranded oligonucleotide that contains RNA as that term is defined herein, and which targets nucleic acid molecules encoding LECT2 (e.g., mRNA encoding LECT2 as provided in, for example, any one of SEQ ID NOs:1-4). The antisense polynucleotide agents specifically bind to the target nucleic acid molecules via hydrogen bonding (e.g., Watson-Crick, Hoogsteen or reversed Hoogsteen hydrogen bonding) and interfere with the normal function of the targeted nucleic acid (e.g., by an antisense mechanism of action). This interference with or modulation of the function of a target nucleic acid by the polynucleotide agents of the present invention is referred to as "antisense inhibition."

The functions of the target nucleic acid molecule to be interfered with may include functions such as, for example, translocation of the RNA to the site of protein translation, translation of protein from the RNA, splicing of the RNA to yield one or more mRNA species, and catalytic activity which may be engaged in or facilitated by the RNA.

In some embodiments, antisense inhibition refers to "inhibiting the expression" of target nucleic acid levels and/or target protein levels in a cell, e.g., a cell within a subject, such as a mammalian subject, in the presence of the antisense polynucleotide agent complementary to a target nucleic acid as compared to target nucleic acid levels and/or target protein levels in the absence of the antisense polynucleotide agent. For example, the antisense polynucleotide agents of the invention can inhibit translation in a stoichiometric manner by base pairing to the mRNA and physically obstructing the translation machinery, see Dias, N. et al., (2002) *Mol Cancer Ther* 1:347-355.

As used herein, "target sequence" refers to a contiguous portion of the nucleotide sequence of an mRNA molecule formed during the transcription of a LECT2 gene, including mRNA that is a product of RNA processing of a primary transcription product.

As used herein, "target nucleic acid" refers to a nucleic acid molecule to which an antisense polynucleotide agent specifically hybridizes.

As used herein, the term "specifically hybridizes" refers to an antisense polynucleotide agent having a sufficient degree of complementarity between the antisense polynucleotide agent and a target nucleic acid to induce a desired effect, while exhibiting minimal or no effects on non-target nucleic acids under conditions in which specific binding is desired, e.g., under physiological conditions in the case of in vivo assays and therapeutic treatments.

A target sequence may be from about 4-50 nucleotides in length, e.g., 8-45, 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides of the nucleotide sequence of an mRNA molecule formed during the transcription of a LECT2 gene. Ranges and lengths intermediate to the above recited ranges and lengths are also contemplated to be part of the invention.

The terms "complementary," "fully complementary" and "substantially complementary" are used herein with respect to the base matching between an antisense polynucleotide agent and a target sequence. The term"complementarity" refers to the capacity for pairing between nucleobases of a first nucleic acid and a second nucleic acid.

As used herein, an antisense polynucleotide agent that is "substantially complementary to at least part of" a messenger RNA (mRNA) refers to an antisense polynucleotide agent that is substantially complementary to a contiguous portion of the mRNA of interest (e.g., an mRNA encoding LECT2). For example, a polynucleotide is complementary to at least a part of a LECT2 mRNA if the sequence is substantially complementary to a non-interrupted portion of an mRNA encoding LECT2.

As used herein, the term "region of complementarity" refers to the region of the antisense polynucleotide agent that is substantially complementary to a sequence, for example a target sequence, e.g., a LECT2 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the antisense polynucleotide.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the nucleotides.

Complementary sequences include those nucleotide sequences of an antisense polynucleotide agent of the invention that base-pair to a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., antisense inhibition of target gene expression.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the terms "deoxyribonucleotide", "ribonucleotide" and "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of the agents featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

A "nucleoside" is a base-sugar combination. The "nucleobase" (also known as "base") portion of the nucleoside is normally a heterocyclic base moiety. "Nucleotides" are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. "Polynucleotides," also referred to as "oligonucleotides," are formed through the covalent linkage of adjacent nucleosides to one another, to form a linear polymeric oligonucleotide. Within the polynucleotide structure, the phosphate groups are commonly referred to as forming the internucleoside linkages of the polynucleotide.

In general, the majority of nucleotides of the antisense polynucleotide agents are ribonucleotides, but as described in detail herein, the agents may also include one or more non-ribonucleotides, e.g., a deoxyribonucleotide. In addition, as used in this specification, an "antisense polynucleotide agent" may include nucleotides (e.g., ribonucleotides or deoxyribonucleotides) with chemical modifications; an antisense polynucleotide agent may include substantial modifications at multiple nucleotides.

As used herein, the term "modified nucleotide" refers to a nucleotide having, independently, a modified sugar moiety, a modified internucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the antisense polynucleiotde agents of the invention include all types of modifications disclosed herein or known in the art. Any such modifications, as used in nucleotides, are encompassed by "antisense polynucleotide agent" for the purposes of this specification and claims.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in LECT2 expression; a human at risk for a disease, disorder or condition that would benefit from reduction in LECT2 expression; a human having a disease, disorder or condition that would benefit from reduction in LECT2 expression; and/or human being treated for a disease, disorder or condition that would benefit from reduction in LECT2 expression as described herein.

As used herein, the terms "treating" or "treatment" refer to a beneficial or desired result including, but not limited to, alleviation or amelioration of one or more symptoms associated with LECT2 expression; or diminishing the extent of LECT2 expression. For example, the methods featured herein, when employed to treat a LECT2 amyloidosis, may serve to inhibit amyloid deposition, to reduce or prevent one or more symptoms of the amyloidosis, or to reduce the risk or severity of associated conditions.

The term "lower" in the context of the level of LECT2 in a subject or a disease marker or symptom refers to a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more and is preferably down to a level accepted as within the range of normal for an individual without such disorder.

As used herein, "prevention" or "preventing," when used in reference to a disease, disorder or condition thereof, that would benefit from a reduction in expression of a LECT2 gene, refers to a reduction in the likelihood that a subject will develop a symptom associated with such a disease, disorder, or condition, e.g., a symptom of unwanted LECT2 expression, such as amyloid deposition.

II. Antisense Polynucleotide Agents of the Invention

The present invention provides antisense polynucleotide agents, and compositions comprising such agents, which target a LECT2 gene and inhibit the expression of the LECT2 gene. In one embodiment, the antisense polynucleotide agents inhibit the expression of a LECT2 gene in a cell, such as a cell within a subject, e.g., a mammal, such as a human having a LECT2-associated disease, e.g., amyloidosis, e.g. a LECT2 amyloidosis (ALECT2).

The antisense polynucleotide agents of the invention include a region of complementarity which is complementary to at least a part of an mRNA formed in the expression of a LECT2 gene. The region of complementarity may be about 50 nucleotides or less in length (e.g., about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4 nucleotides or less in length). Upon contact with a cell expressing the LECT2 gene, the antisense polynucleotide agent inhibits the expression of the LECT2 gene (e.g., a human, a primate, a non-primate, or a bird LECT2 gene) by at least about 10% as assayed by, for example, a PCR or branched DNA (bDNA)-based method, or by a protein-based method, such as by immunofluorescence analysis, using, for example, Western Blotting or flow cytometric techniques.

The region of complementarity between an antisense polynucleotide agent and a target sequence may be substantially complementary (e.g., there is a sufficient degree of complementarity between the antisense polynucleotide agent and a target nucleic acid to so that they specifically hybridize and induce a desired effect), but is generally fully complementary to the target sequence. The target sequence can be derived from the sequence of an mRNA formed during the expression of a LECT2 gene.

Accordingly, in one aspect, an antisense polynucleotide agent of the invention specifically hybridizes to a target nucleic acid molecule, such as the mRNA encoding LECT2, and comprises a contiguous nucleotide sequence which corresponds to the reverse complement of a nucleotide sequence of any one of SEQ ID NOs: 1-4, or a fragment of any one of SEQ ID NOs: 1-4.

In some embodiments, the antisense polynucleotide agents of the invention may be substantially complementary to the target sequence. For example, an antisense polynucleotide agent that is substantially complementary to the target sequence may include a contiguous nucleotide sequence comprising no more than 5 mismatches (e.g., no more than 1, no more than 2, no more than 3, no more than 4, or no more than 5 mismatches) when hybridizing to a target sequence, such as to the corresponding region of a nucleic acid which encodes a mammalian LECT2 mRNA. In some embodiments, the contiguous nucleotide sequence comprises no more than a single mismatch when hybridizing to the target sequence, such as the corresponding region of a nucleic acid which encodes a mammalian LECT2 mRNA.

In some embodiments, the antisense polynucleotide agents of the invention that are substantially complementary to the target sequence comprise a contiguous nucleotide sequence which is at least about 80% complementary over its entire length to the equivalent region of the nucleotide sequence of any one of SEQ ID NOs: 1-4, or a fragment of any one of SEQ ID NOs: 1-4, such as about 85%, about 86%, about 87%, about 88%, about 89%, about 90%, about % 91%, about 92%, about 93%, about 94%, about 95%, about 96%, about 97%, about 98%, or about 99% complementary.

In some embodiments, an antisense polynucleotide agent comprises a contiguous nucleotide sequence which is fully complementary over its entire length to the equivalent region of the nucleotide sequence of any one of SEQ ID NOs: 1-4 (or a fragment of any one of SEQ ID NOs: 1-4). For example, the nucleotide sequence of Oligo: A-133895.1 is fully complementary over its entire length to the equivalent region of nucleotides 12-31 of NM_002302.2 (SEQ ID NO: 1) (see, e.g., Table 3). Similarly, the nucleotide sequence of Sequence ID NO: A-133925.1 is fully complementary over its entire length to the equivalent region of nucleotides 561-581 of NM_002302.2 (SEQ ID NO: 1) (see, e.g., Table 3) and the nucleotide sequence of Sequence ID NO: A-133953.1 is fully complementary over its entire length to the equivalent region of nucleotides 870-889 of NM_002302.2 (SEQ ID NO: 1) (see, e.g., Table 3).

An antisense polynucleotide agent may comprise a contiguous nucleotide sequence of about 4 to about 50 nucleotides in length, e.g., 8-49, 8-48, 8-47, 8-46, 8-45, 8-44, 8-43, 8-42, 8-41, 8-40, 8-39, 8-38, 8-37, 8-36, 8-35, 8-34, 8-33, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 8-12, 8-11, 8-10, 8-9, 10-49, 10-48, 10-47, 10-46, 10-45, 10-44, 10-43, 10-42, 10-41, 10-40, 10-39, 10-38, 10-37, 10-36, 10-35, 10-34, 10-33, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 10-14, 10-13, 10-12, 10-11, 11-49, 11-48, 11-47, 11-46, 11-45, 11-44, 11-43, 11-42, 11-41, 11-40, 11-39, 11-38, 11-37, 11-36, 11-35, 11-34, 11-33, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 11-14, 11-13, 11-12, 12-49, 12-48, 12-47, 12-46, 12-45, 12-44, 12-43, 12-42, 12-41, 12-40, 12-39, 12-38, 12-37, 12-36, 12-35, 12-34, 12-33, 12-32, 12-31, 12-30, 12-29, 12-28, 12-27, 12-26, 12-25, 12-24, 12-23, 12-22, 12-21, 12-20, 12-19, 12-18, 12-17, 12-16, 12-15, 12-14, 12-13, 13-49, 13-48, 13-47, 13-46, 13-45, 13-44, 13-43, 13-42, 13-41, 13-40, 13-39, 13-38, 13-37, 13-36, 13-35, 13-34, 13-33, 13-32, 13-31, 13-30, 13-29, 13-28, 13-27, 13-26, 13-25, 13-24, 13-23, 13-22, 13-21, 13-20, 13-19, 13-18, 13-17, 13-16, 13-15, 13-14, 14-49, 14-48, 14-47, 14-46, 14-45, 14-44, 14-43, 14-42, 14-41, 14-40, 14-39, 14-38, 14-37, 14-36, 14-35, 14-34, 14-33, 14-32, 14-31, 14-30, 14-29, 14-28, 14-27, 14-26, 14-25, 14-24, 14-23, 14-22, 14-21, 14-20, 14-19, 14-18, 14-17, 14-16, 14-15, 15-49, 15-48, 15-47, 15-46, 15-45, 15-44, 15-43, 15-42, 15-41, 15-40, 15-39, 15-38, 15-37, 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 15-16, 16-49, 16-48, 16-47, 16-46, 16-45, 16-44, 16-43, 16-42, 16-41, 16-40, 16-39, 16-38, 16-37, 16-36, 16-35, 16-34, 16-33, 16-32, 16-31, 16-30, 16-29, 16-28, 16-27, 16-26, 16-25, 16-24, 16-23, 16-22, 16-21, 16-20, 16-19, 16-18, 16-17, 17-49, 17-48, 17-47, 17-46, 17-45, 17-44, 17-43, 17-42, 17-41, 17-40, 17-39, 17-38, 17-37, 17-36, 17-35, 17-34, 17-33, 17-32, 17-31, 17-30, 17-29, 17-28, 17-27, 17-26, 17-25, 17-24, 17-23, 17-22, 17-21, 17-20, 17-19, 17-18, 18-49, 18-48, 18-47, 18-46, 18-45, 18-44, 18-43, 18-42, 18-41, 18-40, 18-39, 18-38, 18-37, 18-36, 18-35, 18-34, 18-33, 18-32, 18-31, 18-30, 18-29, 18-28, 18-27, 18-26, 18-25, 18-24, 18-23, 18-22, 18-21, 18-20, 19-49, 19-48, 19-47, 19-46, 19-45, 19-44, 19-43, 19-42, 19-41, 19-40, 19-39, 19-38, 19-37, 19-36, 19-35, 19-34, 19-33, 19-32, 19-31, 19-30, 19-29, 19-28, 19-27, 19-26, 19-25, 19-24, 19-23, 19-22, 19-21, 19-20, 20-49, 20-48, 20-47, 20-46, 20-45, 20-44, 20-43, 20-42, 20-41, 20-40, 20-39, 20-38, 20-37, 20-36, 20-35, 20-34, 20-33, 20-32, 20-31, 20-30, 20-29, 20-28, 20-27, 20-26, 20-25, 20-24, 20-23, 20-22, 20-21, 21-49, 21-48, 21-47, 21-46, 21-45, 21-44, 21-43, 21-42, 21-41, 21-40, 21-39, 21-38, 21-37, 21-36, 21-35, 21-34, 21-33, 21-32, 21-31, 21-30, 21-29, 21-28, 21-27, 21-26, 21-25, 21-24, 21-23, 21-22, 22-49, 22-48, 22-47, 22-46, 22-45, 22-44, 22-43, 22-42, 22-41, 22-40, 22-39, 22-38, 22-37, 22-36, 22-35, 22-34, 22-33, 22-32, 22-31, 22-30, 22-29, 22-28, 22-27, 22-26, 22-25, 22-24, 22-23, 23-49, 23-48, 23-47, 23-46, 23-45, 23-44, 23-43, 23-42, 23-41, 23-40, 23-39, 23-38, 23-37, 23-36, 23-35, 23-34, 23-33, 23-32, 23-31, 23-30, 23-29, 23-28, 23-27, 23-26, 23-25, 23-24, 24-49, 24-48, 24-47, 24-46, 24-45, 24-44, 24-43, 24-42, 24-41, 24-40, 24-39, 24-38, 24-37, 24-36, 24-35, 24-34, 24-33, 24-32, 24-31, 24-30, 24-29, 24-28, 24-27, 24-26, 24-25, 25-49, 25-48, 25-47, 25-46, 25-45, 25-44, 25-43, 25-42, 25-41, 25-40, 25-39, 25-38, 25-37, 25-36, 25-35, 25-34, 25-33, 25-32, 25-31, 25-30, 25-29, 25-28, 25-27, 25-26, 26-49, 26-48, 26-47, 26-46, 26-45, 26-44, 26-43, 26-42, 26-41, 26-40, 26-39, 26-38, 26-37, 26-36, 26-35, 26-34, 26-33, 26-32, 26-31, 26-30, 26-29, 26-28, 26-27, 27-49, 27-48, 27-47, 27-46, 27-45, 27-44, 27-43, 27-42, 27-41, 27-40, 27-39, 27-38, 27-37, 27-36, 27-35, 27-34, 27-33, 27-32, 27-31, 27-30, 27-29, 27-28, 28-49, 28-48, 28-47, 28-46, 28-45, 28-44, 28-43, 28-42, 28-41, 28-40, 28-39, 28-38, 28-37, 28-36, 28-35, 28-34, 28-33, 28-32, 28-31, 28-30, 28-29, 29-49, 29-48, 29-47, 29-46, 29-45, 29-44, 29-43, 29-42, 29-41, 29-40, 29-39, 29-38, 29-37, 29-36, 29-35, 29-34, 29-33, 29-32, 29-31, 29-30, 30-49, 30-48, 30-47, 30-46, 30-45, 30-44, 30-43, 30-42, 30-41, 30-40, 30-39, 30-38, 30-37, 30-36, 30-35, 30-34, 30-33, 30-32, or 30-31 nucleotides in length, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, an antisense polynucleotide agent may comprise a contiguous nucleotide sequence of no more than 22 nucleotides, such as no more than 21 nucleotides, 20 nucleotides, 19 nucleotides, or no more than 18 nucleotides. In some embodiments the antisense polynucleotide agent of the invention comprises less than 20 nucleotides. In other embodiments, the antisense polynucleotide agents of the invention comprise 20 nucleotides.

In one aspect, an antisense polynucleotide agent of the invention includes a sequence selected from the group of sequences provided in Table 3. It will be understood that, although some of the sequences in Table 3 are described as modified and/or conjugated sequences, an antisense polynucleotide agent of the invention, may also comprise any one of the sequences set forth in Table 3 that is un-modified, un-conjugated, and/or modified and/or conjugated differently than described therein.

By virtue of the nature of the nucleotide sequences provided in Table 3, antisense polynucleotide agents of the invention may include one of the sequences of Table 3 minus only a few nucleotides on one or both ends and yet remain similarly effective as compared to the antisense polynucleotide agents described above. Hence, antisense polynucleotide agents having a sequence of at least 4, 5, 6, 7, 8, 9, 10, 11, 12, 13, 14, 15, 16, 17, 18, 19, 20, or more contiguous nucleotides derived from one of the sequences of Table 3 and differing in their ability to inhibit the expression of a LECT2 gene by not more than about 5, 10, 15, 20, 25, or 30% inhibition from an antisense polynucleotide agent comprising the full sequence, are contemplated to be within the scope of the present invention.

In addition, the antisense polynucleotide agents provided in Table 3 identify a region(s) in a LECT2 transcript that is susceptible to antisense inhibition (e.g., the regions encompassed by the start and end positions relative to NM_002302.2 in Table 3). As such, the present invention further features antisense polynucleotide agents that target within one of these sites. As used herein, an antisense polynucleotide agent is said to target within a particular site of an RNA transcript if the antisense polynucleotide agent promotes antisense inhibition of the target at that site. Such an antisense polynucleotide agent will generally include at least about 15 contiguous nucleotides from one of the sequences provided in Table 3 coupled to additional nucleotide sequences taken from the region contiguous to the selected sequence in a LECT2 gene.

While a target sequence is generally about 4-50 nucleotides in length, there is wide variation in the suitability of particular sequences in this range for directing antisense inhibition of any given target RNA. Various software packages and the guidelines set out herein provide guidance for the identification of optimal target sequences for any given gene target, but an empirical approach can also be taken in which a "window" or "mask" of a given size (as a non-limiting example, 20 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an antisense polynucleotide agent, mediate the best inhibition of target gene expression. Thus, while the sequences identified, for example, in Table 3 represent effective target sequences, it is contemplated that further optimization of antisense inhibition efficiency can be achieved by progressively "walking the window" one nucleotide upstream or downstream of the given sequences to identify sequences with equal or better inhibition characteristics.

Further, it is contemplated that for any sequence identified, e.g., in Table 3, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of antisense polynucleotide agents based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in length, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

III. Modified Antisense Polynucleotide Agents of the Invention

In one embodiment, the nucleotides of an antisense polynucleotide agent are un-modified, and do not comprise, e.g., chemical modifications and/or conjugations known in the art and described herein. In another embodiment, at least one of the nucleotides of an antisense polynucleotide agent of the invention is chemically modified to enhance stability or other beneficial characteristics. In certain embodiments of the invention, substantially all of the nucleotides of an antisense polynucleotide agent of the invention are modified. In other embodiments of the invention, all of the nucleotides of an antisense polynucleotide agent of the invention are modified. Antisense polynucleotide agents of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by standard methods known in the art as further discussed below, e.g., solution-phase or solid-phase organic synthesis or both, e.g., by use of an automated DNA synthesizer, such as are commercially available from, for example, Biosearch, Applied Biosystems, Inc. Well-established methods for the synthesis and/or modification of the nucleic acids featured in the invention are described in, for example, "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages.

Specific examples of modified nucleotides useful in the embodiments described herein include, but are not limited to nucleotides containing modified backbones or no natural internucleoside linkages. Nucleotides having modified backbones include, among others, those that do not have a phosphorus atom in the backbone. For the purposes of this specification, and as sometimes referenced in the art, modified nucleotides that do not have a phosphorus atom in their internucleoside backbone can also be considered to be oligonucleosides. In some embodiments, a modified antisense polynucleotide agent will have a phosphorus atom in its internucleoside backbone.

Modified nucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160, 109; 6,169,170; 6,172,209; 6, 239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and U.S. Pat. RE39464, the entire contents of each of which are hereby incorporated herein by reference.

Modified nucleotide backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable nucleotide mimetics are contemplated for use in antisense polynucleotide agents, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the antisense polynucleotide agents of the invention are described in, for example, in Nielsen et al., *Science*, 1991, 254, 1497-1500.

Some embodiments featured in the invention include polynucleotides with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489, 677, and the amide backbones of the above-referenced U.S. Pat. No. 5,602,240. In some embodiments, the antisense polynucleotide agents featured herein have morpholino backbone structures of the above-referenced U.S. Pat. No. 5,034,506.

Modified nucleotides can also contain one or more modified or substituted sugar moieties. The antisense polynucleotide agents featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10.

In other embodiments, antisense polynucleotide agents include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an antisense polynucleotide, or a group for improving the pharmacodynamic properties of an antisense polynucleotide agent, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on a nucleotide of an antisense polynucleotide agent, particularly the 3' position of the sugar on the 3' terminal nucleotide. Antisense polynucleotide agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

Additional nucleotides having modified or substituted sugar moieties for use in the polynucleotide agents of the invention include nucleotides comprising a bicyclic sugar. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an antisense polynucleotide agent may include one or more locked nucleic acids. A "locked nucleic acid" ("LNA") is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to santisense polynucleotide agents has been shown to increase santisense polynucleotide agent stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g.,U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

In one particular embodiment of the invention, an antisense polynucleotide agent can include one or more constrained ethyl nucleotides. As used herein, a "constrained ethyl nucleotide" or "cEt" is a locked nucleic acid comprising a bicyclic sugar moiety comprising a 4'-CH(CH$_3$)—O-2' bridge. In one embodiment, a constrained ethyl nucleotide is in an S conformation and is referred to as an "S-constrained ethyl nucleotide" or "S-cEt."

Modified nucleotides included in the antisense polynucleotide agents of the invention can also contain one or more sugar mimetics. For example, the antisense polynucleotide agent may include a "modified tetrahydropyran nucleotide" or "modified THP nucleotide." A "modified tetrahydropyran nucleotide" has a six-membered tetrahydropyran "sugar" substituted in for the pentofuranosyl residue in normal nucleotides (a sugar surrogate). Modified THP nucleotides include, but are not limited to, what is referred to in the art as hexitol nucleic acid (HNA), anitol nucleic acid (ANA), manitol nucleic acid (MNA) (see, e.g., Leumann, *Bioorg. Med. Chem.*, 2002, 10, 841-854), or fluoro HNA (F-HNA).

In some embodiments of the invention, sugar surrogates comprise rings having more than 5 atoms and more than one heteroatom. For example nucleotides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). Morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH2-O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica*, Section F: Structural Biology and Crystallization Communications, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety).

An antisense polynucleotide agent can also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine.

Further nucleobases include those disclosed in U.S. Pat. No. 3,687,808, those disclosed in "Modified Nucleosides in Biochemistry," Biotechnology and Medicine, Herdewijn, P. ed. Wiley-VCH, 2008; those disclosed in *The Concise Encyclopedia Of Polymer Science And Engineering*, pages 858-859, Kroschwitz, J. L, ed. John Wiley & Sons, 1990, these disclosed by Englisch et al., *Angewandte Chemie, International Edition*, 1991, 30, 613, and those disclosed by Sanghvi, Y S., Chapter 15, *antisense polynucleotide agent Research and Applications*, pages 289-302, Crooke, S. T. and Lebleu, B., Ed., CRC Press, 1993. Certain of these nucleobases are particularly useful for increasing the binding affinity of the agents featured in the invention. These include κ-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., *antisense polynucleotide agent Research and Applications*, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification. Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Additional modification which may potentially stabilize the ends of antisense polynucleotide agents can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3''-phosphate, inverted base dT(idT) and others. Disclosure of this modification can be found in US Patent Publication No. 2012/0142101.

Any of the antisense polynucleotide agents of the invention may be optionally conjugated with a GalNAc derivative ligand, as described in Section IV, below.

As described in more detail below, an agent that contains conjugations of one or more carbohydrate moieties to an antisense polynucleotide agent can optimize one or more properties of the agent. In many cases, the carbohydrate moiety will be attached to a modified subunit of the antisense polynucleotide agent. For example, the ribose sugar of one or more ribonucleotide subunits of an agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The antisense polynucleotide agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the antisense polynucleotide agent for use in the methods of the invention is an agent selected from the group of agents listed in Table 3. These agents may further comprise a ligand, as described in Section IV, below.

A. Antisense Polynucleotide Agents Comprising Motifs

In certain embodiments of the invention, at least one of the contiguous nucleotides of the antisense polynucleotide agents of the invention may be a modified nucleotide. In one embodiment, the modified nucleotide comprises one or more modified sugars. In other embodiments, the modified nucleotide comprises one or more modified nucleobases. In yet other embodiments, the modified nucleotide comprises one or more modified internucleoside linkages. In some embodiments, the modifications (sugar modifications, nucleobase modifications, and/or linkage modifications) define a pattern or motif. In one embodiment, the patterns of modifications of sugar moieties, internucleoside linkages, and nucleobases are each independent of one another.

Antisense polynucleotide agents having modified oligonucleotides arranged in patterns, or motifs may, for example, confer to the agents properties such as enhanced inhibitory activity, increased binding affinity for a target nucleic acid, or resistance to degradation by in vivo nucleases. For example, such agents may contain at least one region modified so as to confer increased resistance to nuclease degradation, increased cellular uptake, increased binding affinity for the target nucleic acid, and/or increased inhibitory activity. A second region of such agents may optionally serve as a substrate for the cellular endonuclease RNase H, which cleaves the RNA strand of an RNA:DNA duplex.

An exemplary antisense polynucleotide agent having modified oligonucleotides arranged in patterns, or motifs is a gapmer. In a "gapmer", an internal region or "gap" having a plurality of linked nucleotides that supports RNaseH cleavage is positioned between two external flanking regions or "wings" having a plurality of linked nucleotides that are chemically distinct from the linked nucleotides of the internal region. The gap segment generally serves as the substrate for endonuclease cleavage, while the wing segments comprise modified nucleotides.

The three regions of a gapmer motif (the 5'-wing, the gap, and the 3'-wing) form a contiguous sequence of nucleotides and may be described as "X—Y—Z", wherein "X" represents the length of the 5-wing, "Y" represents the length of the gap, and "Z" represents the length of the 3'-wing. In one embodiment, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different.

In certain embodiments, the regions of a gapmer are differentiated by the types of modified nucleotides in the region. The types of modified nucleotides that may be used to differentiate the regions of a gapmer, in some embodiments, include β-D-ribonucleotides, β-D-deoxyribonucleotides, 2'-modified nucleotides, e.g., 2'-modified nucleotides (e.g., 2'-MOE, and 2'-O—CH3), and bicyclic sugar modified nucleotides (e.g., those having a 4'-(CH2)n-O-2' bridge, where n=1 or n=2).

In one embodiment, at least some of the modified nucleotides of each of the wings may differ from at least some of the modified nucleotides of the gap. For example, at least some of the modified nucleotides of each wing that are closest to the gap (the 3'-most nucleotide of the 5'-wing and the 5'-most nucleotide of the 3-wing) differ from the modified nucleotides of the neighboring gap nucleotides, thus defining the boundary between the wings and the gap. In certain embodiments, the modified nucleotides within the gap are the same as one another. In certain embodiments, the gap includes one or more modified nucleotides that differ from the modified nucleotides of one or more other nucleotides of the gap.

The length of the 5'-wing (X) of a gapmer may be 1 to 6 nucleotides in length, e.g., 2 to 6, 2 to 5, 3 to 6, 3 to 5, 1 to 5, 1 to 4, 1 to 3, 2 to 4 nucleotides in length, e.g., 1, 2, 3, 4, 5, or 6 nucleotides in length.

The length of the 3'-wing (Z) of a gapmer may be 1 to 6 nucleotides in length, e.g., 2 to 6, 2-5, 3 to 6, 3 to 5, 1 to 5, 1 to 4, 1 to 3, 2 to 4 nucleotides in length, e.g., 1, 2, 3, 4, 5, or 6 nucleotides in length.

The length of the gap (Y) of a gapmer may be 5 to 14 nucleotides in length, e.g., 5 to 13, 5 to 12, 5 to 11, 5 to 10, 5 to 9, 5 to 8, 5 to 7, 5 to 6, 6 to 14, 6 to 13, 6 to 12, 6 to 11, 6 to 10, 6 to 9, 6 to 8, 6 to 7, 7 to 14, 7 to 13, 7 to 12, 7 to 11, 7 to 10, 7 to 9, 7 to 8, 8 to 14, 8 to 13, 8 to 12, 8 to 11, 8 to 10, 8 to 9, 9 to 14, 9 to 13, 9 to 12, 9 to 11, 9 to 10, 10 to 14, 10 to 13, 10 to 12, 10 to 11, 11 to 14, 11 to 13, 11 to 12, 12 to 14, 12 to 13, or 13 to 14 nucleotides in length, e.g., 5, 6, 7, 8, 9, 10, 11, 12, 13, or 14 nucleotides in length.

In some embodiments of the invention X consists of 2, 3, 4, 5 or 6 nucleotides, Y consists of 7, 8, 9, 10, 11, or 12 nucleotides, and Z consists of 2, 3, 4, 5 or 6 nucleotides. Such gapmers include (X—Y—Z) 2-7-2, 2-7-3, 2-7-4, 2-7-5, 2-7-6, 3-7-2, 3-7-3, 3-7-4, 3-7-5, 3-7-6, 4-7- 3, 4-7-4, 4-7-5, 4-7-6, 5-7-3, 5-7-4, 5-7-5, 5-7-6, 6-7-3, 6-7-4, 6-7-5, 6-7-6, 3-7-3, 3-7-4, 3-7-5, 3-7-6, 4-7-3, 4-7-4, 4-7-5, 4-7-6, 5-7-3, 5-7-4, 5-7-5, 5-7-6, 6-7-3, 6-7-4, 6-7-5, 6-7-6, 2-8-2, 2-8-3, 2-8-4, 2-8-5, 2-8-6, 3-8-2, 3-8-3, 3-8-4, 3-8-5, 3-8-6, 4-8-3, 4-8-4, 4-8-5, 4-8-6, 5-8-3, 5-8-4, 5-8-5, 5-8-6, 6-8-3, 6-8-4, 6-8-5, 6-8-6, 2-9-2, 2-9-3, 2-9-4, 2-9-5, 2-9-6, 3-9-2, 3-9-3, 3-9-4, 3-9-5, 3-9-6, 4-9-3, 4-9-4, 4-9-5, 4-9-6, 5-9-3, 5-9-4, 5-9-5, 5-9-6, 6-9-3, 6-9-4, 6-9-5, 6-9-6, 2-10-2, 2-10-3, 2-10-4, 2-10-5, 2-10-6, 3-10-2, 3-10-3, 3-10-4, 3-10-5, 3-10-6, 4-10-3, 4-10-4, 4-10-5, 4-10-6, 5-10-3, 5-10-4, 5-10-5, 5-10-6, 6-10-3, 6-10-4, 6-10-5, 6-10-6, 2-11-2, 2-11-3, 2-11-4, 2-11-5, 2-11-6, 3-11-2, 3-11-3, 3-11-4, 3-11-5, 3-11-6, 4-11-3, 4-11-4, 4-11-5, 4-11-6, 5-11-3, 5-11-4, 5-11-5, 5-11-6, 6-11-3, 6-11-4, 6-11-5, 6-11-6, 2-12-2, 2-12-3, 2-12-4, 2-12-5, 2-12-6, 3-12-2, 3-12-3, 3-12-4, 3-12-5, 3-12-6, 4-12-3, 4-12-4, 4-12-5, 4-12-6, 5-12-3, 5-12-4, 5-12-5, 5-12-6, 6-12-3, 6-12-4, 6-12-5, or 6-12-6.

In some embodiments of the invention, antisense polynucleotide agents targeting LECT2 include a 5-10-5 gapmer motif. In other embodiments of the invention, antisense polynucleotide agents targeting LECT2 include a 4-10-4 gapmer motif. In another embodiment of the invention, antisense polynucleotide agents targeting LECT2 include a 3-10-3 gapmer motif. In yet other embodiments of the invention, antisense polynucleotide agents targeting LECT2 include a 2-10-2 gapmer motif.

The 5'-wing and/or 3'-wing of a gapmer may independently include 1-6 modified nucleotides, e.g., 1, 2, 3, 4, 5, or 6 modified nucleotides.

In some embodiment, the 5'-wing of a gapmer includes at least one modified nucleotide. In one embodiment, the 5'-wing of a gapmer comprises at least two modified nucleotides. In another embodiment, the 5'-wing of a gapmer comprises at least three modified nucleotides. In yet another embodiment, the 5'-wing of a gapmer comprises at least four modified nucleotides. In another embodiment, the 5'-wing of a gapmer comprises at least five modified nucleotides. In certain embodiments, each nucleotide of the 5'-wing of a gapmer is a modified nucleotide.

In some embodiments, the 3'-wing of a gapmer includes at least one modified nucleotide. In one embodiment, the 3'-wing of a gapmer comprises at least two modified nucleotides. In another embodiment, the 3'-wing of a gapmer comprises at least three modified nucleotides. In yet another embodiment, the 3'-wing of a gapmer comprises at least four modified nucleotides. In another embodiment, the 3'-wing of a gapmer comprises at least five modified nucleotides. In certain embodiments, each nucleotide of the 3'-wing of a gapmer is a modified nucleotide.

In certain embodiments, the regions of a gapmer are differentiated by the types of sugar moieties of the nucleotides. In one embodiment, the nucleotides of each distinct region comprise uniform sugar moieties. In other embodiments, the nucleotides of each distinct region comprise different sugar moieties. In certain embodiments, the sugar nucleotide modification motifs of the two wings are the same as one another. In certain embodiments, the sugar nucleotide modification motifs of the 5'-wing differs from the sugar nucleotide modification motif of the 3'-wing.

The 5'-wing of a gapmer may include 1-6 modified nucleotides, e.g., 1, 2, 3, 4, 5, or 6 modified nucleotides.

In one embodiment, at least one modified nucleotide of the 5'-wing of a gapmer is a bicyclic nucleotide, such as a constrained ethyl nucleotide, or an LNA. In another embodiment, the 5'-wing of a gapmer includes 2, 3, 4, or 5 bicyclic nucleotides. In some embodiments, each nucleotide of the 5'-wing of a gapmer is a bicyclic nucleotide.

In one embodiment, the 5'-wing of a gapmer includes at least 1, 2, 3, 4, or 5 constrained ethyl nucleotides. In some embodiments, each nucleotide of the 5'-wing of a gapmer is a constrained ethyl nucleotide.

In one embodiment, the 5'-wing of a gapmer comprises at least one LNA nucleotide. In another embodiment, the 5'-wing of a gapmer includes 2, 3, 4, or 5 LNA nucleotides. In other embodiments, each nucleotide of the 5'-wing of a gapmer is an LNA nucleotide.

In certain embodiments, at least one modified nucleotide of the 5'-wing of a gapmer is a non-bicyclic modified nucleotide, e.g., a 2'-substituted nucleotide. A "2'-substituted nucleotide" is a nucleotide comprising a modification at the 2'-position which is other than H or OH, such as a 2'-OMe nucleotide, or a 2'-MOE nucleotide. In one embodiment, the 5'-wing of a gapmer comprises 2, 3, 4, or 5 2'-substituted nucleotides. In one embodiment, each nucleotide of the 5'-wing of a gapmer is a 2'-substituted nucleotide.

In one embodiment, the 5'-wing of a gapmer comprises at least one 2'-OMe nucleotide. In one embodiment, the 5'-wing of a gapmer comprises at least 2, 3, 4, or 5 2'-OMe nucleotides. In one embodiment, each of the nucleotides of the 5'-wing of a gapmer comprises a 2'-OMe nucleotide.

In one embodiment, the 5'-wing of a gapmer comprises at least one 2'-MOE nucleotide. In one embodiment, the 5'-wing of a gapmer comprises at least 2, 3, 4, or 5 2'-MOE nucleotides. In one embodiment, each of the nucleotides of the 5'-wing of a gapmer comprises a 2'-MOE nucleotide.

In certain embodiments, the 5'-wing of a gapmer comprises at least one 2'-deoxynucleotide. In certain embodiments, each nucleotide of the 5'-wing of a gapmer is a 2'-deoxynucleotide. In a certain embodiments, the 5'-wing of a gapmer comprises at least one ribonucleotide. In certain embodiments, each nucleotide of the 5'-wing of a gapmer is a ribonucleotide.

The 3'-wing of a gapmer may include 1-6 modified nucleotides, e.g., 1, 2, 3, 4, 5, or 6 modified nucleotides.

In one embodiment, at least one modified nucleotide of the 3'-wing of a gapmer is a bicyclic nucleotide, such as a constrained ethyl nucleotide, or an LNA. In another embodiment, the 3'-wing of a gapmer includes 2, 3, 4, or 5 bicyclic nucleotides. In some embodiments, each nucleotide of the 3'-wing of a gapmer is a bicyclic nucleotide.

In one embodiment, the 3'-wing of a gapmer includes at least one constrained ethyl nucleotide. In another embodiment, the 3'-wing of a gapmer includes 2, 3, 4, or 5 constrained ethyl nucleotides. In some embodiments, each nucleotide of the 3'-wing of a gapmer is a constrained ethyl nucleotide.

In one embodiment, the 3'-wing of a gapmer comprises at least one LNA nucleotide. In another embodiment, the 3'-wing of a gapmer includes 2, 3, 4, or 5 LNA nucleotides. In other embodiments, each nucleotide of the 3'-wing of a gapmer is an LNA nucleotide.

In certain embodiments, at least one modified nucleotide of the 3'-wing of a gapmer is a non-bicyclic modified nucleotide, e.g., a 2'-substituted nucleotide. In one embodiment, the 3'-wing of a gapmer comprises 2, 3, 4, or 5 2'-substituted nucleotides. In one embodiment, each nucleotide of the 3'-wing of a gapmer is a 2'-substituted nucleotide.

In one embodiment, the 3'-wing of a gapmer comprises at least one 2'-OMe nucleotide. In one embodiment, the 3'-wing of a gapmer comprises at least 2, 3, 4, or 5 2'-OMe nucleotides. In one embodiment, each of the nucleotides of the 3'-wing of a gapmer comprises a 2'-OMe nucleotide.

In one embodiment, the 3'-wing of a gapmer comprises at least one 2'-MOE nucleotide. In one embodiment, the 3'-wing of a gapmer comprises at least 2, 3, 4, or 5 2'-MOE nucleotides. In one embodiment, each of the nucleotides of the 3'-wing of a gapmer comprises a 2'-MOE nucleotide.

In certain embodiments, the 3'-wing of a gapmer comprises at least one 2'-deoxynucleotide. In certain embodiments, each nucleotide of the 3'-wing of a gapmer is a 2'-deoxynucleotide. In a certain embodiments, the 3'-wing of a gapmer comprises at least one ribonucleotide. In certain embodiments, each nucleotide of the 3'-wing of a gapmer is a ribonucleotide.

The gap of a gapmer may include 5-14 modified nucleotides, e.g., 5, 6, 7, 8, 9, 10, 11, 12, 13, or 14 modified nucleotides.

In one embodiment, the gap of a gapmer comprises at least one 5-methylcytosine. In one embodiment, the gap of a gapmer comprises at least 2, 3, 4, 5, 6, 7, 8, 9, 10, 11, 12, or 13 5-methylcytosines. In one embodiment, all of the nucleotides of the the gap of a gapmer are 5-methylcytosines.

In one embodiment, the gap of a gapmer comprises at least one 2'-deoxynucleotide. In one embodiment, the gap of a gapmer comprises at least 2, 3, 4, 5, 6, 7, 8, 9, 10, 11, 12, or 13 2'-deoxynucleotides. In one embodiment, all of the nucleotides of the the gap of a gapmer are 2'-deoxynucleotides.

A gapmer may include one or more modified internucleotide linkages. In some embodiments, a gapmer includes one or more phosphodiester internucleotide linkages. In other embodiments, a gapmer includes one or more phosphorothioate internucleotide linkages.

In one embodiment, each nucleotide of a 5'-wing of a gapmer are linked via a phosphorothioate internucleotide linkage. In another embodiment, each nucleotide of a 3'-wing of a gapmer are linked via a phosphorothioate internucleotide linkage. In yet another embodiment, each nucleotide of a gap segment of a gapmer is linked via a phosphorothioate internucleotide linkage. In one embodiment, all of the nucleotides in a gapmer are linked via phosphorothioate internucleotide linkages.

In one embodiment, an antisense polynucleotide agent targeting a LECT2 gene comprises a gap segment of ten 2'-deoxyribonucleotides positioned immediately adjacent to and between a 5'-wing segment comprising five nucleotides and a 3'-wing segment comprising 5 nucleotides.

In another embodiment, an antisense polynucleotide agent targeting a LECT2 gene comprises a gap segment of ten 2'-deoxyribonucleotides positioned immediately adjacent to and between a 5'-wing segment comprising four nucleotides and a 3'-wing segment comprising four nucleotides.

In another embodiment, an antisense polynucleotide agent targeting a LECT2 gene comprises a gap segment of ten 2'-deoxyribonucleotides positioned immediately adjacent to and between a 5'-wing segment comprising three nucleotides and a 3'-wing segment comprising three nucleotides.

In another embodiment, an antisense polynucleotide agent targeting a LECT2 gene comprises a gap segment of ten 2'-deoxyribonucleotides positioned immediately adjacent to and between a 5'-wing segment comprising two nucleotides and a 3'-wing segment comprising two nucleotides.

In one embodiment, each nucleotide of a 5-wing flanking a gap segment of 10 2'-deoxyribonucleotides comprises a modified nucleotide. In another embodiment, each nucleotide of a 3-wing flanking a gap segment of 10 2'-deoxyribonucleotides comprises a modified nucleotide. In one embodiment, each of the modified 5'-wing nucleotides and each of the modified 3'-wing nucleotides comprise a 2'-sugar modification. In one embodiment, the 2'-sugar modification is a 2'-OMe modification. In another embodiment, the 2'-sugar modification is a 2'-MOE modification. In one embodiment, each of the modified 5'-wing nucleotides and each of the modified 3'-wing nucleotides comprise a bicyclic nucleotide. In one embodiment, the bicyclic nucleotide is a constrained ethyl nucleotide. In another embodiment, the bicyclic nucleotide is an LNA nucleotide. In one embodiment, each cytosine in an antisense polynucleotide agent targeting a LECT2 gene is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising five nucleotides comprising a 2'OMe modification and a 3'-wing segment comprising five nucleotides comprising a 2'OMe modification, wherein each internucleotide linkage of the agent is a phosphorothioate linkage. In one embodiment, each cytosine of the agent is a 5-methylcytosine. In one embodiment, the agent further comprises a ligand.

In one embodiment, an antisense polynucleotide agent targeting a LECT2 gene comprises a gap segment of ten 2'-deoxyribonucleotides positioned immediately adjacent to and between a 5'-wing segment comprising five nucleotides comprising a 2'MOE modification and a 3'-wing segment comprising five nucleotides comprising a 2'MOE modification, wherein each internucleotide linkage of the agent is a phosphorothioate linkage. In one embodiment, each cytosine of the agent is a 5-methylcytosine. In one embodiment, the agent further comprises a ligand.

In one embodiment, an antisense polynucleotide agent targeting a LECT2 gene comprises a gap segment of ten 2'-deoxyribonucleotides positioned immediately adjacent to and between a 5'-wing segment comprising five constrained ethyl nucleotides and a 3'-wing segment comprising five constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising five LNA nucleotides and a 3'-wing segment comprising five LNA nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising four nucleotides comprising a 2'OMe modification and a 3'-wing segment comprising four nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising four nucleotides comprising a 2'MOE modification and a 3'-wing segment comprising four nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising four constrained ethyl nucleotides and a 3'-wing segment comprising four constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising four LNA nucleotides and a 3'-wing segment comprising four LNA nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising three nucleotides comprising a 2'OMe modification and a 3'-wing segment comprising three nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising three nucleotides comprising a 2'MOE modification and a 3'-wing segment comprising three nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising three constrained ethyl nucleotides and a 3'-wing segment comprising three constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising three LNA nucleotides and a 3'-wing segment comprising three LNA nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising two nucleotides comprising a 2'OMe modification and a 3'-wing segment comprising two nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising two nucleotides comprising a 2'MOE modification and a 3'-wing segment comprising two nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising two constrained ethyl nucleotides and a 3'-wing segment comprising two constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a LECT2 gene comprises a gap segment of ten 2'-deoxyribonucleotides positioned immediately adjacent to and between a 5'-wing segment comprising two LNA nucleotides and a 3'-wing segment comprising two LNA nucleotides, wherein each internucleotide linkage of the agent is a phosphorothioate linkage. In one embodiment, each cytosine of the agent is a 5-methylcytosine.

Further gapmer designs suitable for use in the agents, compositions, and methods of the invention are disclosed in, for example, U.S. Pat. Nos. 7,687,617 and 8,580,756; U.S. Patent Publication Nos. 20060128646, 20090209748, 20140128586, 20140128591, 20100210712, and 20080015162A1; and International Publication No. WO 2013/159108, the entire content of each of which are incorporated herein by reference.

IV. Antisense Polynucleotide Agents Conjugated to Ligands

Another modification of the polynucleotide agents of the invention involves chemically linking to the agent one or more ligands, moieties or conjugates that enhance the activity, cellular distribution or cellular uptake of the antisense polynucleotide agent. Such moieties include but are not limited to lipid moieties such as a cholesterol moiety (Letsinger et al., *Proc. Natl. Acad. Sci. USA*, 1989, 86: 6553-6556), cholic acid (Manoharan et al., *Biorg. Med. Chem. Let.*, 1994, 4:1053-1060), a thioether, e.g., beryl-S-tritylthiol (Manoharan et al., *Ann. N.Y. Acad. Sci.*, 1992, 660:306-309; Manoharan et al., *Biorg. Med. Chem. Let.*, 1993, 3:2765-2770), a thiocholesterol (Oberhauser et al., *Nucl. Acids Res.*, 1992, 20:533-538), an aliphatic chain, e.g., dodecandiol or undecyl residues (Saison-Behmoaras et al., *EMBO J*, 1991, 10:1111-1118; Kabanov et al., *FEBS Lett.*, 1990, 259:327-330; Svinarchuk et al., *Biochimie*, 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.*, 1995, 36:3651-3654; Shea et al., *Nucl. Acids Res.*, 1990, 18:3777-3783), a polyamine or a polyethylene glycol chain (Manoharan et al., *Nucleosides & Nucleotides*, 1995, 14:969-973), or adamantane acetic acid (Manoharan et al., *Tetrahedron Lett.*, 1995, 36:3651-3654), a palmityl moiety (Mishra et al., *Biochim. Biophys. Acta*, 1995, 1264:229-237), or an octadecylamine or hexylamino-carbonyloxycholesterol moiety (Crooke et al., *J. Pharmacol. Exp. Ther.*, 1996, 277:923-937).

In one embodiment, a ligand alters the distribution, targeting or lifetime of an antisense polynucleotide agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in hybridization of an antisense polynucleotide agent to the targeted mRNA.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the antisense polynucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an antisense polynucleotide agent as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated polynucleotides of the invention may be synthesized by the use of a polynucleotide that bears a pendant reactive functionality, such as that derived from the attachment of a linking molecule onto the oligonucleotide (described below). This reactive polynucleotide may be reacted directly with commercially-available ligands, ligands that are synthesized bearing any of a variety of protecting groups, or ligands that have a linking moiety attached thereto.

The polynucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other polynucleotides, such as the phosphorothioates and alkylated derivatives.

In the ligand-conjugated polynucleotides and ligand-molecule bearing sequence-specific linked nucleosides of the present invention, the polynucleotides and polynucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the polynucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to antisense polynucleotide agents can affect pharmacokinetic distribution of the agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVLLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the Drosophila Antennapedia protein (RQIKIWFQNRRMKWKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an antisens epolynucleotide agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an antisense polynucleotide agent further comprises a carbohydrate. The carbohydrate conjugated agents are advantageous for the in vivo delivery of nucleic acids, as well as compositions suitable for in vivo therapeutic use, as described herein (see, e.g., Prakash, et al. (2014) Nuc Acid Res doi 10.1093/nar/gku531). As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In some embodiments, the GalNAc conjugate is

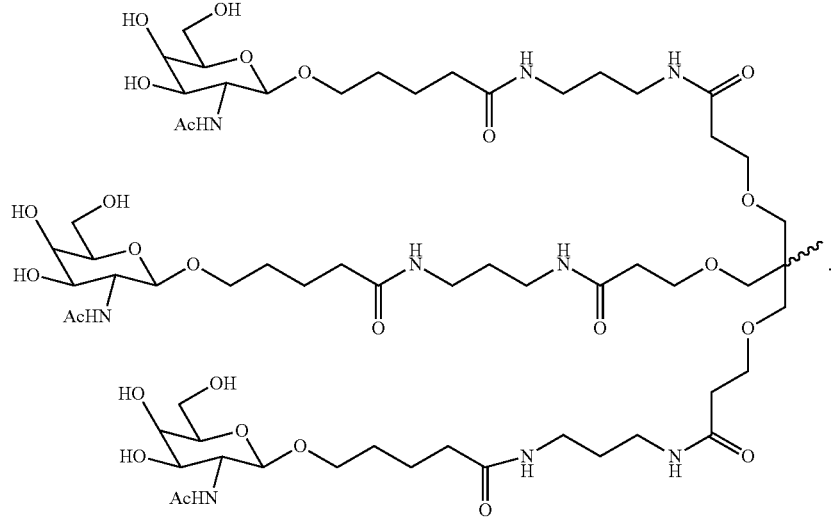 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Formula II

In some embodiments, a carbohydrate conjugate for use in the compositions and methods of the invention is selected from the group consisting of:
Formula II
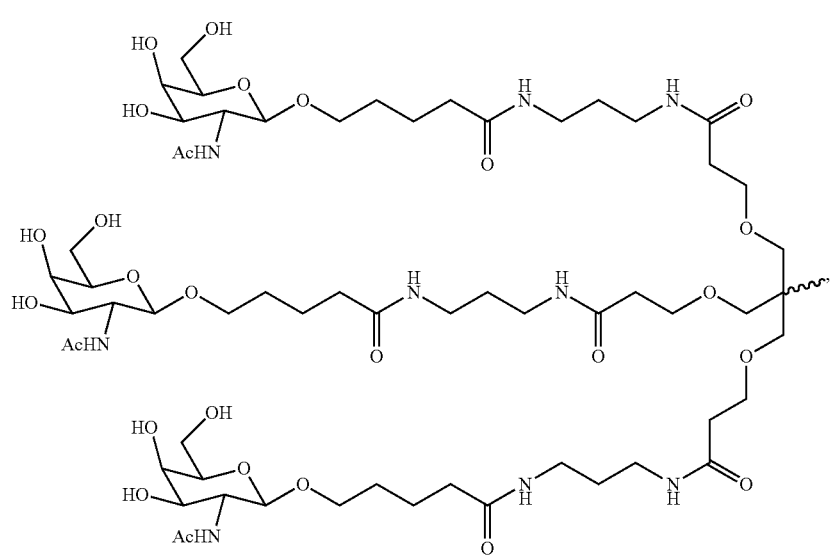
Formula III
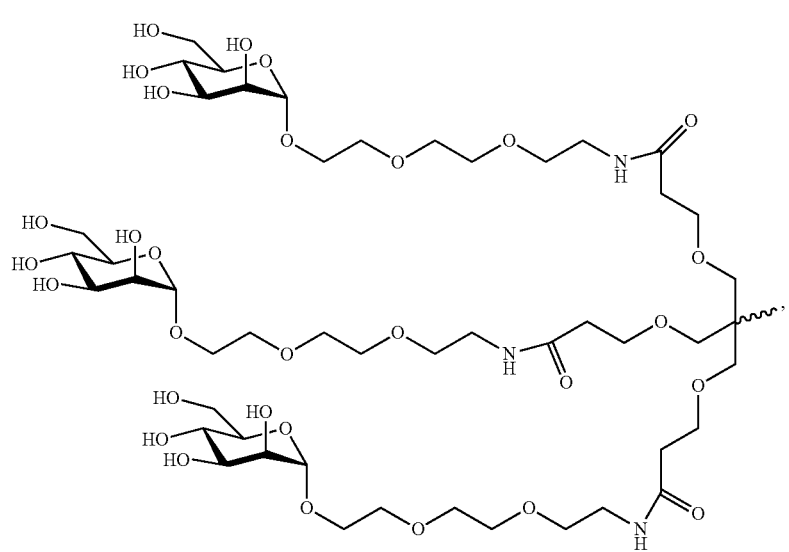
Formula IV
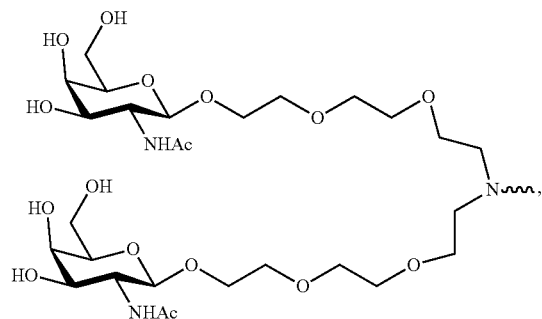
Formula V
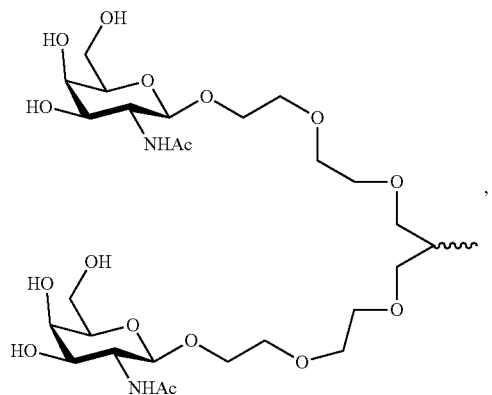

Formula VI
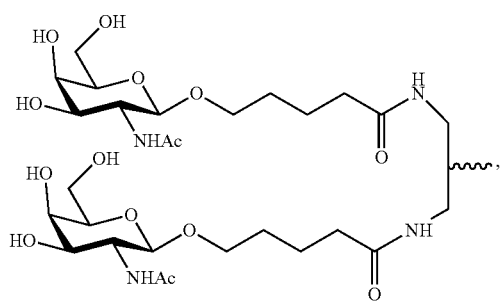
Formula VII
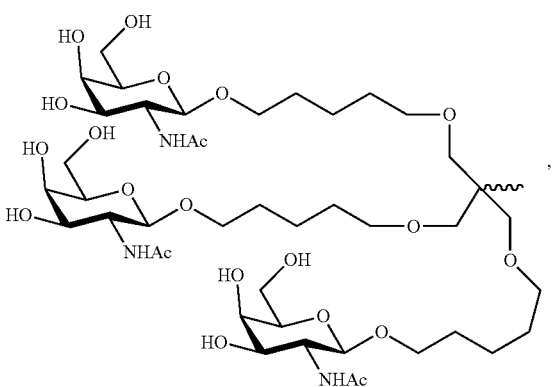
Formula VIII
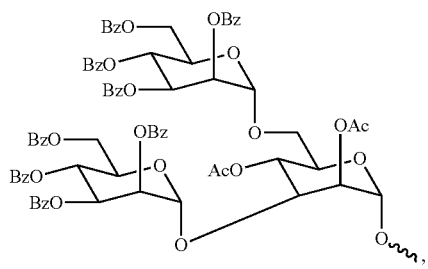
Formula IX
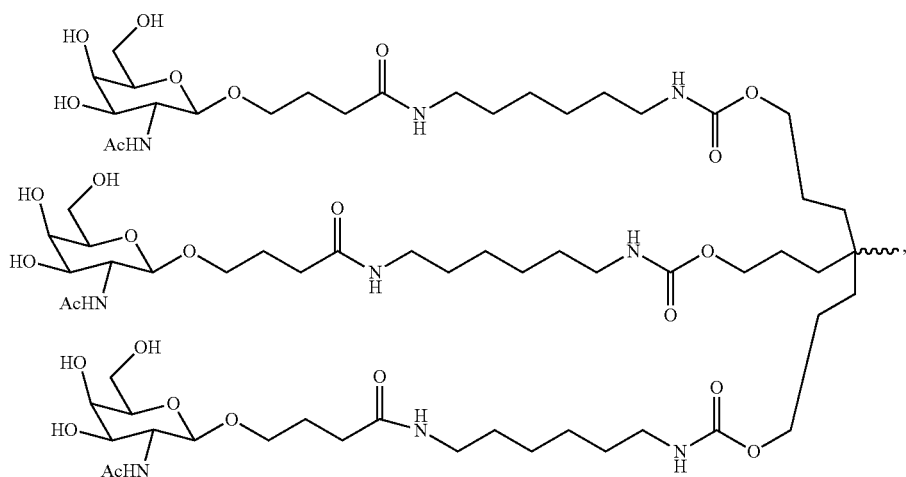
Formula X
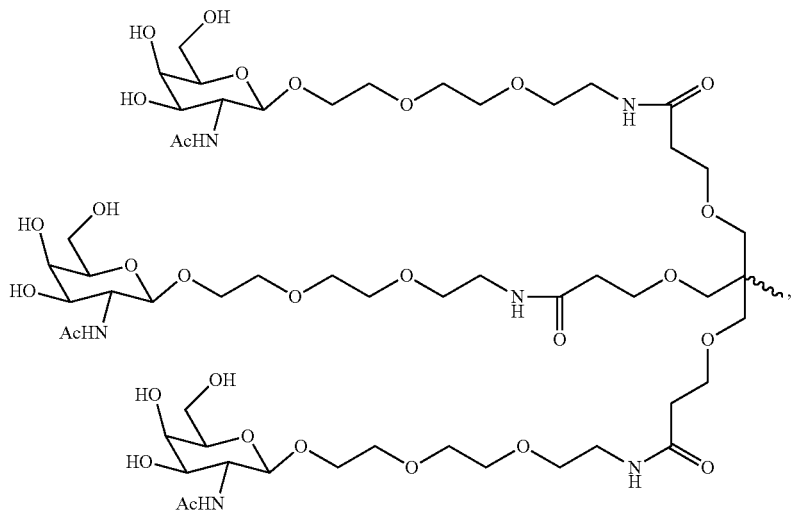

-continued
Formula XI
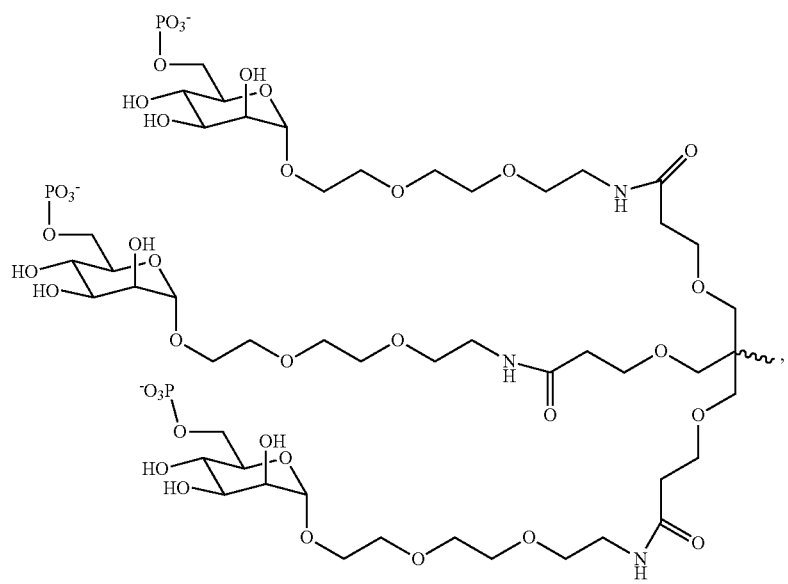
Formula XII
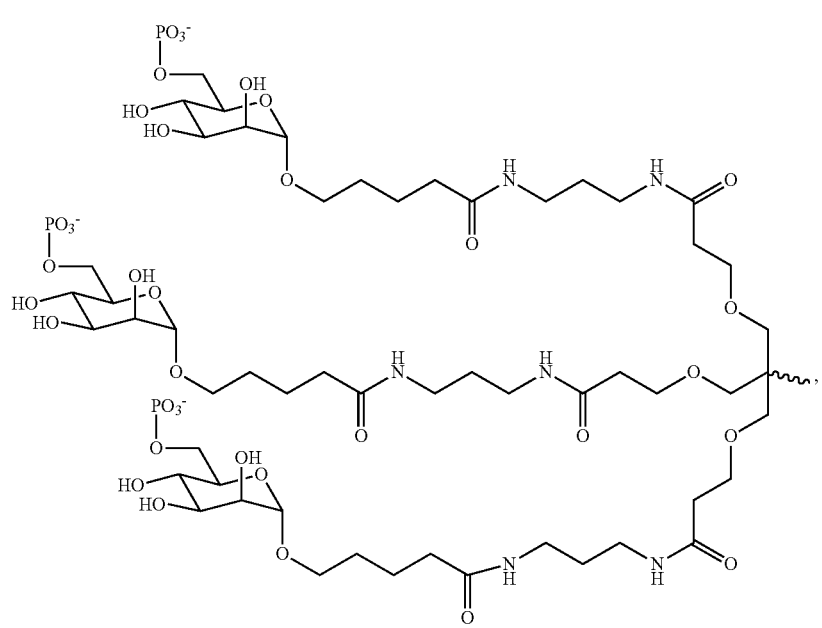
Formula XIII
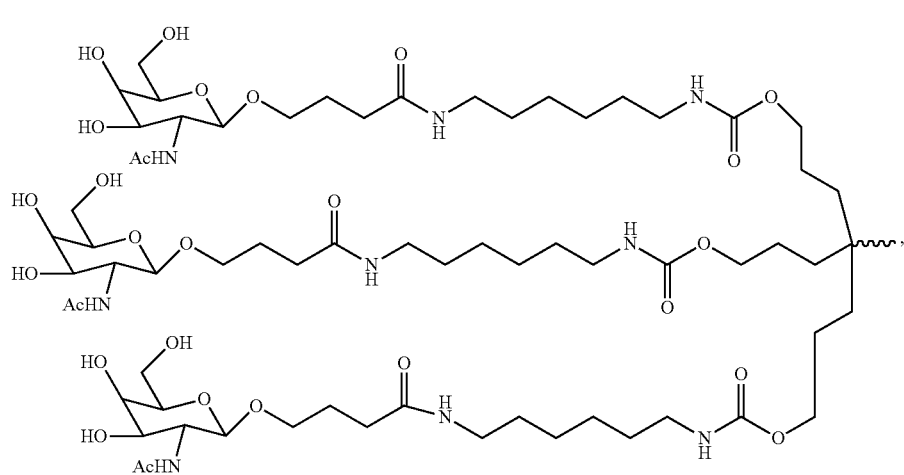

Formula XIV
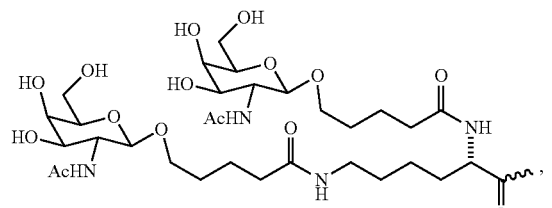
Formula XV
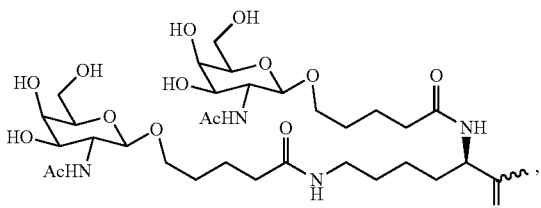
Formula XVI
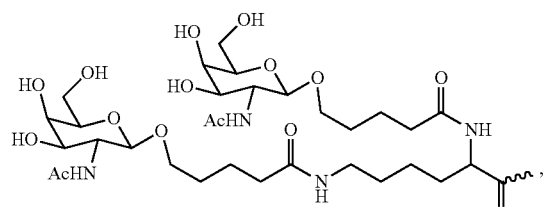
Formula XVII
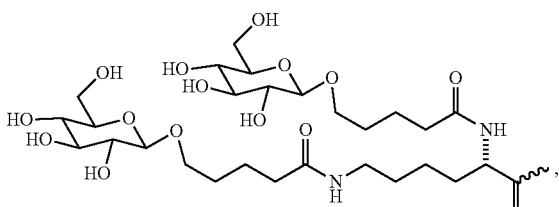
Formula XVIII
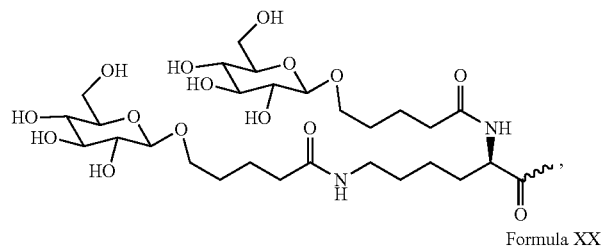
Formula XIX
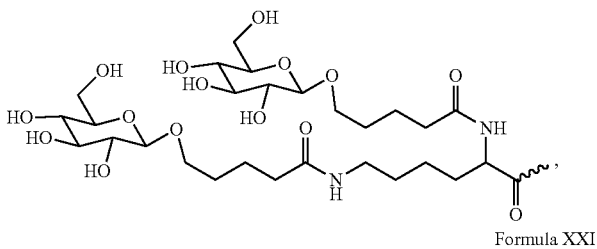
Formula XX
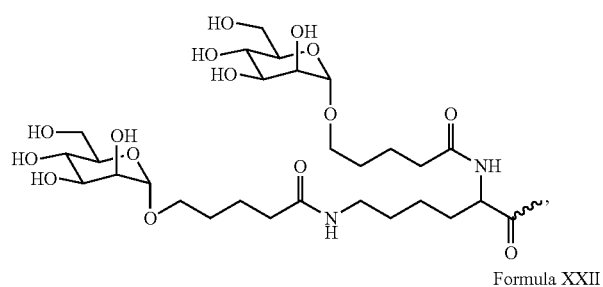
Formula XXI
Formula XXII
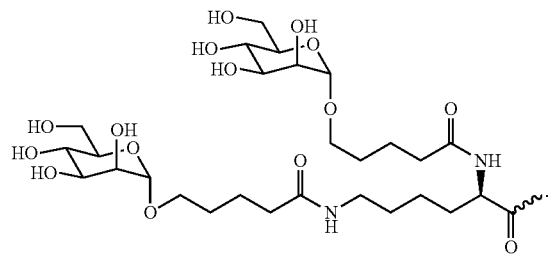
Another representative carbohydrate conjugate for use in the embodiments described herein includes, but is not limited to,

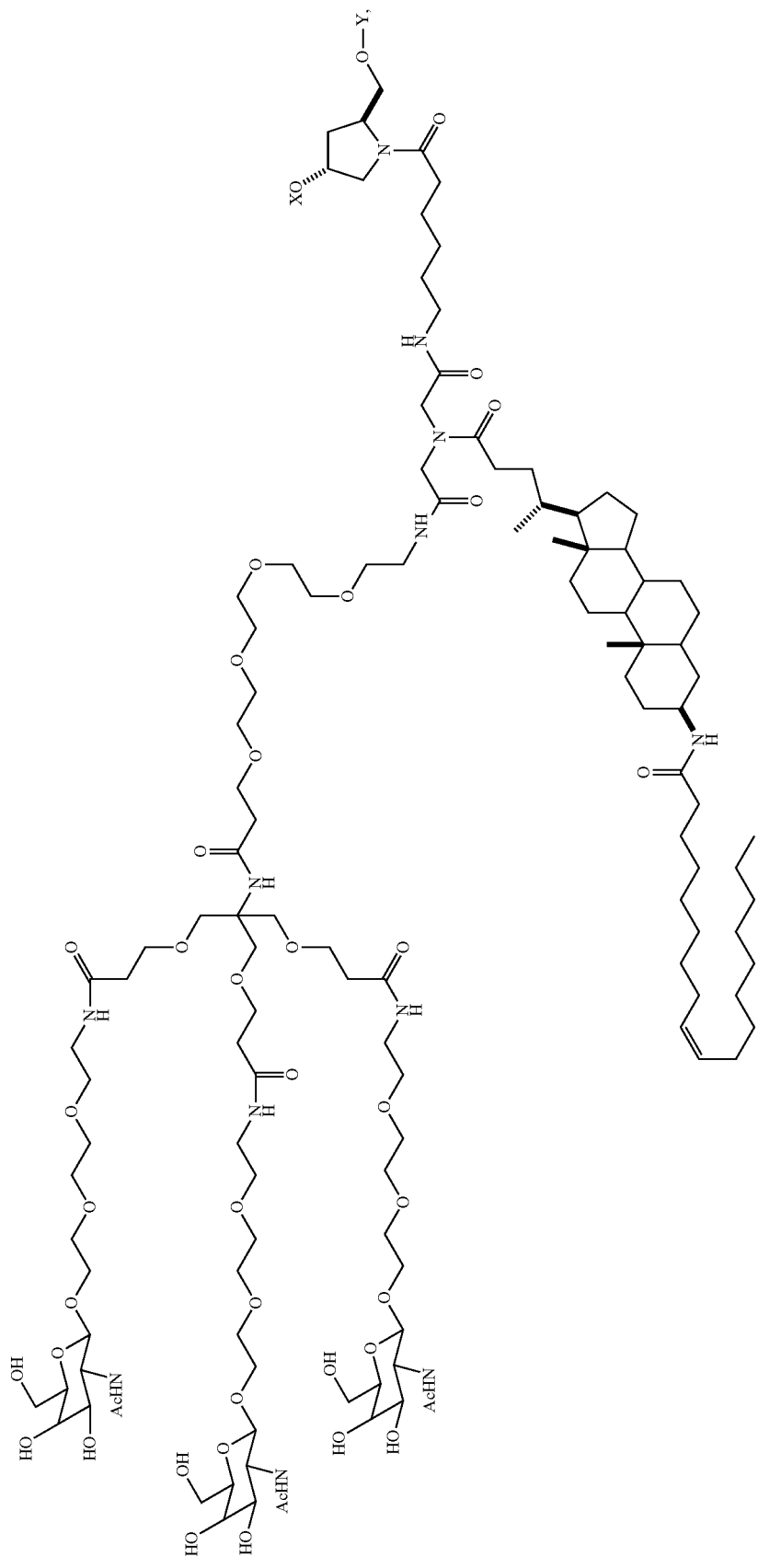
(Formula XXIII)

when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

D. Linkers

In some embodiments, the conjugate or ligand described herein can be attached to an antisense polynucleotide agent with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular antisense polynucleotide agent moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions).

The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an antisense polynucleotide agent of the invention is conjugated to a carbohydrate through a linker. Non-limiting examples of antisense polynucleotide agent carbohydrate conjugates with linkers of the compositions and methods of the invention include, but are not limited to, (Formula XXIV)

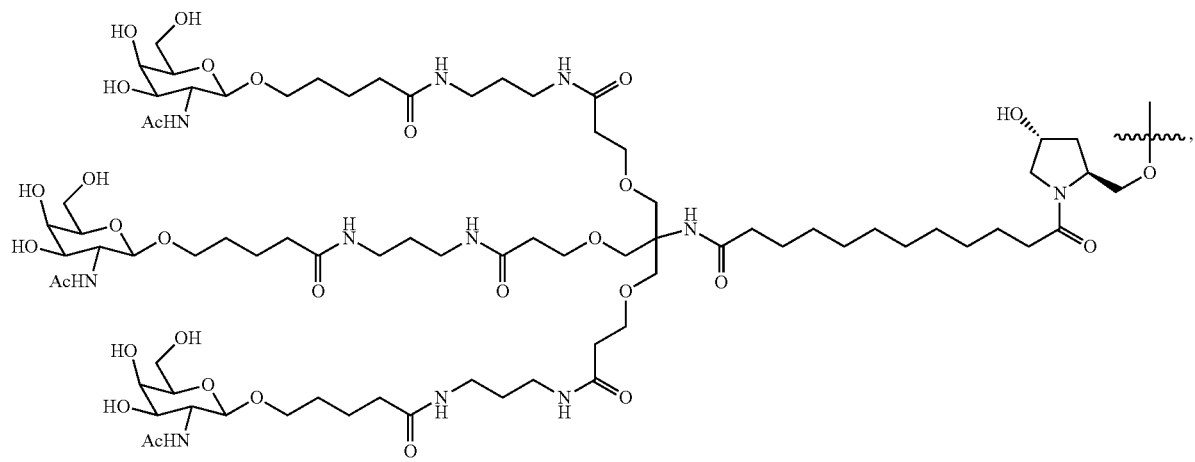

(Formula XXV)
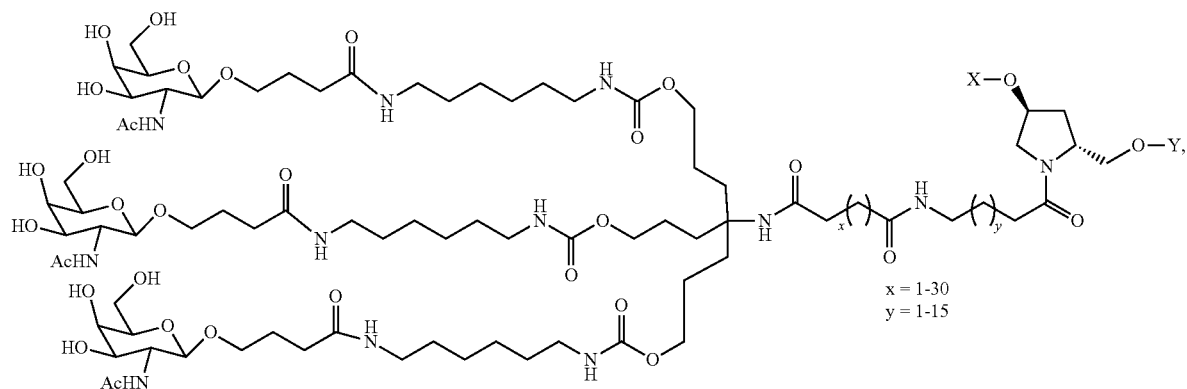
x = 1-30
y = 1-15
(Formula XXVI)
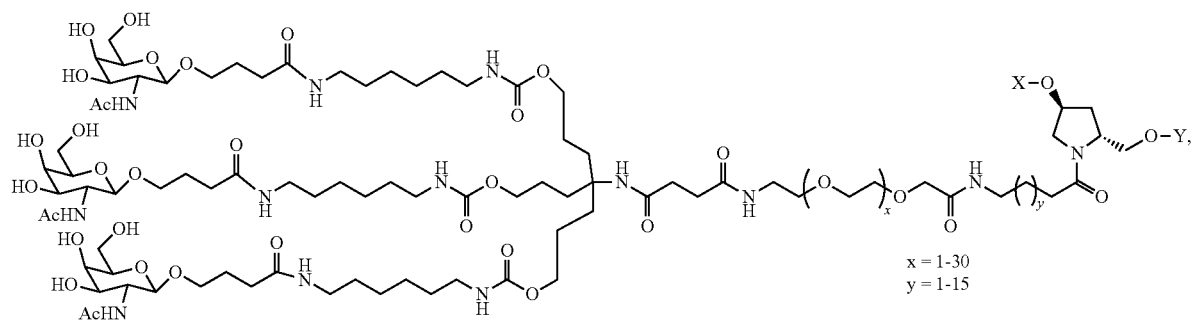
x = 1-30
y = 1-15
(Formula XXVII)
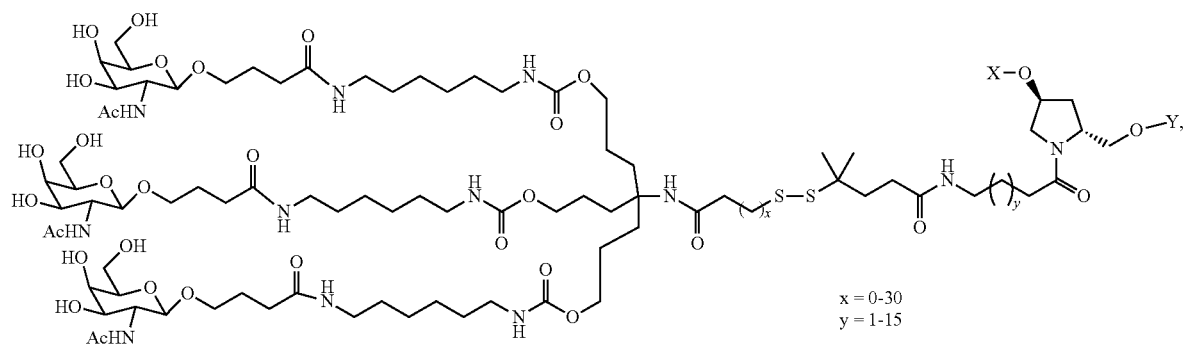
x = 0-30
y = 1-15
(Formula XXVIII)
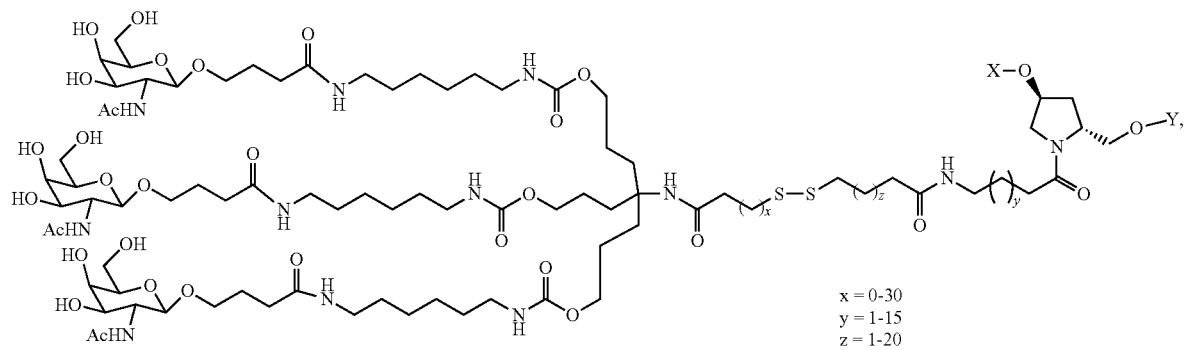
x = 0-30
y = 1-15
z = 1-20

(Formula XXIX)

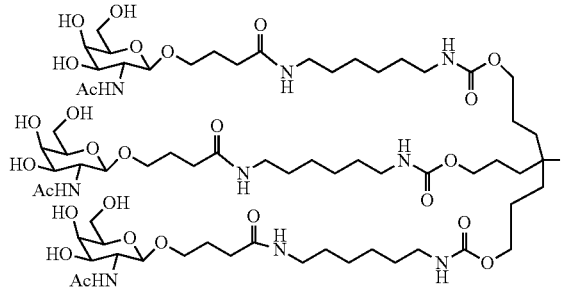 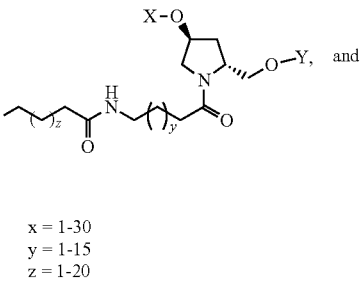

x = 1-30
y = 1-15
z = 1-20

(Formula XXX)

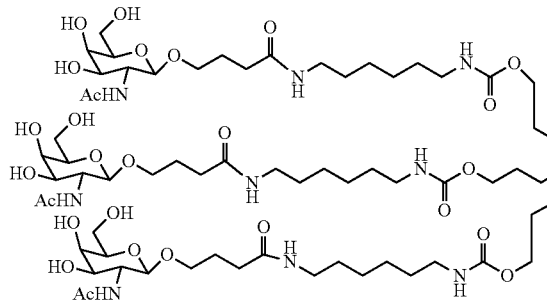 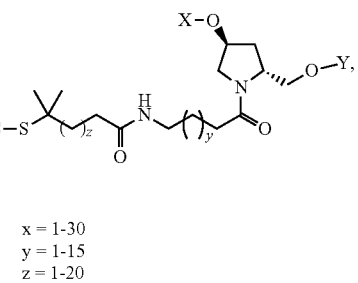

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a antisense polynucleotide agent of the invention is conjugated to a bivalent or trivalent branched linker selected from the group of structures shown in any of formula (XXXII)-(XXXV):

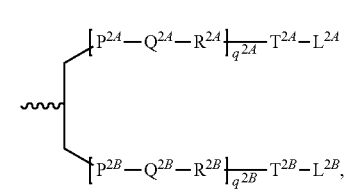

Formula XXXII

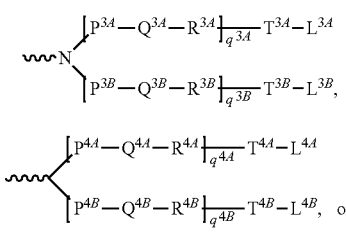

Formula XXXIII

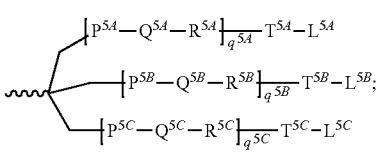

Formula XXXIV

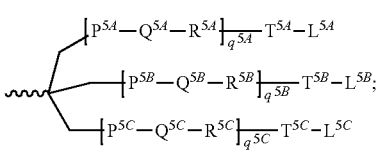

Formula XXXV wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherin one or more methylenes can be interrupted or terminated by one or more of O, S, S(O), SO$_2$, N(R$^N$), C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

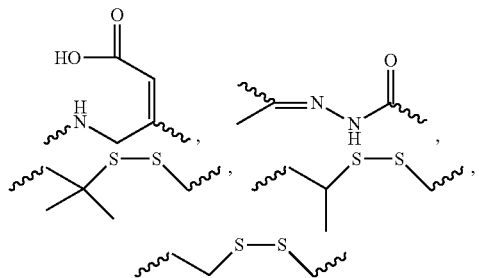

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide;

and $R^a$ is H or amino acid side chain. Trivalent conjugating GalNAc derivatives are particularly useful for use with antisense polynucleotide agents for inhibiting the expression of a target gene, such as those of formula (XXXVI):

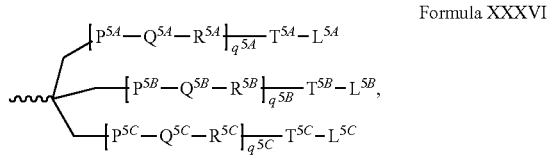

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an antisense polynucleotide agent. The present invention also includes antisense polynucleotide agents that are chimeric compounds.

"Chimeric" antisense polynucleotide agents or "chimeras," in the context of this invention, are antisense polynucleotide agent compounds, which contain two or more chemically distinct regions, each made up of at least one monomer unit, i.e., a nucleotide in the case of an antisense polynucleotide agent. These antisense polynucleotide agents typically contain at least one region wherein the RNA is modified so as to confer upon the antisense polynucleotide agent increased resistance to nuclease degradation, increased cellular uptake, and/or increased binding affinity for the target nucleic acid. An additional region of the antisense polynucleotide agent can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense polynucleotide agent inhibition of gene expression. Consequently, comparable results can often be obtained with shorter antisense polynucleotide agents when chimeric antisense polynucleotide agents are used, compared to phosphorothioate deoxy antisense polynucleotide agents hybridizing to the same target region. Cleavage of the RNA target can be routinely detected by gel electrophoresis and, if necessary, associated nucleic acid hybridization techniques known in the art.

In certain instances, the nucleotide of an antisense polynucleotide agent can be modified by a non-ligand group. A number of non-ligand molecules have been conjugated to antisense polynucleotide agents in order to enhance the activity, cellular distribution or cellular uptake of the antisense polynucleotide agent, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Lett.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylaminocarbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an Antisense Polynucleotide Agent of the Invention

The delivery of an antisense polynucleotide agent of the invention to a cell e.g., a cell within a subject, such as a human subject (e.g., a subject in need thereof, such as a subject having a LECT2-associated disease) can be achieved in a number of different ways. For example, delivery may be performed by contacting a cell with an antisense polynucleotide agent of the invention either in vitro or in vivo. In vivo delivery may also be performed directly by administering a composition comprising an antisense polynucleotide agent to a subject.

In general, any method of delivering a nucleic acid molecule (in vitro or in vivo) can be adapted for use with an antisense polynucleotide agent of the invention (see e.g., Akhtar S. and Julian R L. (1992) *Trends Cell. Biol.* 2(5): 139-144 and WO94/02595, which are incorporated herein by reference in their entireties). For in vivo delivery, factors to consider in order to deliver an antisense polynucleotide agent include, for example, biological stability of the delivered molecule, prevention of non-specific effects, and accumulation of the delivered molecule in the target tissue. The non-specific effects of an antisense polynucleotide agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the antisense polynucleotide agent to be administered. Several studies have shown successful knockdown of gene products when an antisense polynucleotide agent is administered locally. For example, intraocular delivery of a VEGF antisense polynucleotide agent by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a antisense polynucleotide agent in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an antisense polynucleotide agent systemically for the treatment of a disease, the agent can be modified or alternatively delivered using a drug delivery system; both methods act to prevent the rapid degradation of the antisense polynucleotide agent by endo- and exo-nucleases in vivo. Modification of the agent or the pharmaceutical carrier can also permit targeting of the antisense polynucleotide agent composition to the target tissue and avoid undesirable off-target effects. Antisense polynucleotide agent can be modified by chemical conjugation to lipophilic groups such as cholesterol to enhance cellular uptake and prevent degradation. In an alternative embodiment, the antisense polynucleotide agent can be delivered using drug delivery systems such as a nanoparticle, a dendrimer, a polymer, liposomes, or a cationic delivery system. Positively charged cationic delivery systems facilitate binding of an antisense polynucleotide agent molecule (negatively charged) and also enhance interactions at the negatively charged cell membrane to permit efficient uptake of an antisense polynucleotide agent by the cell. Cationic lipids, dendrimers, or polymers can either be bound to an antisense polynucleotide agent, or induced to form a vesicle or micelle (see e.g., Kim S H., et al (2008) *Journal of Controlled Release* 129(2):107-116) that encases an antisense polynucleotide agent. The formation of vesicles or micelles further prevents degradation of the antisense polynucleotide agent when administered systemically. Methods for making and administering cationic-antisense polynucleotide agent complexes are well within the abilities of one skilled in the art (see e.g., Sorensen, D R., et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of antisense polynucleotide agents include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an antisense polynucleotide agent forms a complex with cyclodextrin for systemic administration. Methods for administration and pharmaceutical compositions of antisense polynucleotide agents and cyclodextrins can be found in U.S. Pat. No. 7,427,605, which is herein incorporated by reference in its entirety.

VI. Pharmaceutical Compositions of the Invention

The present invention also includes pharmaceutical compositions and formulations which include the antisense polynucleotide agents of the invention. In one embodiment, provided herein are pharmaceutical compositions containing an antisense polynucleotide agent, as described herein, and a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum components, such as serum albumin, HDL and LDL; and (22) other non-toxic compatible substances employed in pharmaceutical formulations.

The pharmaceutical compositions containing the antisense polynucleotide agents are useful for treating a disease or disorder associated with the expression or activity of a LECT2 gene, e.g. a LECT2-associated disease. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the liver.

The pharmaceutical compositions of the invention may be administered in dosages sufficient to inhibit expression of a LECT2 gene. In general, a suitable dose of an antisense polynucleotide agent of the invention will be in the range of about 0.001 to about 200.0 milligrams per kilogram body weight of the recipient per day, generally in the range of about 0.1 to 50 mg per kilogram body weight per day. For example, the antisense polynucleotide agent can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, or about 100 mg/kg per single dose.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. Values and ranges intermediate to the recited values are also intended to be part of this invention.

In another embodiment, the antisense polynucleotide agent is administered at a dose of about 0.1 to about 100 mg/kg, about 0.25 to about 100 mg/kg, about 0.5 to about 100 mg/kg, about 0.75 to about 100 mg/kg, about 1 to about 100 mg/mg, about 1.5 to about 100 mg/kg, about 2 to about 100 mg/kg, about 2.5 to about 100 mg/kg, about 3 to about 100 mg/kg, about 3.5 to about 100 mg/kg, about 4 to about 100 mg/kg, about 4.5 to about 100 mg/kg, about 5 to about 100 mg/kg, about 7.5 to about 100 mg/kg, about 10 to about 100 mg/kg, about 15 to about 100 mg/kg, about 20 to about 100 mg/kg, about 25 to about 100 mg/kg, about 30 to about 100 mg/kg, about 35 to about 100 mg/kg, about 40 to about 100 mg/kg, about 45 to about 100 mg/kg, about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kg, about 2 to about 30 mg/kg, about 2.5 to about 30 mg/kb, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the antisense polynucleotide agent may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. Values and ranges intermediate to the recited values are also intended to be part of this invention.

In another embodiment, the antisense polynucleotide agent is administered at a dose of about 0.1 to about 100 mg/kg, about 0.25 to about 100 mg/kg, about 0.5 to about 100 mg/kg, about 0.75 to about 100 mg/kg, about 1 to about 100 mg/mg, about 1.5 to about 100 mg/kg, about 2 to about 100 mg/kg, about 2.5 to about 100 mg/kg, about 3 to about 100 mg/kg, about 3.5 to about 100 mg/kg, about 4 to about 100 mg/kg, about 4.5 to about 100 mg/kg, about 5 to about 100 mg/kg, about 7.5 to about 100 mg/kg, about 10 to about 100 mg/kg, about 15 to about 100 mg/kg, about 20 to about 100 mg/kg, about 25 to about 100 mg/kg, about 30 to about 100 mg/kg, about 35 to about 100 mg/kg, about 40 to about 100 mg/kg, about 45 to about 100 mg/kg, about 0.5 to about 50 mg/kg, about 0.75 to about 50 mg/kg, about 1 to about 50 mg/mg, about 1.5 to about 50 mg/kgb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the antisense polynucleotide agent is administered at a dose of about 0.5 mg/kg to about 10 mg/kg. Values and ranges intermediate to the recited values are also intended to be part of this invention.

For example, subjects can be administered, e.g., subcutaneously or intravenously, a single therapeutic amount of antisense polynucleotide agent, such as about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. Values and ranges intermediate to the recited values are also intended to be part of this invention.

In some embodiments, subjects are administered, e.g., subcutaneously or intravenously, multiple doses of a therapeutic amount of antisense polynucleotide agent, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. A multi-dose regimine may include administration of a therapeutic amount of antisense polynucleotide agent daily, such as for two days, three days, four days, five days, six days, seven days, or longer.

In other embodiments, subjects are administered, e.g., subcutaneously or intravenously, a repeat dose of a therapeutic amount of antisense polynucleotide agent, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. A repeat-dose regimine may include administration of a therapeutic amount of antisense polynucleotide agent on a regular basis, such as every other day, every third day, every fourth day, twice a week, once a week, every other week, or once a month.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the antisense polynucleotide agent can be administered as two, three, or more sub-doses at appropriate intervals throughout the day or even using continuous infusion or delivery through a controlled release formulation. In that case, the antisense polynucleotide agent contained in each sub-dose must be correspondingly smaller in order to achieve the total daily dosage. The dosage unit can also be compounded for delivery over several days, e.g., using a conventional sustained release formulation which provides sustained release of the antisense polynucleotide agent over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual antisense polynucleotide agents encompassed by the invention can be made using conventional methodologies or on the basis of in vivo testing using an appropriate animal model, as described elsewhere herein.

A suitable animal model, e.g., a mouse containing a transgene expressing human LECT2, can be used to determine the therapeutically effective dose and/or an effective dosage regimen administration of LECT2 antisense polynucleotide.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The antisense polynucleotide agent can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the antisense polynucleotide agents featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). Antisense polynucleotide agents featured in the invention can be encapsulated within liposomes or can form complexes thereto, in particular to cationic liposomes. Alternatively, antisense polynucleotide agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. Antisense Polynucleotide Agent Formulations Comprising Membranous Molecular Assemblies An antisense polynucleotide agent for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the antisense polynucleotide agent composition. The lipophilic material isolates the aqueous interior from an aqueous exterior, which typically does not include the antisense polynucleotide agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the antisense polynucleotide agent are delivered into the cell where the antisense polynucleotide agent can specifically bind to a target RNA and can mediate antisense inhibition. In some cases the liposomes are also specifically targeted, e.g., to direct the antisense polynucleotide agent to particular cell types.

A liposome containing an antisense polynucleotide agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The antisense polynucleotide agent preparation is then added to the micelles that include the lipid component. The cationic groups on the lipid interact with the antisense polynucleotide agent and condense around the antisense polynucleotide agent to form a liposome. After condensation, the detergent is removed, e.g., by dialysis, to yield a liposomal preparation of antisense polynucleotide agent.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging antisense polynucleotide agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver antisense polynucleotide agents to macrophages.

Further advantages of liposomes include: liposomes obtained from natural phospholipids are biocompatible and biodegradable; liposomes can incorporate a wide range of water and lipid soluble drugs; liposomes can protect encapsulated antisense polynucleotide agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of Antisense polynucleotide agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (see, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration; liposomes present several advantages over other formulations. Such advantages include reduced side effects related to high systemic absorption of the administered drug, increased accumulation of the administered drug at the desired target, and the ability to administer an antisense polynucleotide agent into the skin. In some implementations, liposomes are used for delivering antisense polynucleotide agenst to epidermal cells and also to enhance the penetration of antisense polynucleotide agenst into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with antisense polynucleotide agents are useful for treating a dermatological disorder.

Liposomes that include antisense polynucleotide agent can be made highly deformable. Such deformability can enable the liposomes to penetrate through pore that are smaller than the average radius of the liposome. For example, transferosomes are a type of deformable liposomes. Transferosomes can be made by adding surface edge activators, usually surfactants, to a standard liposomal composition. Transfersomes that include antisense polynucleotide agents can be delivered, for example, subcutaneously by infection in order to deliver antisense polynucleotide agents to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. Nos. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The antisense polynucleotide agent for use in the compositions and methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the antisense polynucleotide agent composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the antisense polynucleotide agent composition and at least the alkali metal alkyl sulphate. The first micellar composition is then mixed with at least three micelle forming compounds to form a mixed micellar composition. In another method, the micellar composition is prepared by mixing the antisense polynucleotide agent composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

Antisense polynucleotide agents of in the invention may be fully encapsulated in a lipid formulation, e.g., a LNP, or other nucleic acid-lipid particle.

As used herein, the term "LNP" refers to a stable nucleic acid-lipid particle comprising a lipid layer encapsulating a pharmaceutically active molecule. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; 6,858,225; 8,158,601; and 8,058,069; U.S. Publication No. 2010/0324120 and PCT Publication No. WO 96/40964.

In one embodiment, the lipid to drug ratio (mass/mass ratio) (e.g., lipid to antisense polynucleotide agent ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-santisense polynucleotide agent nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-antisense polynucleotide agent particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 antisense polynucleotide agent/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoyl-phosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98-4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-antisense polynucleotide agent nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous antisense polynucleotide agent (e.g., in sodium acetate pH 5) such that the final ethanol concentration is about 35-45% and the final sodium acetate concentration is about 100-300 mM. Lipid-antisense polynucleotide agent nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

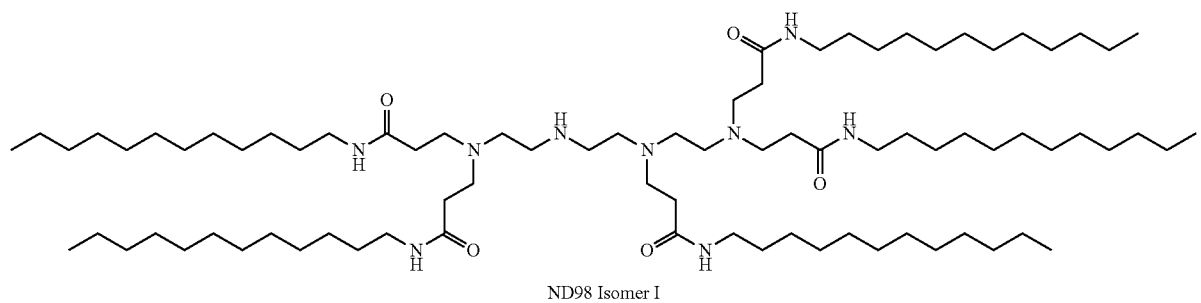

Formula 1

ND98 Isomer I

LNP01 formulations are described, e.g., in International Application Publication No. WO 2008/042973, which is hereby incorporated by reference.

Additional exemplary lipid-antisense polynucleotide agent formulations are described in Table 1.

TABLE 1

| | Ionizable/Cationic Lipid | cationic lipid/non-cationic lipid/cholesterol/PEG-lipid conjugate Lipid:santisense polynucleotide agent ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:santisense polynucleotide agent ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:santisense polynucleotide agent ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:santisense polynucleotide agent 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:santisense polynucleotide agent 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:santisense polynucleotide agent 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:santisense polynucleotide agent 10:1 |
| LNP13 | XTC | XTC/DSPC/Chol/PEG-DMG 50/10/38.5/1.5 Lipid:santisense polynucleotide agent: 33:1 |
| LNP14 | MC3 | MC3/DSPC/Chol/PEG-DMG 40/15/40/5 Lipid:santisense polynucleotide agent: 11:1 |
| LNP15 | MC3 | MC3/DSPC/Chol/PEG-DSG/GalNAc-PEG-DSG 50/10/35/4.5/0.5 Lipid:santisense polynucleotide agent: 11:1 |
| LNP16 | MC3 | MC3/DSPC/Chol/PEG-DMG 50/10/38.5/1.5 Lipid:santisense polynucleotide agent: 7:1 |
| LNP17 | MC3 | MC3/DSPC/Chol/PEG-DSG 50/10/38.5/1.5 Lipid:santisense polynucleotide agent: 10:1 |

TABLE 1-continued

| | Ionizable/Cationic Lipid | cationic lipid/non-cationic lipid/cholesterol/PEG-lipid conjugate Lipid:santisense polynucleotide agent ratio |
|---|---|---|
| LNP18 | MC3 | MC3/DSPC/Chol/PEG-DMG 50/10/38.5/1.5 Lipid:santisense polynucleotide agent: 12:1 |
| LNP19 | MC3 | MC3/DSPC/Chol/PEG-DMG 50/10/35/5 Lipid:santisense polynucleotide agent: 8:1 |
| LNP20 | MC3 | MC3/DSPC/Chol/PEG-DPG 50/10/38.5/1.5 Lipid:santisense polynucleotide agent: 10:1 |
| LNP21 | C12-200 | C12-200/DSPC/Chol/PEG-DSG 50/10/38.5/1.5 Lipid:santisense polynucleotide agent: 7:1 |
| LNP22 | XTC | XTC/DSPC/Chol/PEG-DSG 50/10/38.5/1.5 Lipid:santisense polynucleotide agent: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.
XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.
MC3 comprising formulations are described, e.g., in U.S. Publication No. 2010/0324120, filed Jun. 10, 2010, the entire contents of which are hereby incorporated by reference.
ALNY-100 comprising formulations are described, e.g., International patent application number PCT/US09/63933, filed on Nov. 10, 2009, which is hereby incorporated by reference.
C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, protecting groups can be used. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

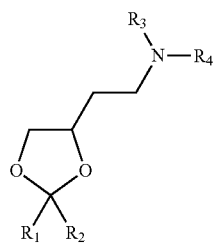

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

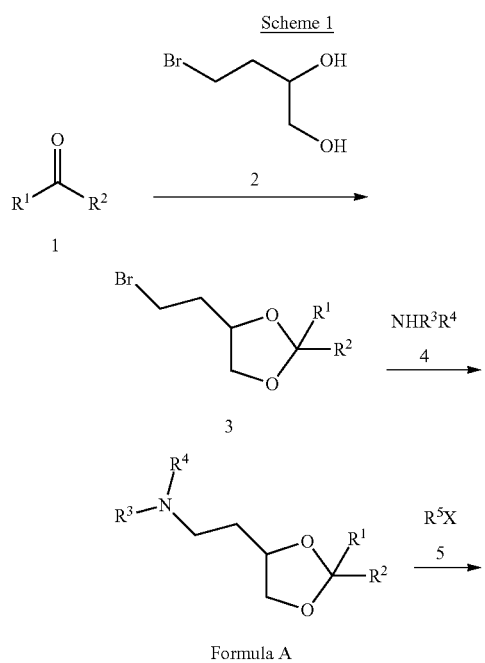

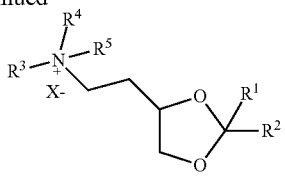

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

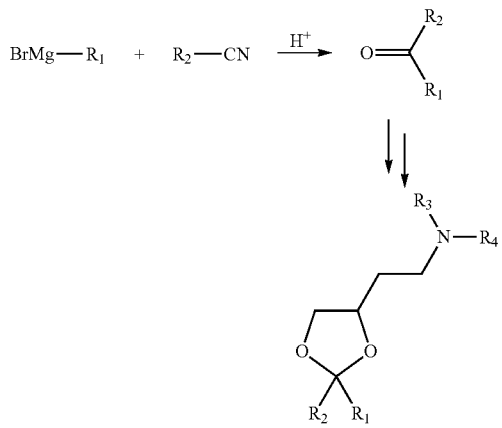

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100
Synthesis of ketal 519 [ALNY-100] was performed using the following scheme 3:

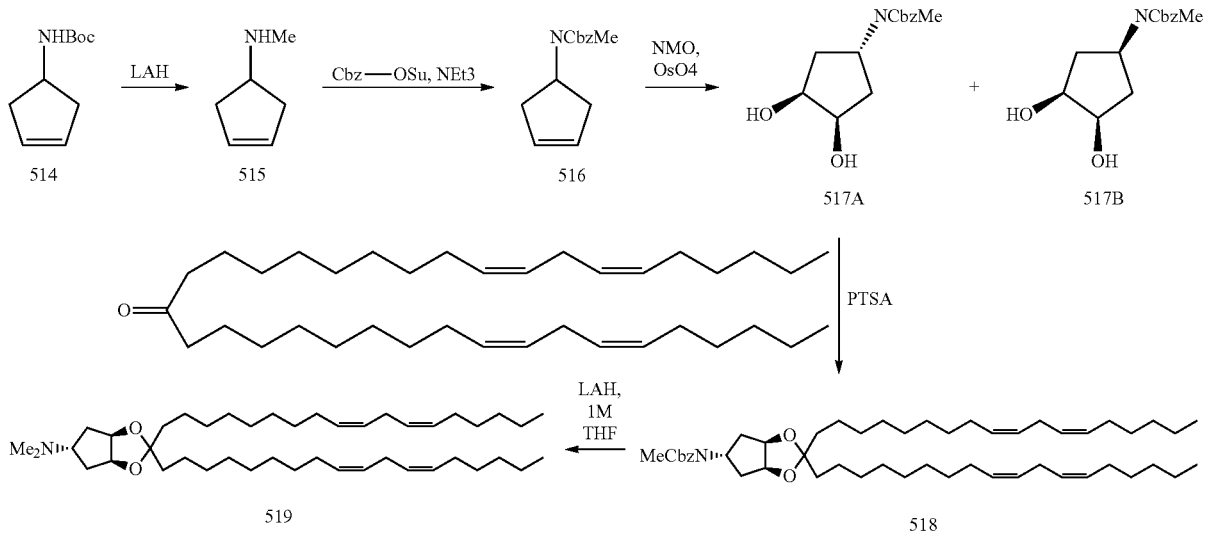

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0 0C under nitrogen atmosphere. After complete addition, reaction mixture was warmed to room temperature and then heated to reflux for 4 h. Progress of the reaction was monitored by TLC. After completion of reaction (by TLC) the mixture was cooled to 0 0C and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0 0C under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1×50 mL). Organic phase was dried over an Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]-266.3, [M+NH4+]—283.5 present, HPLC-97.86%.

Stereochemistry Confirmed by X-Ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m,1H), 4.58-4.57 (m,2H), 2.78-2.74 (m,7H), 2.06-2.00 (m,8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total antisense polynucleotide agent concentration in the formulation, as well as the entrapped fraction, is estimated using a dye exclusion assay. A sample of the formulated antisense polynucleotide agent can be incubated with an RNA-binding dye, such as Ribogreen (Molecular Probes) in the presence or absence of a formulation disrupting surfactant, e.g., 0.5% Triton-X100. The total antisense polynucleotide agent in the formulation can be determined by the signal from the sample containing the surfactant, relative to a standard curve. The entrapped fraction is determined by subtracting the "free" antisense polynucleotide agent content (as measured by the signal in the absence of surfactant) from the total antisense polynucleotide agent content. Percent entrapped antisense polynucleotide agent is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which the antisense polynucleotide agents featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydrofusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. Antisense polynucleotide agents featured in the invention can be delivered orally, in granular form including sprayed dried particles, or complexed to form micro or nanoparticles. Antisense polynucleotide agent complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for antisense polynucleotide agents and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations
i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of antisense polynucleotide agents are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research*, 1994, 11, 1385; Ho et al., *J. Pharm. Sci.*, 1996, 85, 138-143). Often microemulsions can form spontaneously when their components are brought together at ambient temperature. This can be particularly advantageous when formulating thermolabile drugs, peptides or antisense polynucleotide agents. Microemulsions have also been effective in the transdermal delivery of active components in both cosmetic and pharmaceutical applications. It is expected that the microemulsion compositions and formulations of the present invention will facilitate the increased systemic absorption of antisense polynucleotide agents from the gastrointestinal tract, as well as improve the local cellular uptake of antisense polynucleotide agents and nucleic acids.

Microemulsions of the present invention can also contain additional components and additives such as sorbitan monostearate (Grill 3), Labrasol, and penetration enhancers to improve the properties of the formulation and to enhance the absorption of the antisense polynucleotide agents of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

iii. Microparticles

An antisense polynucleotide agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly antisense polynucleotide agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of antisense polynucleotide agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of antisense polynucleotide agents through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of antisense polynucleotide agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of antisense polynucleotide agents at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of antisense polynucleotide agents. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated antisense polynucleotide agent in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense polynucleotide agent Res. Dev., 1995, 5, 115-121; Takakura et al., Antisense polynucleotide agent & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more antisense polynucleotide agents and (b) one or more biologic agents which function by a non-antisense polynucleotide mechanism. Examples of such biologic agents include agents that interfere with an interaction of LECT2 and at least one LECT2 binding partner. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the $ED_{50}$ with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the antisense polynucleotide agents featured in the invention can be administered in combination with other known agents effective in treatment of pathological processes mediated by LECT2 gene expression. In any event, the administering physician can adjust the amount and timing of antisense polynucleotide agent administration on the basis of results observed using standard measures of efficacy known in the art or described herein.

VII. Methods for Inhibiting LECT2 Gene Expression

The present invention provides methods of inhibiting expression of LECT2 in a cell. The methods include contacting a cell with an antisense polynucleotide agent of the invention in an amount effective to inhibit expression of the LECT2 gene in the cell, thereby inhibiting expression of the LECT2 in the cell.

Contacting of a cell with an antisense polynucleotide agent may be done in vitro or in vivo. Contacting a cell in vivo with the antisense polynucleotide agent includes contacting a cell or group of cells within a subject, e.g., a human subject, with the antisense polynucleotide agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the antisense polynucleotide agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a LECT2" is intended to refer to inhibition of expression of any LECT2 gene (such as, e.g., a mouse LECT2 gene, a rat LECT2 gene, a monkey LECT2 gene, or a human LECT2 gene) as well as variants or mutants of a LECT2 gene. Thus, the LECT2 gene may be a wild-type LECT2 gene, a mutant LECT2 gene, or a transgenic LECT2 gene in the context of a genetically manipulated cell, group of cells, or organism.

"Inhibiting expression of a LECT2 gene" includes any level of inhibition of a LECT2 gene, e.g., at least partial suppression of the expression of a LECT2 gene. The expression of the LECT2 gene may be assessed based on the level, or the change in the level, of any variable associated with LECT2 gene expression, e.g., LECT2 mRNA level, LECT2 protein level. This level may be assessed in an individual cell or in a group of cells, including, for example, a sample derived from a subject.

Inhibition may be assessed by a decrease in an absolute or relative level of one or more variables that are associated with LECT2 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a LECT2 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a LECT2 gene may be manifested by a reduction of the amount of mRNA expressed by a first cell or group of cells (such cells may be present, for example, in a sample derived from a subject) in which a LECT2 gene is transcribed and which has or have been treated (e.g., by contacting the cell or cells with an antisense polynucleotide agent of the invention, or by administering an antisense polynucleotide agent of the invention to a subject in which the cells are or were present) such that the expression of a LECT2 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a LECT2 gene may be assessed in terms of a reduction of a parameter that is functionally linked to LECT2 gene expression, e.g., LECT2 protein expression. LECT2 gene silencing may be determined in any cell expressing LECT2, either constitutively or by genomic engineering, and by any assay known in the art.

Inhibition of the expression of a LECT2 protein may be manifested by a reduction in the level of the LECT2 protein that is expressed by a cell or group of cells (e.g., the level of protein expressed in a sample derived from a subject). As explained above for the assessment of mRNA suppression, the inhibiton of protein expression levels in a treated cell or group of cells may similarly be expressed as a percentage of the level of protein in a control cell or group of cells.

A control cell or group of cells that may be used to assess the inhibition of the expression of a LECT2 gene includes a cell or group of cells that has not yet been contacted with an antisense polynucleotide agent of the invention. For example, the control cell or group of cells may be derived from an individual subject (e.g., a human or animal subject) prior to treatment of the subject with an antisense polynucleotide agent.

The level of LECT2 mRNA that is expressed by a cell or group of cells may be determined using any method known in the art for assessing mRNA expression. In one embodiment, the level of expression of LECT2 in a sample is determined by detecting a transcribed polynucleotide, or portion thereof, e.g., mRNA of the LECT2 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of LECT2 is determined using a nucleic acid probe. The term "probe", as used herein, refers to any molecule that is capable of selectively binding to a specific LECT2. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to LECT2 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of LECT2 mRNA.

An alternative method for determining the level of expression of LECT2 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of LECT2 is determined by quantitative fluorogenic RT-PCR (i.e., the TaqMan™ System).

The expression levels of LECT2 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of LECT2 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of LECT2 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the antisense polynucleotide agent is administered to a subject such that the antisense polynucleotide agent is delivered to a specific site within the subject. The inhibition of expression of LECT2 may be assessed using measurements of the level or change in the level of LECT2 mRNA or LECT2 protein in a sample derived from fluid or tissue from the specific site within the subject. The site may also be a subsection or subgroup of cells from any one of the aforementioned sites. The site may also include cells that express a particular type of receptor.

The phrase "contacting a cell with an antisense polynucleotide agent," as used herein, includes contacting a cell by any possible means. Contacting a cell with an antisense polynucleotide agent includes contacting a cell in vitro with the antisense polynucleotide agent or contacting a cell in vivo with the antisense polynucleotide agent. The contacting may be done directly or indirectly. Thus, for example, the antisense polynucleotide agent may be put into physical contact with the cell by the individual performing the method, or alternatively, the antisense polynucleotide agent may be put into a situation that will permit or cause it to subsequently come into contact with the cell.

Contacting a cell in vitro may be done, for example, by incubating the cell with the antisense polynucleotide agent. Contacting a cell in vivo may be done, for example, by injecting the antisense polynucleotide agent into or near the tissue where the cell is located, or by injecting the antisense polynucleotide agent into another area, e.g., the bloodstream or the subcutaneous space, such that the agent will subsequently reach the tissue where the cell to be contacted is located. For example, the antisense polynucleotide agent may contain and/or be coupled to a ligand, e.g., GalNAc3, that directs the antisense polynucleotide agent to a site of interest, e.g., the liver. Combinations of in vitro and in vivo methods of contacting are also possible. For example, a cell may also be contacted in vitro with an antisense polynucleotide agent and subsequently transplanted into a subject.

In one embodiment, contacting a cell with an antisense polynucleotide agent includes "introducing" or "delivering the antisense polynucleotide agent into the cell" by facilitating or effecting uptake or absorption into the cell. Absorption or uptake of an antisense polynucleotide agent can occur through unaided diffusive or active cellular processes, or by auxiliary agents or devices. Introducing an antisense polynucleotide agent into a cell may be in vitro and/or in vivo. For example, for in vivo introduction, antisense polynucleotide agent can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

VIII. Methods for Treating or Preventing a LECT2-Associated Disorder

The present invention also provides therapeutic and prophylactic methods which include administering to a subject having a LECT2-associated disease, e.g., amyloidosis, e.g. a LECT2 amyloidosis (ALECT2), an antisense polynucleotide agent or pharmaceutical compositions comprising an antisense polynucleotide agent of the invention. In some aspects of the invention, the methods further include administering to the subject an additional therapeutic agent.

In one aspect, the present invention provides methods of treating a subject having a disorder that would benefit from reduction in LECT2 expression, e.g., at LECT2-associated disease, e.g., amyloidosis, e.g. a LECT2 amyloidosis (ALECT2). The treatment methods (and uses) of the invention include administering to the subject, e.g., a human, a therapeutically effective amount of an antisense polynucleotide agent targeting a LECT2 gene or a pharmaceutical composition comprising an antisense polynucleotide agent targeting a LECT2 gene, thereby treating the subject having a disorder that would benefit from reduction in LECT2 expression.

In one aspect, the invention provides methods of preventing at least one symptom in a subject having a disorder that would benefit from reduction in LECT2 expression, e.g., a LECT2-associated disease, e.g., amyloidosis, e.g., a LECT2 amyloidosis (ALECT2). The methods include administering to the subject a prophylactically effective amount of an antisense polynucleotide agent targeting a LECT2 gene or a pharmaceutical composition comprising an antisense polynucleotide agent targeting a LECT2 gene, thereby preventing at least one symptom in the subject having a disorder that would benefit from reduction in LECT2 expression.

In yet another aspect, the present invention provides use of an antisense polynucleotide agent of the invention targeting a LECT2 gene or a pharmaceutical composition comprising an antisense polynucleotide agent targeting a LECT2 gene in the manufacture of a medicament for treating a subject, e.g., a subject that would benefit from a reduction and/or inhibition of LECT2 expression, such as a subject having a disorder that would benefit from reduction in LECT2 expression, e.g., a LECT2-associated disease, e.g., amyloidosis, e.g. a LECT2 amyloidosis (ALECT2).

In another aspect, the invention provides uses of an antisense polynucleotide agent of the invention for preventing at least one symptom in a subject suffering from a disorder that would benefit from a reduction and/or inhibition of LECT2 expression, such as a LECT2-associated disease, e.g., amyloidosis, e.g. a LECT2 amyloidosis (ALECT2).

In a further aspect, the present invention provides uses of an antisense polynucleotide agent of the invention in the manufacture of a medicament for preventing at least one symptom in a subject suffering from a disorder that would benefit from a reduction and/or inhibition of LECT2 expression, such as a LECT2-associated disease, e.g., amyloidosis, e.g. a LECT2 amyloidosis (ALECT2).

"Therapeutically effective amount," as used herein, is intended to include the amount of an antisense polynucleotide agent, that, when administered to a subject having a LECT2-associated disease, is sufficient to effect treatment of the disease (e.g., by diminishing, ameliorating or maintaining the existing disease or one or more symptoms of disease). The "therapeutically effective amount" may vary depending on the antisense polynucleotide agent or additional therapeutic agent, how the agent is administered, the disease and its severity and the history, age, weight, family history, genetic makeup, the types of preceding or concomitant treatments, if any, and other individual characteristics of the subject to be treated. Therapeutic effects of administration of a LECT2 antsense polynucleotide can be established, for example, by comparison with an appropriate control. For example, inhibition of amyloid deposition may be established, for example, in a group of patients with amyloidosis (e.g., LECT2 amyloidosis) by comparison of any appropriate parameter (e.g., a parameter assessing the size, number, or extent of amyloid deposition) with the same parameter in an appropriate control group. A control group (e.g., a group of similar individuals or the same group of individuals in a crossover design) may include, for example, an untreated population; a population that has been treated with a conventional treatment; a population that has been treated with placebo or a non-targeting iRNA; and the like.

"Prophylactically effective amount," as used herein, is intended to include the amount of an antisense polynucleotide agent that, when administered to a subject having a LECT2-associated disease but not yet (or currently) experiencing or displaying symptoms of the disease, and/or a subject at risk of developing a LECT2-associated disease, is sufficient to effect treatment of the disease (e.g., by diminishing, ameliorating or maintaining the existing disease or one or more symptoms of disease). Ameliorating the disease includes slowing the course of the disease or reducing the severity of later-developing disease. The "prophylactically effective amount" may vary depending on the antisense polynucleotide agent or anti-LECT2 antibody, or antigen-binding fragment thereof, how the agent or anti-LECT2 antibody, or antigen-binding fragment thereof, is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an antisense polynucleotide agent, that produces some desired local or systemic effect at a reasonable benefit/risk ratio applicable to any treatment. Antisense polynucleotide agents employed in the methods of the present invention may be administered in a sufficient amount to produce a reasonable benefit/risk ratio applicable to such treatment.

In another aspect, the present invention provides uses of a therapeutically effective amount of an antisense polynucleotide agent of the invention for treating a subject, e.g., a subject that would benefit from a reduction and/or inhibition of LECT2 expression.

As used herein, "LECT2 associated disease," a "disorder that would benefit from reduction in LECT2 expression", a "pathological process related to LECT2 expression," or the like includes any condition, disorder, or disease in which LECT2 expression is altered (e.g., decreased or increased relative to a normal level). In some embodiments, LECT2 expression is decreased. In some embodiments, LECT2 expression is increased. In embodiments, the decrease or increase in LECT2 expression is detectable in the blood (e.g., in the plasma) of the subject. In embodiments, the decrease or increase in LECT2 expression is detectable in a tissue sample from the subject (e.g., in a kidney sample or a liver sample). The decrease or increase may be assessed relative the level observed in the same individual prior to the development of the disorder or relative to other individual(s) who do not have the disorder. The decrease or increase may be limited to a particular organ, tissue, or region of the body (e.g., the kidney or the liver).

In some embodiments, the subject is an animal that serves as a model for a disorder related to LECT2 expression, e.g., a LECT2 amyloidosis.

The methods and uses of the invention include administering a composition described herein such that expression of the target LECT2 gene is decreased, such as for about 1, 2, 3, 4, 5, 6, 7, 8, 12, 16, 18, 24, 28, 32, 36, 40, 44, 48, 52, 56, 60, 64, 68, 72, 76, or about 80 hours. In one embodiment, expression of the target LECT2 gene is decreased for an extended duration, e.g., at least about two, three, four, five, six, seven days or more, e.g., about one week, two weeks, three weeks, or about four weeks or longer.

Administration of the antisense polynucleotide agent according to the methods and uses of the invention may result in a reduction of the severity, signs, symptoms, and/or markers of such diseases or disorders in a patient with a LECT2-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an antisense polynucleotide agent targeting LECT2 or pharmaceutical composition thereof, "effective against" a LECT2-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating a LECT2-associated disease and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given antisense polynucleotide agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an antisense polynucleotide agent or antisense polynucleotide agent formulation as described herein.

Subjects can be administered a therapeutic amount of antisense polynucleotide agent, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 9.0 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or about 100 mg/kg. Values and ranges intermediate to the recited values are also intended to be part of this invention.

In certain embodiments, for example, when a composition of the invention comprises a antisense polynucleotide agent as described herein and a lipid, subjects can be administered a therapeutic amount of antisense polynucleotide agent, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a antisense polynucleotide agent as described herein and an N-acetylgalactosamine, subjects can be administered a therapeutic amount of antisense polynucleotide agent, such as a dose of about 0.1 to about 100 mg/kg, about 0.25 to about 100 mg/kg, about 0.5 to about 100 mg/kg, about 0.75 to about 100 mg/kg, about 1 to about 100 mg/mg, about 1.5 to about 100 mg/kg, about 2 to about 100 mg/kg, about 2.5 to about 100 mg/kg, about 3 to about 100 mg/kg, about 3.5 to about 100 mg/kg, about 4 to about 100 mg/kg, about 4.5 to about 100 mg/kg, about 5 to about 100 mg/kg, about 7.5 to about 100 mg/kg, about 10 to about 100 mg/kg, about 15 to about 100 mg/kg, about 20 to about 100 mg/kg, about 25 to about 100 mg/kg, about 30 to about 100 mg/kg, about 35 to about 100 mg/kg, about 40 to about 100 mg/kg, about 45 to about 100 mg/kg, about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 30 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a antisense polynucleotide agent as described herein and an N-acetylgalactosamine, subjects can be administered a therapeutic amount of about 10 to 100 or about 0.5 to about 10 mg/kg of antisense polynucleotide agent. Values and ranges intermediate to the recited values are also intended to be part of this invention.

For example, subjects can be administered a therapeutic amount of antisense polynucleotide agent, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg. Values and ranges intermediate to the recited values are also intended to be part of this invention.

The antisense polynucleotide agent can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the antisense polynucleotide agent can reduce LECT2 levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the antisense polynucleotide agent, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on LECT2 expression, a composition according to the invention or a pharmaceutical composition prepared therefrom can enhance the quality of life.

An antisense polynucleotide agent of the invention may be administered in "naked" form, or as a "free antisense polynucleotide agent." A naked antisense polynucleotide agent is administered in the absence of a pharmaceutical composition. The naked antisense polynucleotide agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the antisense polynucleotide agent can be adjusted such that it is suitable for administering to a subject.

Alternatively, an antisense polynucleotide agent of the invention may be administered as a pharmaceutical composition, such as an antisense polynucleotide agent liposomal formulation.

The invention further provides methods and uses of an antisense polynucleotide agent or a pharmaceutical composition thereof (including methods and uses of an antisense polynucleotide agent or a pharmaceutical composition comprising an antisense polynucleotide agent and an anti-LECT2 antibody, or antigen-bidning fragment thereof) for treating a subject that would benefit from reduction and/or inhibition of LECT2 expression, e.g., a subject having a LECT2-associated disease, in combination with other pharmaceuticals and/or other therapeutic methods, e.g., with known pharmaceuticals and/or known therapeutic methods, such as, for example, those which are currently employed for treating these disorders. For example, in certain embodiments, an antisense polynucleotide agent targeting LECT2 is administered in combination with, e.g., an agent useful in treating a LECT2-associated disease as described elsewhere herein.

The antisense polynucleotide agent (and/or an anti-LECT2 antibody) and an additional therapeutic agent and/or treatment may be administered at the same time and/or in the same combination, e.g., parenterally, or the additional therapeutic agent can be administered as part of a separate composition or at separate times and/or by another method known in the art or described herein.

The present invention also provides methods of using an antisense polynucleotide agent of the invention and/or a composition containing an antisense polynucleotide agent of the invention to reduce and/or inhibit LECT2 expression in a cell. In other aspects, the present invention provides an antisense polynucleotide agent of the invention and/or a composition comprising an antisense polynucleotide agent of the invention for use in reducing and/or inhibiting LECT2 expression in a cell. In yet other aspects, use of an antisense polynucleotide agent of the invention and/or a composition comprising an antisense polynucleotide agent of the invention for the manufacture of a medicament for reducing and/or inhibiting LECT2 expression in a cell are provided.

The methods and uses include contacting the cell with an antisense polynucleotide agent, e.g., a antisense polynucleotide agent, of the invention and maintaining the cell for a time sufficient to obtain antisense inhibition of a LECT2 gene, thereby inhibiting expression of the LECT2 gene in the cell.

Reduction in gene expression can be assessed by any methods known in the art. For example, a reduction in the expression of LECT2 may be determined by determining the mRNA expression level of LECT2 using methods routine to one of ordinary skill in the art, e.g., Northern blotting, qRT-PCR, by determining the protein level of LECT2 using methods routine to one of ordinary skill in the art, such as Western blotting, immunological techniques, flow cytometry methods, and/or ELISA.

In the methods and uses of the invention the cell may be contacted in vitro or in vivo, i.e., the cell may be within a subject.

A cell suitable for treatment using the methods of the invention may be any cell that expresses a LECT2 gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

LECT2 expression may be inhibited in the cell by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%.

The in vivo methods and uses of the invention may include administering to a subject a composition containing an antisense polynucleotide agent, where the antisense polynucleotide agent includes a nucleotide sequence that is complementary to at least a part of an RNA transcript of the LECT2 gene of the mammal to be treated. When the organism to be treated is a mammal such as a human, the composition can be administered by any means known in the art including, but not limited to subcutaneous, intravenous, oral, intraperitoneal, or parenteral routes, including intracranial (e.g., intraventricular, intraparenchymal and intrathecal), intramuscular, transdermal, airway (aerosol), nasal, rectal, and topical (including buccal and sublingual) administration. In certain embodiments, the compositions are administered by subcutaneous or intravenous infusion or injection.

In some embodiments, the administration is via a depot injection. A depot injection may release the antisense polynucleotide agent in a consistent way over a prolonged time period. Thus, a depot injection may reduce the frequency of dosing needed to obtain a desired effect, e.g., a desired inhibition of LECT2, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the antisense polynucleotide agent to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of a LECT2 gene in a mammal, e.g., a human The present invention also provides a composition comprising an antisense polynucleotide agent that targets a LECT2 gene in a cell of a mammal for use in inhibiting expression of the LECT2 gene in the mammal. In another aspect, the present invention provides use of an antisense polynucleotide agent that targets a LECT2 gene in a cell of a mammal in the manufacture of a medicament for inhibiting expression of the LECT2 gene in the mammal.

The methods and uses include administering to the mammal, e.g., a human, a composition comprising an antisense polynucleotide agent that targets a LECT2 gene in a cell of the mammal and maintaining the mammal for a time sufficient to obtain antisense inhibition of the mRNA transcript of the LECT2 gene, thereby inhibiting expression of the LECT2 gene in the mammal.

Reduction in gene expression can be assessed by any methods known it the art and by methods, e.g. qRT-PCR, described herein. Reduction in protein production can be assessed by any methods known it the art and by methods, e.g., ELISA or Western blotting, described herein. In one embodiment, a puncture liver biopsy sample serves as the tissue material for monitoring the reduction in LECT2 gene and/or protein expression. In another embodiment, a blood sample serves as the tissue material for monitoring the reduction in LECT2 gene and/or protein expression. Suitable assays are further described in the Examples section below.

A. LECT2 Amyloidosis

In embodiments, the disorder related to LECT2 expression is an amyloidosis, e.g., a LECT2 amyloidosis. LECT2 amyloidosis has been described in several clinical studies. See, e.g., Benson, M. D. et al (2008) *Kidney International*, 74: 218-222; Murphy, C. L. et al. (2010) *Am J Kidney Dis*, 56(6):1100-1107; Larsen, C. P. et al. (2010) *Kidney Int.*, 77(9):816-819; Holanda, D. G. et al. (20011) *Nephrol. Dial. Transplant.*, 26 (1): 373-376; and Sethi, S. et al. (2012) *Kidney International* 82, 226-234 (hereinafter Sethi et al.).

Clinical and pathological features of LECT2 amyloidosis mimic those of amyloid light chain (AL) amyloidosis. These symptoms include, e.g., symptoms of kidney disease and renal failure, e.g., fluid retention, swelling, and shortness of breath. Amyloidosis may affect the heart, peripheral nervous system, gastrointestinal tract, blood, lungs and skin. Heart complications include, e.g., heart failure and irregular heart beat. Other symptoms include, e.g., stroke, gastrointestinal disorders, enlarged liver, diminished spleen function, diminished function of the adrenal and other endocrine glands, skin color change or growths, lung problems, bleeding and bruising problems, fatigue and weight loss. In embodiments, the methods described herein are associated with improvement in one or more symptoms described herein.

Methods for diagnosis of amyloidosis, e.g., LECT2 amyloidosis, are described, e.g., in Leung, N. et al. (2010) *Blood*, published online Sep. 4, 2012; DOI 10.1182/blood-2012-03-413682; Shiller, S. M. et al. (2011). Laboratory Methods for the Diagnosis of Hereditary Amyloidoses, Amyloidosis—Mechanisms and Prospects for Therapy, Dr. Svetlana Sarantseva (Ed.), ISBN: 978-953-307-253-1; Sethi et al. (see above) and in U.S. Patent Application Publication No. 20100323381.

Based on the results provided by Sethi et al., LECT2 amyloidosis accounts for a significant percentage of cases of renal amyloidosis. See Table 1 of Sethi et al., which shows that 26 out of 127 cases of renal amyloidosis studied by laser microdissection and mass spectrometry of renal biopsy and/or nephrectomy specimens were determined to be of the LECT2 amyloid type. Sethi et al. further report that apolipoprotein E protein and serum amyloid P component (SAP) were also present in all cases of LECT2 amyloidosis.

In embodiments, the amyloidosis, e.g., the LECT2 amyloidosis, involves systemic amyloid deposition. In embodiments, the amyloidosis, e.g., the LECT2 amyloidosis, is localized entirely or predominately to a particular tissue or organ (e.g., to the kidney or liver).

In embodiments, the amyloidosis, e.g., the LECT2 amyloidosis, is hereditary.

In embodiments, a LECT2 amyoidosis is diagnosed using analysis of a sample from the subject (e.g., a biopsy sample). In embodiments, the biopsy sample is a renal biopsy. In embodiments, the sample is a nephrectomy sample. In embodiments, the sample is from a liver biopsy or from other resected liver tissue. In embodiments, the sample is analyzed using methods selected from one or more of immunohistochemistry, LECT2 immunoassay, electron microscopy, laser microdissection, and mass spectrometry. In embodiments, the LECT2 amyloidosis is diagnosed using laser microdissection and mass spectrometry.

In embodiments, the amyloidosis, e.g., the LECT2 amyloidosis, affects the kidney, e.g., involves amyloid deposition in the kidney. In embodiments, kidney function is compromised as a result of the amyloidosis. In embodiments, the subject suffers from one or more of fluid retention, swelling, and shortness of breath. In embodiments, the subject has nephrotic syndrome. In embodiments, the subject suffers from proteinuria. In embodiments, the subject has renal failure.

In embodiments, the amyloidosis, e.g., the LECT2 amyloidosis, affects the liver, e.g., involves amyloid deposition in the liver. In embodiments, liver function is compromised as a result of the amyloidosis. In embodiments, the subject has hepatitis, e.g., chronic hepatitis. In embodiments, the hepatitis is a viral hepatitis.

LECT2 amyloidosis has been found to be particularly prevalent in Mexican Americans and has also been associated with homozygosity for the G allele of the LECT2 gene that encodes valine at position 40 in the mature protein (amino acid 58 in the unprocessed protein). See, e.g., Benson, M. D. et al. (2008) *Kidney International*, 74: 218-222; Murphy, C. L. et al. (2010) *Am J Kidney Dis*, 56(6):1100-1107.

In some embodiments, the subject is of Mexican descent. In some embodiments, the subject is a Mexican American.

In embodiments, the subject carries the G allele of the LECT2 gene that encodes valine at position 40 in the mature protein (amino acid 58 in the unprocessed protein). In embodiments, the subject is homozygous for the G allele (G/G genotype). In embodiments, a LECT2 protein expressed in the subject has valine at position 40 in the mature protein (or at amino acid 58 in the unprocessed protein).

In some embodiments, the method decreases LECT2 expression. In embodiments, the decrease in LECT2 expression is assessed relative to the level in the same individual prior to the treatment. In some embodiments, the method is shown to decrease LECT2 expression by comparing the levels of LECT2 expression in a treated subject (or group of subjects) with the levels in a control subject (or group of subjects), e.g., an untreated subject (or group of subjects) or a subject (or group of subjects) treated with a control treatment (e.g., an iRNA (e.g., a dsRNA) that does not target LECT2).

In embodiments, the method reduces amyloid deposition, e.g., deposition of amyloid comprising a LECT2 protein or a portion thereof. In embodiments, the protein is a wild type protein. In embodiments, the protein is a human LECT2 protein, or a portion thereof, that includes valine at position 40 (position 40 of the mature, secreted protein, or at amino acid 58 in the unprocessed protein, as described herein). In embodiments, the method decreases the size, number, and/or extent of amyloid deposits.

In embodiments, the method decreases one or more symptoms associated with amyloid deposition.

In some embodiments, the antisense polynucleotide is administered in a form that targets the dsRNA to a particular organ or tissue to inhibit amyloid deposition in the organ or tissue.

In some embodiments, the antisense polynucleotide is targeted to the liver. In some embodiments, the dsRNA is conjugated to a ligand, e.g., a GalNAc ligand (e.g., a GalNAc ligand as described herein) that targets the dsRNA to the liver (e.g., to hepatocytes).

Also provided herein is a method of reducing amyloid deposition, the method comprising administering antisense polynucleotide agent as disclosed herein to a subject in need thereof (e.g., a subject having, suspected of having, or at risk for developing a LECT2 amyloidosis). In embodiments, the method decreases (e.g., prevents or diminishes) the size, number, and/or extent of amyloid deposits. The size, number, and/or extent of amyloid deposits may be assessed using any method known in the art (e.g., immunoassay, immunohistochemistry, mass spectrometry). The reduction of amyloid deposition may involve a decrease in amyloid deposition (e.g., size, number, and/or extent of amyloid deposits) of at least 5%, 10%, 15%, 20%, 25%, 30%, 35%, 40%, 45%, 50% or more.

In the methods provided herein, the antisense polynucleotide and compositions thereof are administered in a therapeutically effective amount.

B. Rheumatoid Arthritis

Rheumatoid arthritis is also a disorder related to LECT2 expression. In particular, in a Japanese population, it was found that possession of one A allele of the LECT2 gene that encodes isoleucine at position 40 in the mature protein (or amino acid 58 in the unprocessed protein) was found to increase the overall risk of developing rheumatoid arthritis. Possessing two A alleles was strongly associated with disease severity. See Kameoka, Y. et al. (2000) *Arth Rheum*, 43(6):1419-20.

In one embodiment of the methods provided herein, the disorder related to LECT2 expression is rheumatoid arthritis. In one embodiment, the antisense polynucleotide agent inhibits LECT2 expression in a subject having rheumatoid arthritis. In some such embodiments, the antisense polynucleotide agent inhibits LECT2 expression in synovial tissue and/or in synovial fluid-derived cells (e.g., mononuclear cells and fibroblasts). In some embodiments, the antisense polynucleotide agent targets an mRNA that encodes isoleucine at position 40 in the mature protein (amino acid 58 in the unprocessed protein).

C. Liver Injury

LECT2 expression can increase during acute liver injury.

In one embodiment of the methods provided herein, the disorder related to LECT2 expression is acute liver injury. In embodiments, the antisense polynucleotide agent modulates (e.g., increases or decreases) LECT2 expression. In embodiments, the antisense polynucleotide agent modulates LECT2 expression in the liver. In embodiments, the antisense polynucleotide agent decreases LECT2 expression in the liver. In embodiments, the antisense polynucleotide agent increases LECT2 expression in the liver.

D. Combination Therapies

In another aspect, the present invention provides uses of a therapeutically effective amount of an antisense polynucleotide agent of the invention and an additional therapeutic agent, for treating a subject, e.g., a subject that would benefit from a reduction and/or inhibition of LECT2 expression.

In embodiments, an antisense polynucleotide agent (e.g., a dsRNA) disclosed herein is administered in combination with an additional therapeutic agent (e.g., one or more additional therapies) known to be effective in treating a disorder related to LECT2 expression (e.g., a LECT2 amyloidosis) or a symptom of such a disorder. The antisense polynucleotide agent may be administered before, after, or concurrent with the additional therapeutic agent. In embodiments, the antisense polynucleotide agent is administered before the additional therapeutic agent. In embodiments, the antisense polynucleotide agent is administered after the additional therapeutic agent. In embodiments, the antisense polynucleotide agent is administered concurrent with the additional therapeutic agent.

In another aspect, the invention provides methods of preventing at least one symptom in a subject having a disorder that would benefit from reduction in LECT2 expression, e.g., a LECT2-associated disease, e.g., amyloidosis, e.g. a LECT2 amyloidosis (ALECT2). The methods include administering to the subject a prophylactically effective amount of an antisense polynucleotide agent targeting a LECT2 gene or a pharmaceutical composition comprising an antisense polynucleotide agent targeting a LECT2 gene, and an additional therapeutic agent, thereby preventing at least one symptom in the subject having a disorder that would benefit from reduction in LECT2 expression.

In another aspect, the present invention provides methods of treating a subject having a disorder that would benefit from reduction in LECT2 expression, e.g., a LECT2-associated disease, e.g., amyloidosis, e.g. a LECT2 amyloidosis (ALECT2), which include administering to the subject, e.g., a human, a therapeutically effective amount of an antisense polynucleotide agent targeting a LECT2 gene or a pharmaceutical composition comprising an antisense polynucleotide agent targeting a LECT2 gene, and an additional therapeutic agent, thereby treating the subject having a disorder that would benefit from reduction in LECT2 expression.

In another aspect, the present invention provides uses of an antisense polynucleotide agent of the invention targeting a LECT2 gene or a pharmaceutical composition comprising an antisense polynucleotide agent targeting a LECT2 gene in the manufacture of a medicament for use in combination with an additional therapeutic agent, for treating a subject, e.g., a subject that would benefit from a reduction and/or inhibition of LECT2 expression, e.g., a LECT2-associated disease, e.g., amyloidosis, e.g. a LECT2 amyloidosis (ALECT2).

In yet another aspect, the invention provides uses of an antisense polynucleotide agent of the invention, and an additional therapeutic agent, for preventing at least one symptom in a subject suffering from a disorder that would benefit from a reduction and/or inhibition of LECT2 expression, such as a LECT2-associated disease, e.g., amyloidosis, e.g. a LECT2 amyloidosis (ALECT2).

In a further aspect, the present invention provides uses of an antisense polynucleotide agent of the invention in the manufacture of a medicament for use in combination with an additional therapeutic agent, for preventing at least one symptom in a subject suffering from a disorder that would benefit from a reduction and/or inhibition of LECT2 expression, such as a LECT2-associated disease, e.g., amyloidosis, e.g. a LECT2 amyloidosis (ALECT2).

In one embodiment, an antisense polynucleotide agent targeting LECT2 is administered to a subject having a LECT2-associated disease such that LECT2 levels, e.g., in a cell, tissue, blood, urine or other tissue or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more and, subsequently, an additional therapeutic (as described below) is administered to the subject.

In embodiments, the additional therapeutic agent is a second therapy. The agent and the additional therapeutic agent can be administered in combination in the same composition or the additional therapeutic agent can be administered as part of a separate composition.

In some embodiments, the second therapy is a non-antisense polynucleotide agent therapeutic agent that is effective to treat the disorder or symptoms of the disorder.

In some embodiments, the disorder to be treated by the compositions or methods disclosed herein is a LECT2 amyloidosis that affects kidney function, e.g., through amyloid deposition in the kidney. In some such embodiments, the agent is administered in conjunction with a therapy that supports kidney function (e.g., dialysis, a diuretic, an angiotensin converting enzyme (ACE) inhibitor, an angiotensin receptor blocker (ARB), or dialysis).

In some embodiments, the disorder to be treated by the compositions or methods disclosed herein is a LECT2 amyloidosis involving amyloid deposits in the liver. In some such embodiments, the agent is administered in conjunction with a therapy that supports liver function.

In some embodiments, the disorder to be treated by the compositions or methods disclosed herein is a LECT2 amyloidosis, and the agent is administered in conjunction with removal of all or part of the organ(s) affected by the amyloidosis (e.g., resection of all or part of kidney or liver tissue affected by the amyloidosis). The removal is optionally conducted in conjunction with a replacement of all or part of the organ removed (e.g., in conjunction with a kidney or liver organ transplant).

In some embodiments, the additional therapeutic agent is an anti-LECT2 antibody, or antigen binding fragment thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the antisense polynucleotide agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Antisense Synthesis

The antisense polynucleotides targeting LECT2 were synthesized using standard synthesis methods known in the art.

A detailed list of modified and unmodified antisense molecules targeting LECT2 is shown in Table 3, including the starting position and mRNA sequence of the antisense oligonucleotide relative to SEQ ID NO: 1.

Example 2

In Vitro Screening

In vitro screening of the antisense polynucleotides was performed by transfecting human primary hepatocytes with a single 500 nM dose of an antisense LECT2 polynucleotide using methods known in the art. 32000 cells/well in a 96 well plate were transfected for 24 hours in 0.4 µl RNAiMAX/well. A single dose transfection screen in cells transfected with the indicated antisense polynucleotide is shown in Table 4. The relative LECT2 mRNA expression relative to a mock transfected control was determined.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |

TABLE 2-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| As | adenosine-3'-phosphorothioate |
| a | 2'-O-methyladenosine-3'-phosphate |
| as | 2'-O-methyladenosine-3'-phosphorothioate |
| C | cytidine-3'-phosphate |
| dA | 2'-deoxyadenosine-3'-phosphate |
| dAs | 2'-deoxyadenosine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| c | 2'-O-methylcytidine-3'-phosphate |
| cs | 2'-O-methylcytidine-3'-phosphorothioate |
| dC | 2'-deoxycytidine-3'-phosphate |
| dCs | 2'-deoxycytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| g | 2'-O-methylguanosine-3'-phosphate |
| gs | 2'-O-methylguanosine-3'-phosphorothioate |
| dG | 2'-deoxyguanosine-3'-phosphate |
| dGs | 2'-deoxyguanosine-3'-phosphorothioate |
| T | 5'-methyluridine-3'-phosphate |
| f | 2'-fluoro-5-methyluridine-3'-phosphate |
| Tfs | 2'-fluoro-5-methyluridine-3'-phosphorothioate |
| Ts | 5-methyluridine-3'-phosphorothioate |
| t | 2'-O-methyl-5-methyluridine-3'-phosphate |
| ts | 2'-O-methyl-5-methyluridine-3'-phosphorothioate |
| dT | 2'-deoxythymidine-3'-phosphate |
| dTs | 2'-deoxythymidine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| u | 2'-O-methyluridine-3'-phosphate |
| us | 2'-O-methyluridine-3'-phosphorothioate |
| dU | 2'-deoxyuridine-3'-phosphate |
| dUs | 2'-deoxyuridine-3'-phosphorothioate |
| s | phosphorothioate linkage |
| N | any nucleotide (G, A, C, T or U) |
| L96 | N-[tris(GalNAc-alkyl)-amidodecanoyl)]-4-hydroxyprolinol Hyp-(GalNAc-alkyl)3 |
| (dt) | deoxy-thymine |
| (5MdC) | 5'-methyl-deoxycytidine-3'-phosphate |
| (5MdC)s | 5'-methyl-deoxycytidine-3'-phosphorothioate |

TABLE 3

Antisense polynucleotides targeting LECT2.

| Oligo | SEQ ID NO: | Modified Antisense Sequence (5' to 3') | Pos | SEQ ID NO: | mRNA Target Sequence | SEQ ID NO: | Unmodified Antisense Sequence |
|---|---|---|---|---|---|---|---|
| A-133875.1 | 13 | ususcsusasdAsdTsdAsdTsdTs(5MdC)sdAsdTsdGsgsasusasg | 12 | 109 | CUAUCCUGGAAUAUUAGAA | 205 | UUCUAAUAUUCCAUGGAUAG |
| A-133876.1 | 14 | gsasgscsasdAsdGsdTs(5MdC)sdAsdAsdGsdTsdTs(5MdC)susasasusa | 24 | 110 | UAUUAGAACUUGACUUGCUC | 206 | GAGCAAGUCAAGUUCUAAUA |
| A-133877.1 | 15 | asasgsasgsdGsdAsdTsdGsdGsdAsdGs(5MdC)sdAsdAsgsuscsasa | 33 | 111 | UUGACUUGCUCCAUCCCUCU | 207 | AAGAGGAUGGAGCAAGUCAA |
| A-133878.1 | 16 | ascsasasasdAsdAsdAsdGsdTsdTsdAsdAsdGsdAsgsgsasusg | 44 | 112 | CAUCCCUCUUAAACUUUUGU | 208 | ACAAAAGUUUAAGAGGAUG |
| A-133879.1 | 17 | usususasgsdTsdGsdTsdGsdAsdGsdAs(5MdC)sdAs(5MdC)sasasasasa | 57 | 113 | UUUUUGUCUCUCACACUAAA | 209 | UUUAGUGUGAGACACAAAAA |
| A-133880.1 | 18 | uscsuscsasdTsdTs(5MdC)sdTsdTsdTsdAsdGsdTsgsusgsasg | 66 | 114 | CUCACACUAAAGAAAUGAGA | 210 | UCUCAUUCUUUAGUGUGAG |
| A-133881.1 | 19 | gsasasasusu(5MdC)sdTsdGs(5MdC)sdAsdTs(5MdC)sdTs(5MdC)sdTscsasususug | 78 | 115 | AAAUGAGAUGCAGAAUUC | 211 | GAAUUCUGCAUCCUCAUUU |
| A-133882.1 | 20 | usasususudAsdGs(5MdC)sdTsdAsdGsdGsdAsdAsususcsusg | 90 | 116 | CAGAAUUCUAAGGCUAGGAAGU | 212 | UAUUUAGCCUUAGAAUUCUG |
| A-133883.1 | 21 | ascsususcs(5MdC)sdTsdAsdGs(5MdC)sdTsdAsdTsdTsdTsasgscscsusa | 100 | 117 | AGGCUAAAUAGCUAGGAAGU | 213 | ACUUCCUAGCUAUUUAGCCU |
| A-133884.1 | 22 | gsusususgsdAsdAsdAsdTsdGsdAsdTsdAs(5MdC)sdTsuscscsusa | 112 | 118 | UAGGAAGUAUCAUUCAAAC | 214 | GUUUGAAUGAAUACUUCCUA |
| A-133885.1 | 23 | asasusasusudTs(5MdC)sdAsdAsdGsdTsdTsdGsdAsasusgsasa | 121 | 119 | UUCAUUCAAACUUGAAUAUU | 215 | AAUAUUCAAGUUUGAAUGAA |
| A-133886.1 | 24 | uscsuscusudTsdGsdAsdGsdAsdAsdAsdTsdAsususcasa | 132 | 120 | UUGAAUAUUCUCAAAGAGA | 216 | UCUCUUUGAAGAAUAUUCAA |
| A-133887.1 | 25 | gsususgscs(5MdC)s(5MdC)s(5MdC)sdAs(5MdC)sdAs(5MdC)sdTs(5MdC)sdTscscsususu | 145 | 121 | AAAGAGAGUGUGGGGCAAC | 217 | GUUGCCCCACACUCUCUUU |
| A-133888.1 | 26 | csusgsasususdTsdAsdGsdAsdGsdTsdGs(5MdC)scscscsasc | 154 | 122 | GUGGGGCAACUCUAAUCAG | 218 | CUGAUUAGAGUUGCCCCAC |
| A-133889.1 | 27 | usasgsususdTs(5MdC)sdTsdTs(5MdC)sdTs(5MdC)sdTs(5MdC)sdTgsGsasususasg | 166 | 123 | CUAAUCAGAGGAAGAAACUA | 219 | UAGUUUCUUCCUCUGAUUAG |
| A-133890.1 | 28 | usususascs(5MdC)sdTsdTsdTsdAsdGsdTsdTsdAsdAsdAsususcsusu | 177 | 124 | AAGAAACUAAAGGAAGUAAA | 220 | UUUACUUCCUUUAGUUUCUU |
| A-133891.1 | 29 | asascsasus(5MdC)sdTsdGsdGsdTsdTsdTsdTsdAs(5MdC)sususcscsu | 187 | 125 | AGGAAGUAAAACCAGAUGUU | 221 | AACAUCUGGUUUUACUUCCU |
| A-133892.1 | 30 | gsgsgscscsasdAsdGsdGsdGsdGsdAsdGsdGs(5MdC)sdTsusgsgsu | 200 | 126 | AGAUGUUUCCACCAAAGCC | 222 | GGCUUUGGUGGAAAACAUCU |
| A-133893.1 | 31 | gscscsscsasasdAsdAsdGsdGsdGsdGs(5MdC)sdTsusgsgsu | 211 | 127 | ACCAAAGCCCUCCUUUUGGC | 223 | GCCAAAAGGAGGGCUUUGGU |
| A-133894.1 | 32 | asasasusususcsasdAsdGs(5MdC)sdGsdAsdAsdAsdTs(5MdC)sdAsgsascscsa | 221 | 128 | UCCUUUUGGCUGUCUGAUU | 224 | AAUCAGACCAGCCAAAAGGA |
| A-133895.1 | 33 | gsusgsgscsgsdGsdTsdAsdGsdAsdAsdAsdTs(5MdC)sdAsgsascscsa | 231 | 129 | UGGCUGUCUGAUUUCUACCGGAC | 225 | GUGCGGUAGAAAUCAGACCA |
| A-133896.1 | 34 | asusgsgscs(5MdC)s(5MdC)sdTsdGs(5MdC)s(5MdC)sdAsdGsdTs(5MdC)sdGsdGsCscsgsgsusa | 243 | 130 | UACCGCACUGGCCAGGGCCAU | 226 | AUGGCCCUGCCAGUGCGGUA |

TABLE 3-continued

Antisense polynucleotides targeting LECT2.

| Oligo | SEQ ID NO: | Modified Antisense Sequence (5' to 3') | Pos | mRNA Target Sequence | SEQ ID NO: | Unmodified Antisense Sequence |
|---|---|---|---|---|---|---|
| A-133897.1 | 35 | usasusasusdTsdAsdGs(5MdC)s(5MdC)sdAsdTsdGdGsdGscscscsusg | 254 | CAGGGCCAUGGGCUAAAUAUA | 227 | UAUAUUAGCCAUGGCCCUG |
| A-133898.1 | 36 | csusustugscss(5MdC)sdTsdGsdAs(5MdC)sdAs(5MdC)sdAsdTsdAsdTsasususasasg | 266 | CUAAUAUGUGCUGGCAAG | 228 | CUUGCCAGCACAUAUUAG |
| A-133899.1 | 37 | csasususgsdGsdAsdAsdGsdAs(5MdC)sdTsdTsdGs(5MdC)scsasgscsa | 276 | UGCUGGCAAGUCUUCCAAUG | 229 | CAUUGGAAGACUUGCCAGCA |
| A-133900.1 | 38 | ascsgsguscs(5MdC)sdGsdGsdAsdTs(5MdC)sdTs(5MdC)sdAsdTsusgsgsasa | 288 | UUCCAAUGAGAUCCGGACGU | 230 | ACGUCCGGAUCUCAUUGGAA |
| A-133901.1 | 39 | asusgsgscsdGsdGsdTs(5MdC)sdAs(5MdC)sdAs(5MdC)sdGsdTscscsgsgsa | 299 | UCCGGACGUGUGACCGCCAU | 231 | AUGGCGGUCACACGUCCGGA |
| A-133902.1 | 40 | gsuscscsas(5MdC)sdAsdGs(5MdC)s(5MdC)sdAsdTsdGsdGs(5MdC)sgsgsuscsa | 309 | UGACCGCCAUGGCUGUGGAC | 232 | GUCCACAGCCAUGGCGGUCA |
| A-133903.1 | 41 | gsasgscsasdGsdAsdGsdTsdAs(5MdC)sdTsdGsdTs(5MdC)scsasccsasg | 321 | CUGUGGACAGUACUCUGCUC | 233 | GAGCAGAGUACUGUCCACAG |
| A-133904.1 | 42 | usgsascsusdTs(5MdC)sdTsdTsdTsdGsdAsdGs(5MdC)sdAsgsasgsusa | 331 | UACUCUGCUCAAAGAAGUCA | 234 | UGACUUCUUUGAGCAGAGUA |
| A-133905.1 | 43 | gsusgsasgsgs(5MdC)s(5MdC)sdTs(5MdC)sdTsdGsdAs(5MdC)sdTsuscsusususu | 341 | AAAGAAGUCAGAGGCCUCAC | 235 | GUGAGGCCUCUGACUUCUUU |
| A-133906.1 | 44 | uscscsascsdAs(5MdC)s(5MdC)sdTsdGsdGsdGsdTsdGsdAsgsgscscscsu | 352 | AGGCCUCACCAGGGUGGA | 236 | UCCACACCCUGGUGAGGCCU |
| A-133907.1 | 45 | gsasgscsas(5MdC)sdAsdAsdGsdAsdTsdGs(5MdC)s(5MdC)sasccsascsc | 364 | GGUGUGCAUCUUGCUGCUC | 237 | GAGCACAAGAUGCCACACC |
| A-133908.1 | 46 | asgsasuscs(5MdC)sdAsdGs(5MdC)sdAs(5MdC)sdAsdGsdGsdAsuscsasasgsa | 374 | UCUUGUGCUCUGCUGGAUCU | 238 | AGAUCCAGCAGCAGCACAAGA |
| A-133909.1 | 47 | usgscsgsusdAs(5MdC)sdAs(5MdC)sdAs(5MdC)sdGsdGsdAsuscscsasca | 386 | CUGGAUCUACUGUGUACGCA | 239 | UGCGUACACAGUAGAUCCAG |
| A-133910.1 | 48 | csaasgsusgsdAsdAsdTsdGsdGsdGs(5MdC)sdGsdTsascsasasca | 396 | UGUGUACGCACCAUUCACUG | 240 | CAGUGAAUGGUGCGUACACA |
| A-133911.1 | 49 | csasascsasasdTs(5MdC)sdAsdTsdTs(5MdC)sdGsdGsdTsgsasasusg | 407 | CAUUCACUGGAAUGAUUGUG | 241 | CACAAUCAUUCCAGUGAAUG |
| A-133912.1 | 50 | ususcsuscs(5MdC)sdTsdGsdGs(5MdC)s(5MdC)sdAs(5MdC)sdAasususcsasu | 418 | AUGAUUGUGGCCCAGAGAA | 242 | UUCUCCUGGCCCACAAUCAU |
| A-133913.1 | 51 | gsususususdGsdAsdAsdGsdGsdTsdTsdTscsususcscsu | 431 | AGGAGAAACCUUAUCAAAAC | 243 | GUUUUGAUAAGGUUUCUCCU |
| A-133914.1 | 52 | usasgscsasdTs(5MdC)sdTsdTsdGsdTsdTsdGsdTsgsasususa | 441 | UUAUCAAAACAAGAAUGCUA | 244 | UAGCAUUCUUGUUUUGAUAA |
| A-133915.1 | 53 | cscsasususdAsdTsdGsdTsdTsdAs(5MdC)sdAsususcsusu | 451 | AAGAAUGCUAUCAAUAUGG | 245 | CCAUAUUGAUAGCAUUCUU |
| A-133916.1 | 54 | gsasasusudTs(5MdC)sdGsdAsdAs(5MdC)sdAs(5MdC)sdAsususasasusu | 463 | AAUAUGGUGUUCGAAUAUC | 246 | GAUAUUCGAACACCAUAUU |
| A-133917.1 | 55 | asasasascscsdTs(5MdC)sdTsdTs(5MdC)s(5MdC)sdAsdGsdAsdAsasususcsg | 475 | CGAAUAUCUGGAAGAGGUUU | 247 | AAACCUCUUCCAGAUAUUCG |
| A-133918.1 | 56 | ususususgsdAs(5MdC)sdAs(5MdC)sdAsdAsdAsdAs(5MdC)scsuscsusu | 486 | AAGAGGUUUUGACAAAA | 248 | UUUUGACACAAAACCUCU |
| A-133919.1 | 57 | usgsusasusdGsdGsdAsdTsdTsdTsdGsdGsdAscsascsasa | 495 | UUGUGCAAAAUGUUCUCA | 249 | UGUAGAACAUUUGACACA |
| A-133920.1 | 58 | ususasasusdTsdGsdGs(5MdC)sdTsdTsdAsdAsdTsdGsusasgsasa | 508 | UUCUACAUUAAGCCAAUUAA | 250 | UUAAUUGGCUUAAUGUAGAA |

TABLE 3-continued

Antisense polynucleotides targeting LECT2.

| Oligo | SEQ ID NO: | Modified Antisense Sequence (5' to 3') | Pos | SEQ ID NO: | mRNA Target Sequence | SEQ ID NO: | Unmodified Antisense Sequence |
|---|---|---|---|---|---|---|---|
| A-133921.1 | 59 | cscsusasgsdTsdAsdTsdAs(5MdC)sdTsdTsdAsdAsdTsgsgscsusu | 517 | 155 | AAGCCAAUUAAGUAUAAAGG | 251 | CCUUUAUACUUAAUUGGCUU |
| A-133922.1 | 60 | ususcsususdAsdAsdGsdGsdAs(5MdC)sdTsususasusa | 529 | 156 | UAUAAAGGUCCUAUUAAGAA | 252 | UUCUUAAUAGGACCUUUAUA |
| A-133923.1 | 61 | asgsususudTsdTs(5MdC)sdTs(5MdC)sdTs(5MdC)sdTsdTs(5MdC)sususasasu | 541 | 157 | AUUAAGAAGGAGAAAAACU | 253 | AGUUUUCUCCCCUUCUUAAU |
| A-133924.1 | 62 | asusasgsasdGsdTsdTs(5MdC)sdTs(5MdC)s(5MdC)sdAsdAsdGsdTsdTsusususcsu | 552 | 158 | AGAAAAACUUGGAACUCUAU | 254 | AUAGAGUUCCAAGUUUUUCU |
| A-133925.1 | 63 | gscsasasgsdGsdGsdGs(5MdC)sdAsdAsdTsdAsdGsdAsdGsususcsca | 561 | 159 | UGGAACUCUAUUGCCCUGC | 255 | GCAAGGGCAAUAGAGUUCCA |
| A-133926.1 | 64 | asusasasas(5MdC)sdTsdTsdTs(5MdC)sdTsdGs(5MdC)sdAsdAsgsgsgscsa | 572 | 160 | UGCCCUUGCAGAAGUUUAU | 256 | AUAAACUUCUGCAAGGGCA |
| A-133927.1 | 65 | asususcsusdAsdTsdGs(5MdC)sdAsdGsdGsdAsdTsasasascsu | 585 | 161 | AGUUUAUCCUGCCAUACAAU | 257 | AUUGUAUGCCAGGAUAAACU |
| A-133928.1 | 66 | gscsascsusdTsdTs(5MdC)sdAsdTsdGsdTsdAsusgsccsca | 594 | 162 | UGGCAUACAAUCGCAUGUGC | 258 | GCACAUGCGAUUGUAUGCCA |
| A-133929.1 | 67 | asgsusususdTs(5MdC)sdAsdAsdTsdGsdTs(5MdC)sdAscsasusgsc | 606 | 163 | GCAUGUGCACAUUGAAAACU | 259 | AGUUUUCAAUGUGCACAUGC |
| A-133930.1 | 68 | ascsuscsgsdGsdGsdTs(5MdC)sdAs(5MdC)sdTs(5MdC)sdGsdAsgsusucsa | 617 | 164 | UUGAAAACUGUGACUCGAGU | 260 | ACUCGAGUCACAGUUUUCAA |
| A-133931.1 | 69 | csasgsusasdGsdGsdGs(5MdC)sdAs(5MdC)sdTs(5MdC)sdGsdAsgsusucsa | 627 | 165 | UGACUCGAGUGACCCUACUG | 261 | CAGUAGGGUCACUCGAGUCA |
| A-133932.1 | 70 | ususususascsdAsdGsdGsdTsdAsdGsdTs(5MdC)sdAsdGsdAsdTsdAs(5MdC)saagsgsgsg | 639 | 166 | CCCUACUGCAUACCUGUAAA | 262 | UUUACAGGUAUGCAGUAGGG |
| A-133933.1 | 71 | usgsgscscsdTs(5MdC)sdTsdGsdAs(5MdC)sdAsdTsdAs(5MdC)saasgsgsusa | 649 | 167 | UACCUGUAAAUCGAAGGCCA | 263 | UGGCCUUCGAUUUACAGGUA |
| A-133934.1 | 72 | asasgsgasdTs(5MdC)sdTsdGsdAs(5MdC)sdAsdTsdGsdAsdGsdAsuscsusgsa | 662 | 168 | AAGGCCAUGGUCAGAUCUU | 264 | AAGAUCUGACCAUGGCCUU |
| A-133935.1 | 73 | ususususdAsdAsdTsdTsdTsdGsdAsdGsdAsdGsdAsusscsusgsa | 673 | 169 | UCAGAUCUCAAAAUAUAAAA | 265 | UUUUAUAUUUUGAAGAUCUGA |
| A-133936.1 | 74 | ususasasgsdAsdTsdGsdTsdTsdTsdTsdTsdAsgsgsasusgsa | 683 | 170 | AAAAUAUAAAGUCAUCUAA | 266 | UUAAGAUGACUUUUAUAUU |
| A-133937.1 | 75 | csasuscscsdAsdGsdGsdTsdTsdTsdTsdAsggsasusga | 694 | 171 | UCAUCUAAAAACCUGGAUG | 267 | CAUCCAGGUUUUAAGAUGA |
| A-133938.1 | 76 | gsaasasgsgsdAsdTsdGsdTsdGsdAs(5MdC)sdAsdTs(5MdC)s(5MdC)sdAsdTs(5MdC)sasgsgsusu | 704 | 172 | AACCUGGAUGCAUACCCUUC | 268 | GAAGGGUAUGCAUCCAGGUU |
| A-133939.1 | 77 | asasususus(5MdC)sdTsTsdGsdGsdAsdAsdGsdAsdGsdAsdAsgsgsgsgu | 717 | 173 | ACCCUUCUCUCUUCCAGAAAUU | 269 | AAUUCUGGAAGAGAAGGGU |
| A-133940.1 | 78 | gsusgsgsdAs(5MdC)sdAs(5MdC)sdAsdAsdAsdAsdTsdTs(5MdC)sususgsasa | 726 | 174 | UUCAAGAAAAUUGUGUCAC | 270 | GUGAACACAAAUUUCUUGAA |
| A-133941.1 | 79 | csasususudTs(5MdC)sdTsdTs(5MdC)sdAsdAsdTsdGsdTsdGsdsasascsaac | 738 | 175 | GUGUUCACAAGGAAAAAUG | 271 | CAUUUUUCCUUGUGAACAC |
| A-133942.1 | 80 | csasuscscs(5MdC)sdTsdTs(5MdC)sdAsdTsdGs(5MdC)sdAsdTsdTsususuac | 750 | 176 | GAAAAAUGCAUGAAGGGAUG | 272 | CAUCCCUUCAUGCAUUUUUC |
| A-133943.1 | 81 | asusgsgsgsdTsdAsdTs(5MdC)s(5MdC)sdAsdTs(5MdC)s(5MdC)scsususcsa | 760 | 177 | UGAAGGGAUGAUACCCCAU | 273 | AUGGGGUAUCCAUCCCUUCA |

TABLE 3-continued

Antisense polynucleotides targeting LECT2.

| Oligo | SEQ ID NO: | Modified Antisense Sequence (5' to 3') | Pos | SEQ ID NO: | mRNA Target Sequence | SEQ ID NO: | Unmodified Antisense Sequence |
|---|---|---|---|---|---|---|---|
| A-133944.1 | 82 | asusgsuscsdAsdTsdGsdGsdAsdAsdAsdTsdGsgsgsgsusa | 772 | 178 | UACCCCAUUUUCCAUGACAU | 274 | AUGUCAUGGAAAAUGGGGUA |
| A-133945.1 | 83 | gsusasasusdAsdAsdTs(5MdC)sdAsdTsdGsdTs(5MdC)sdAsusgsgsasa | 781 | 179 | UUCCAUGACAUGAUUAUUAC | 275 | GUAAUAAUCAUGUCAUGGAA |
| A-133946.1 | 84 | asgsgscsasdTsdGs(5MdC)sdAsdAsdTsdGsdGsdTsasasusasa | 794 | 180 | UUAUUACACAUUGCAUGCCU | 276 | AGGCAUGCAAUGUGUAAUAA |
| A-133947.1 | 85 | gsusususdGsdAsdTsdAs(5MdC)sdAsdGsdGs(5MdC)sdAsusgscsasa | 804 | 181 | UUGCAUGCCUGAUCAAAAC | 277 | GUUUUGAUACAGGCAUGCAA |
| A-133948.1 | 86 | gsusascsgsdTsdGsdGsdAsdTsdGsdTsdTsusgsasusa | 815 | 182 | UAUCAAAACAUCUCACGUAC | 278 | GUACGUGAGAUGUUUUGAUA |
| A-133949.1 | 87 | usasasugsusdTsdTsdAsdTsdGsdAsdGsdGsdTsdAscsgsusgsa | 827 | 183 | UCACGUACCUCAUAAACAUA | 279 | UAUGUUUAUGAGGUACGUGA |
| A-133950.1 | 88 | csasusasgsgsdGsdTsdAsdTsdAsdTsdGsdTsusususasusg | 837 | 184 | CAUAAACAUAUACACCUAUG | 280 | CAUAGGUGUAUAUGUUUAUG |
| A-133951.1 | 89 | usususgsgsgsdTsdAs(5MdC)sdAsdTsdAsdGsgsusgsusa | 847 | 185 | UACACCUAUGUACCCACAAA | 281 | UUUGUGGGUACAUAGGUGUA |
| A-133952.1 | 90 | asusususasasdAsdAsdAsdTsdTsdTsdTsdAsdAsdTsasasasasa | 858 | 186 | ACCCACAAAAAUUUUUAAU | 282 | AUUAAAAAAUUUUGUGGGU |
| A-133953.1 | 91 | usususcscsusdTsdTsdTsdTsdAsdAsdAsdTsdTsasasasasa | 870 | 187 | UUUUUAAUAAAAAAAAGGAA | 283 | UUCCUUUUUUAUUAAAAA |
| A-133954.1 | 92 | asasascsus(5MdC)sdAsdAsdAsdAsdTsdTsdTs(5MdC)s(5MdC)sdTsususususu | 880 | 188 | AAAAAGGAAAAUUUGAGUUU | 284 | AAACUCAAAUUUCCUUUUU |
| A-133955.1 | 93 | usgsusususdCs(5MdC)sdTsdAsdAsdTsdTsdAsdAsdAs(5MdC)suscsasasa | 891 | 189 | UUUGAGUUUAAAUAGAAACA | 285 | UGUUUCUAUUUAAACUCAAA |
| A-133956.1 | 94 | csusususgscscsdAsdTsdTsdTsdTsdGsdTsdGsusususccsu | 904 | 190 | AGAAACAUGAUAAAUGCAAG | 286 | CUUGCAUUUAUCAUGUUUCU |
| A-133957.1 | 95 | asusgsusudTsdTs(5MdC)sdTsdTsdTs(5MdC)sdTsdTsdGscsasasusu | 915 | 191 | AAAUGCAAGAAACAUUUGAUU | 287 | AUGUUUCUUUCUUGCAUU |
| A-133958.1 | 96 | asasasasusdAsdAsdAsdGsdGsdTsdAsdAsdAsuscsasasa | 924 | 192 | AAAGAAAACAUUUGAUUUU | 288 | AAAACAAAAUGUUUUCUUU |
| A-133959.1 | 97 | gsaascsasasdTsdGsdGsdGsdTsdTsdAsdAsdAsuscsasasa | 935 | 193 | UUUGAUUUUAACUCAUUGUC | 289 | GACAAUGAGUUAAAAUCAAA |
| A-133960.1 | 98 | gsaasgsusus(5MdC)sdAsdGsdGsdAsdGsdTsdGsdAs(5MdC)sasasusgsa | 947 | 194 | UCAUUGUCACUCUGAUGUUC | 290 | GAACAUCAGAGUGACAAUGA |
| A-133961.1 | 99 | csasgsusus(5MdC)sdAs(5MdC)sdAsdAsdTsdGsdGsdAs(5MdC)sdAsuscsasgsa | 957 | 195 | UCUGAUGUUCAGUGAACAUG | 291 | CAGUCACAUGAACAUCAGA |
| A-133962.1 | 100 | asgscscscsdGsdAsdAsdGs(5MdC)sdAsdAs(5MdC)s(5MdC)sdAsgsususcsa | 970 | 196 | UGAACUGGCUUGCUUCGGCU | 292 | AGCCCGAAGCAACCAGUUCA |
| A-133963.1 | 101 | csasgsasus(5MdC)sdAsdAsdAsdGsdAsdGs(5MdC)s(5MdC)s(5MdC)sgsasasgsc | 980 | 197 | GCUUCGGCUCUUUGAUCUG | 293 | CAGAUCAAAGAGCCCGAAGC |
| A-133964.1 | 102 | usscscsasusdAsdGsdGsdTsdGsdAs(5MdC)sdAsdGsdAsuscsasasa | 991 | 198 | UUUGAUCUGUCACCUAUGGA | 294 | UCCAUAGGUGACAGAUCAAA |
| A-133965.1 | 103 | ascscsascscsdTs(5MdC)sdAsdAsdTs(5MdC)sdAsdGsdGsdAsdTsdTsdAs(5MdC)s(5MdC)sdAsusasgsgsu | 1002 | 199 | ACCUAUGGAAUCUGAGUGGU | 295 | ACCACUCAGAUUCCAUAGGU |
| A-133966.1 | 104 | asasasasasdAsdTsdAsdAsdAsdAs(5MdC)sdAs(5MdC)sdAs(5MdC)suscsasctsscasaga | 1012 | 200 | UCUGAGUGGUUUUAUUUUU | 296 | AAAAAAUAAAACCACUCAGA |
| A-133967.1 | 105 | csusgsasgsdAsdAsdAsdTs(5MdC)sdTsdAsdAsdAsdAsasasasusasa | 1023 | 201 | UUAUUUUUAGAUUUCCAG | 297 | CUGAGAAAUCUAAAAAUAA |

TABLE 3-continued

Antisense polynucleotides targeting LECT2.

| Oligo | SEQ ID NO: | Modified Antisense Sequence (5' to 3') | Pos | SEQ ID NO: | mRNA Target Sequence | SEQ ID NO: | Unmodified Antisense Sequence |
|---|---|---|---|---|---|---|---|
| A-133968.1 | 106 | usasgsasus(5MdC)sdTsdTsdAsdTsdGsdGsdGsdAs(5MdC)sdTsgsasgsasa | 1036 | 202 | UUCUCAGUCCCAAAGAUCUA | 298 | UAGAUCUUUGGGACUGAGAA |
| A-133969.1 | 107 | ususasususdTsdAsdTs(5MdC)sdTsdTsdAsdGsdAsdTscsusususg | 1046 | 203 | CAAAGAUCUAAGAUAAAUAA | 299 | UUAUUAUCUUAGAUCUUUG |
| A-133970.1 | 108 | gsususcsus(5MdC)sdTsdTsdGsdTsdTsdAsdTsdAsdTsusasuscsu | 1056 | 204 | AGAUAAAUAAACAAGAGAAC | 300 | GUUCUCUUGUUUAUUUAUCU |

TABLE 4

| | Mean % inhibition relative to mock transduced | sd % |
|---|---|---|
| A-133928.1 | 15.31 | 5.73 |
| A-133930.1 | 16.5 | 5.24 |
| A-133931.1 | 17.83 | 2.85 |
| A-133932.1 | 17.98 | 3.05 |
| A-133901.1 | 18.55 | 3.79 |
| A-133933.1 | 19.95 | 6.21 |
| A-133934.1 | 20.18 | 4.28 |
| A-133929.1 | 22.58 | 11.57 |
| A-133902.1 | 23.6 | 2.72 |
| A-133903.1 | 27.68 | 4.2 |
| A-133909.1 | 29 | 13.23 |
| A-133907.1 | 29.45 | 9.49 |
| A-133896.1 | 30.34 | 5.72 |
| A-133899.1 | 30.56 | 2.3 |
| A-133891.1 | 31.51 | 6.9 |
| A-133906.1 | 32.09 | 5.12 |
| A-133895.1 | 32.14 | 10.8 |
| A-133927.1 | 33.65 | 8.46 |
| A-133912.1 | 34.35 | 3.53 |
| A-133882.1 | 35.27 | 3.69 |
| A-133892.1 | 35.44 | 1.11 |
| A-133897.1 | 36.39 | 2.3 |
| A-133925.1 | 37.18 | 10.27 |
| A-133880.1 | 37.43 | 3.74 |
| A-133962.1 | 38.35 | 5.73 |
| A-133946.1 | 38.38 | 12.31 |
| A-133879.1 | 38.76 | 7.22 |
| A-133947.1 | 38.86 | 12.52 |
| A-133905.1 | 38.97 | 3.73 |
| A-133938.1 | 39.54 | 10.71 |
| A-133951.1 | 39.76 | 8.7 |
| A-133900.1 | 40.16 | 8.73 |
| A-133965.1 | 40.35 | 6.63 |
| A-133894.1 | 40.88 | 6.57 |
| A-133926.1 | 41.56 | 3.95 |
| A-133898.1 | 42.14 | 4.02 |
| A-133910.1 | 42.72 | 5.48 |
| A-133940.1 | 42.82 | 11.53 |
| A-133893.1 | 43.33 | 8.19 |
| A-133881.1 | 43.66 | 3.67 |
| A-133884.1 | 44.45 | 9.28 |
| A-133918.1 | 45.11 | 13.42 |
| A-133924.1 | 45.15 | 3.19 |
| A-133911.1 | 45.38 | 13.17 |
| A-133949.1 | 45.51 | 3.91 |
| A-133908.1 | 45.66 | 6.29 |
| A-133921.1 | 47.64 | 11.3 |
| A-133883.1 | 47.75 | 2.72 |
| A-133964.1 | 48.13 | 3.55 |
| A-133948.1 | 48.75 | 13.64 |
| A-133952.1 | 49.2 | 6.98 |
| A-133919.1 | 49.46 | 9.18 |
| A-133922.1 | 50.2 | 8.04 |
| A-133904.1 | 51.11 | 3.64 |
| A-133939.1 | 52.21 | 11.03 |
| A-133960.1 | 52.59 | 8.76 |
| A-133877.1 | 53.67 | 14.22 |
| A-133914.1 | 54.04 | 14.19 |
| A-133888.1 | 54.1 | 2.28 |
| A-133917.1 | 54.86 | 7.77 |
| A-133889.1 | 55.19 | 18.94 |
| A-133963.1 | 55.73 | 14.28 |
| A-133961.1 | 56.33 | 5.71 |
| A-133943.1 | 56.72 | 11.3 |
| A-133937.1 | 57.82 | 8.37 |
| A-133916.1 | 59.71 | 11.95 |
| A-133923.1 | 60.53 | 15.21 |
| A-133935.1 | 62.15 | 14.18 |
| A-133945.1 | 62.37 | 10.27 |
| A-133878.1 | 62.8 | 20.59 |
| A-133876.1 | 62.81 | 29 |
| A-133936.1 | 63.23 | 12.85 |
| A-133953.1 | 63.82 | 9.99 |
| A-133955.1 | 64.82 | 8.41 |
| A-133956.1 | 65.13 | 5.53 |
| A-133942.1 | 66.39 | 12.33 |

TABLE 4-continued

| | Mean % inhibition relative to mock transduced | sd % |
|---|---|---|
| A-133887.1 | 67.61 | 11.09 |
| A-133950.1 | 68.07 | 17.64 |
| A-133954.1 | 70.09 | 7.7 |
| A-133966.1 | 70.84 | 11.12 |
| A-133890.1 | 71.79 | 11.09 |
| A-133957.1 | 72.28 | 13.35 |
| A-133875.1 | 73.95 | 25.21 |
| A-133968.1 | 75.3 | 23.16 |
| A-133915.1 | 76.02 | 24.82 |
| A-133913.1 | 76.42 | 13.21 |
| A-133959.1 | 77.11 | 12.43 |
| A-133920.1 | 84.58 | 5.42 |
| A-133941.1 | 85.16 | 26.35 |
| A-133967.1 | 86.78 | 29.49 |
| A-133970.1 | 92.06 | 22.55 |
| A-133885.1 | 96.21 | 26.94 |
| A-133958.1 | 106.04 | 11.27 |
| A-133944.1 | 111.1 | 16.85 |
| A-133969.1 | 112.27 | 29.54 |
| A-133886.1 | 114.84 | 26.13 |

SEQUENCES

SEQ ID NO: 1
>gi|59806344|ref|NM_002302.2| Homo sapiens
leukocyte cell-derived chemotax 2 (LECT2), mRNA
AAATCAAATAGCTATCCATGGAATATTAGAACTTGACTTGCTCCATCCT
CTTAAACTTTTTGTGTCTCACACTAAAGAAATGAGAGATGCAGAATTCT
AAGGCTAAATAGCTAGGAAGTATTCATTCAAACTTGAATATTCTTCAAA
GAGAGTGTGGGGGCAACTCTAATCAGAGGAAGAAACTAAAGGAAGTAAA
ACCAGATGTTTTCCACCAAAGCCCTCCTTTTGGCTGGTCTGATTTCTAC
CGCACTGGCAGGGCCATGGGCTAATATATGTGCTGGCAAGTCTTCCAAT
GAGATCCGGACGTGTGACCGCCATGGCTGTGGACAGTACTCTGCTCAAA
GAAGTCAGAGGCCTCACCAGGGTGTGGACATCTTGTGCTCTGCTGGATC
TACTGTGTACGCACCATTCACTGGAATGATTGTGGGCCAGGAGAAACCT
TATCAAAACAAGAATGCTATCAATAATGGTGTTCGAATATCTGGAAGAG
GTTTTTGTGTCAAAATGTTCTACATTAAGCCAATTAAGTATAAAGGTCC
TATTAAGAGGGAGAAAAACTTGGAACTCTATTGCCCTTGCAGAAAGTT
TATCCTGGCATACAATCGCATGTGCACATTGAAAACTGTGACTCGAGTG
ACCCTACTGCATACCTGTAAATCGAAGGCCAATGGTCAGATCTTCAAA
TAAAAGTCATCTTAAAAACCTGGATGCATACCCTTCTCTTCAAGAAAT
TTGTGTTCACAAAGGAAAAATGCATGAAGGGATGGATACCCCATTTTCC
ATGACATGATTATTACACATTGCATGCCTGTATCAAAACATCTCACGTA
CCTCATAAACATATACACCTATGTACCCACAAAAATTTTTTAATTAAAA
AAAGGAAATTTGAGTTTAAATAGAAACATGATAAATGCAAGAAAGAAAA
CATTTTGATTTTAACTCATTGTCACTCTGATGTTCATGTGAACTGGTTG
CTTCGGGCTCTTTGATCTGTCACCTATGGAATCTGAGTGGTTTTATTTT
TTAGATTTCTCAGTCCCAAAGATCTAAGATAAATAAACAAGAGAACTT SEQ ID NO: 2
>gi|380692339|ref|NM_001194884.2| Macaca mulatta
leukocyte cell-derived chemotaxin 2 (LECT2), mRNA
TTAGAACTTGACTTGCTCCATACTCTTATATTTTTTGTGTCTCACACTA
AAGAAATGAAAGATGCATGATTCTAAGGCTAAATAGCTAGGAAGTATTC
ATTCAAACTTGAATATTCTTCAAAGAGAGTGTGGGGGCAACTCTAATCG
GAGGAAGAAACATAAAGGAAGTAAACCCAGATGTTTTCCACCAAAGTCC
TCCTTTTGGCTGGTCTGATTTCTACTGCACTGGCAGGGCCATGGGCTAA
TATATGTGCTGGCAAGTCTTCCAACGAGATCCGGACGTGTGACCGCCAT
GGCTGTGGACAGTACTCTGCTCAAAGAAGTCAGAGGCCTCACCAGGGTG
TGGACATCTTGTGCTCTGCTGGATCTACTGTGTATGCACCATTCACTGG
AATGATTGTGGGCCAGGAGAAACCTTATCAAAACAAAAATGCTATCAAT
AATGGTGTTCGAATATCTGGAAGAGGTTTTTGTGTCAAAATGTTCTACA
TTAAGCCAATTAAGTATAAAGGTCCTGTTAAGAGGGAGAAAAACTTGG
AACTCTATTGCCCTTGCAGAAAGTTTATCCTGGCATACAGTCGCACGTG
CACATTGAAAACTGTGACTCGAGTGACCCTACTGCATACCTGTAAATGG
AAGGCCAATGGTCAGATCTTCAAAATAAAAAGTCATCTTAAAAACCTGG
ATGCATACCCCGCTCTTCAAGAAATTTGTATTCACAAAGGAAAATGCA
TGAAGGGATGGATACTCCATTTTCCAGGACTTGGTTATTATACATTGCG
TGCTTGTATCAAAAAAATCTCACGTACCTCATATATGTATACACTTGTGT
ACCCACAAAATTTTTT

SEQUENCES

SEQ ID NO: 3
>gi|255760038|ref|NM_010702.2| Mus musculus
leukocyte cell-derived chemotaxin 2 (Lect2), mRNA
GGATCAGACAGCTCTCCACGGAATGTTACAGTTTAACCCGACTCATCTT
GCTTTCTGTGTCTCTTACTAGATCTCGGAGAGACATAAATTACCAGAGA
AGATTCACTCATTCCGGGGGTGACCCTGTGTGCATGGAGCAGGTCTAAC
TAGAGGAAGAAACAAGAAGCAGAACCTAGATGATTCCCACAACAATCCT
CATTTCAGCTGCTTTGCTTTCCTCTGCCCTAGCAGGACCATGGGCTAAC
ATATGTGCCAGCAAATCTTCCAACGAGATCCGGACGTGTGACAGCTATG
GCTGTGGACAGTACTCTGCTCAAAGAACCCAAAGGCATCACCCAGGTGT
GGACGTCCTGTGCTCGGATGGATCTGTGGTGTATGCACCATTCACTGGG
AAGATAGTGGGCCAGGAGAAACCCTATAGAAACAAAAATGCCATCAATG
ATGGCATTCGACTGTCTGGAAGAGGTTTTTGTGTCAAAATTTTCTACAT
TAAGCCAATTAAGTATAAAGGTTCTATCAAAAAGGGGGAGAAGCTGGGC
ACCTTGCTGCCCCTGCAGAAAGTTTACCCGGGCATCCAGTCGCATGTAC
ACGTTGAAAACTGCGACTCCAGTGACCCCACAGCATACCTGTAAGCAGA
GACAAAGGCCAGATCTTCTAAATTCAAAGCCATCTCAGAAACTGGGACA
TGCCCTGCTCCCGAAGAAACGTGCATTCTAACAGAAACATAAATCTGTG
TAAACACTCACAACCCTGATTCCAAGTCATCACCGCTCTGACGGGTGGG
CTCTGGTCGGCCTGCCACCTCAAGGGCCAGGGAGTTTGACATTTTCGAT
TTTTAGGTTCTGGTGACTGAGATAAATGAATGACCTCTCATGTGAAAAA
AAAAAAA SEQ ID NO: 4
>gi|157817277|ref|NM_001108405.1| Rattus
norvegicus leukocyte cell-derived chemotaxin 2
(Lect2), mRNA
TGACTCATTTTGTTTTCCGTGTCTCGTACTAAACCTCGGAGAAACACGG
GATTCCAAAGCTTAATTACCAGAGAAGGTGGACTCAGTCGTGGACTGTG
TGTGCATGGGAGCAATTCTAACCAGAGGAAGAAACGGGAAGCAGAATCC
AGATGTTTCCCACAAGAATCCTCATGTCAGCTGCTTTGATTTCCACTGC
CCTGGCAGGACCATGGGCTAACATATGTGCCAGCAGATCTTCCAACGAG
ATCCGGACATGTGACAGCTATGGCTGTGGACAGTACTCTACTCAAAGAA
CCCAAAGGCATCATCCAGGTGTGGACGTCCTGTGCTCAGATGGATCTGT
GGTGTATGCGCCATTCACGGGGAAGATAGTGGGCCAGGAGAAACCCTAT
AGAAACAAAAACGCCATCAATGATGGCGTCCGACTGTCGGGAAGAGGTT
TCTGCGTCAAAATTTTCTACATTAAGCCAATTAAGTATAAGGGCTCTAT
CAGAAAGGGAGAGAAGCTGGGCACCTTGCTGCCCCTGCAGAAAGTTTAC
CCTGGCATACAGTCGCATGTACACATTGAAAACTGTGACTCCAGTGATC
CCACGGCATACCTGTAAGCAGAGACAGAGGCCAGATCTTCTCAAATTCC
CAGAAACTGGAACACGTCCTGCTCCTGAAGAAACGTGCATTCTAACAGA
CGTGCCATCAGTGTGGACAATTCTGATTCCGACTCAGCGTCACTCTG
ATGGGCGGGCTCTGATCTGCCTGCTGCCTGGAGGGCCAGGGAGTTTTAT
GTTTCCGATTTTTAAGTTCTGGGGACTGAAATTAAA SEQ ID NO: 5 Reverse Complement of SEQ ID NO: 1
AAGTTCTCTTGTTTATTTATCTTAGATCTTTGGGACTGAGAAATCTAAA
AAATAAAACCACTCAGATTCCATAGGTGACAGATCAAAGAGCCCAGCC
AACCAGTTCACATGAACATCAGAGTGACAATGAGTTAAAATCAAAATGT
TTTCTTTCTTGCATTTATCATGTTTCTATTTAAACTCAAATTTCCTTTT
TTTAATTAAAAAATTTTGTGGGTACATAGGTGTATATGTTTATGAGGT
ACGTGAGATGTTTTGATACAGGCATCAATGTGTACATGACATCATGTCATG
GAAAATGGGGTATCCATCCCTTCATGCATTTTTCCTTTGTGAACACAAA
TTTCTTGAAGAGAAGGGTATGCATCCAGGTTTTTAAGATGACTTTTTAT
TTTGAAGATCTGACCATTGGCCTTCGATTTACAGGTATGCAGTAGGGTC
ACTCGAGTCACAGTTTTCAATGTGCACATGCGATTGTACACACAGATGAA
ACTTTCTGCAAGGGCAATAGAGTTCCAAGTTTTTCTCCCTTCTTAATAG
GACCTTTATACTTAATTGGCTTAATGTAGAACATTTTGACACAAAAACC
TCTTCCAGATATTCGAACACCATTATTGATAGCATTCTTGTTTTGATAA
GGTTTCTCCTGGCCCACAATCATTCCAGTGAATGGTGCGTACACAGTAG
ATCCAGCAGAGCACAAGATGTCCACACCCTGGTGAGGCCTCTGACTTCT
TGAGCAGAGTACTGTCCACAGCCATGGCGGTCACACGTCCGGATCTCA
TTGGAAGACTTGCCAGCACATATATTAGCCCATGGCCCTGCCAGTGCGG
TAGAAATCAGACCAGCCAAAAGGAGGGCTTTGGTGGAAAACATCTGGTT TTACTTCCTTTAGTTTCTTCCTCTGATTAGAGTTGCCCCCACACTCTCT
TTGAAGAATATTCAAGTTTGAATGAATACTTCCTAGCTATTTAGCCTTA
GAATTCTGCATCTCTCATTTCTTTAGTGTGAGACACAAAAAGTTTAAGA
GGATGGAGCAAGTCAAGTTCTAATATTCCATGGATAGCTATTTGATTT SEQ ID NO: 6 Reverse Complement of SEQ ID NO: 2
AAAAAATTTTGTGGGTACACAAGTGTATACATATATGAGGTACGTGAGA
TTTTTTGATACAAGCACGCAATGTATAATAACCAAGTCCTGGAAAATGG
AGTATCCATCCCTTCATGCATTTTTCCTTTGTGAATACAAATTTCTTGA
AGAGCGGGGTATGCATCCAGGTTTTTAAGATGACTTTTTATTTTGAAGA
TCTGACCATTGGCCTTCCATTTACAGGTATGCAGTAGGGTCACTCAAGT
CACAGTTTTCAATGTGCACGTGCGACTGTATGCCAGGATAAACTTTCTG
CAAGGGCAATAGAGTTCCAAGTTTTTCTCCCTTCTTAACAGGACCTTTA
TACTTAATTGGCTTAATGTAGAACATTTTGACACAAAAACCTCTTCCAG
ATATTCGAACACCATTATTGATAGCATTTTGTTTTGATAAGGTTTCTC
CTGGCCCACAATCATTCCAGTGAATGGTGCATACACAGTGATCCAGCA
GAGCACAAGATGTCCACACCCTGGTGAGGCCTCTGACTTCTTTGAGCAG
AGTACTGTCCACAGCCATGGCGGTCACACGTCCGGATCTCGTTGGAAGA
CTTGCCAGCACATATATTAGCCCATGGCCCTGCCAGTGCAGTAGAAATC
AGACCAGCCAAAAGGAGGCTTTGGTGGAAAACATCTGGGTTTTACTTCC
TTTATGTTTCTTCCTCCGATTAGAGTTGCCCCCACACTCTCTTTGAAGA
ATATTCAAGTTTGAATGAATACTTCCTAGCTATTTAGCCTTAGAATCAT
GCATCTTTCATTTCTTTAGTGTGAGACACAAAAAATATAAGAGTATGGA
GCAAGTCAAGTTCTAA SEQ ID NO: 7 Reverse Complement of SEQ ID NO: 3
TTTTTTTTTTTTCACATGAGAGGTCATTCATTTATCTCAGTCACCAGAA
CCTAAAAATCGAAAATGTCAAACTCCCTGGCCCTTGAGGTGGCAGGCCG
ACCAGAGCCCACCCGTCAGAGCGGTGATGACTTGGAATCAGGGTTGTGA
GTGTTTACACAGATTTATGTTTCGTTTAGAATGCACGTTTCTTCGGGAG
CAGGGCATGTCCCAGTTTCTGAGATGGCTTTGAATTTAGAAGATCTGGC
CTTTGTCTGCTTACAGGTATGCTGTGGGGTCACTGGAGTCGCAGTTT
TCAACGTGTACATGCGACTGGATGCCCGGGTAAACTTTCTGCAGGGGCA
GCAAGGTGCCCAGCTTCTCCCCCTTTTTGATAGAACCTTTATACTTAAT
TGGCTTAATGTAGAAAATTTTGACACAAAAACCTCTTCCAGACAGTCGA
ATGCCATCATTGATGGCGTTTTTGTTTCTATAGGGTTTCTCCTGGCCA
CTATCTTCCCAGTGAATGGTGCATACACCACAGATCCATCCGAGCACAG
GACGTCCACACCCTGGGTGATGCCTTTGGGTTCTTTGAGCAGAGTACTGT
CCACAGCCATAGCTGTCACACGTCCGGATCTCGTTGGAAGATTTGCTGG
CACATATGTTAGCCCATGGTCCTGCTAGGGCAGAGGAAAGCAAAGCAGC
TGAAATGAGGATTGTTGTGGGAATCATCTAGGTTCTGCTTCTTGTTTCT
TCCTCTAGTTAGACCTGCTCCATGCACACAGGGTCACCCCCGGAATGAG
TGAATCTTCTCTGGTAATTTATGTCTCTCCGAGATCTAGTAAGAGACAC
AGAAAAGCAAGATGAGTCGGGTTAAACTGTAACATTCCGTGGAGAGCTGT
CTGATCC SEQ ID NO: 8 Reverse Complement of SEQ ID NO: 4
TTTAATTTCAGTCCCCAGAACTTAAAAATCGGAAACATAAAACTCCCTG
GCCCTCCAGGCAGCAGGCAGTAGATCAGAGCCCGCCCATCAGAGTGACGTG
AGTCGGAATCAGAATTGTGTCCACACTGATGGCACGTCGTTAGAATGC
ACGTTTCTTCAGGAGCAGGACGTGTTCCAGTTTCTGGGAATTTGAGAAG
ATCTGGCCTCTGTCTCTGCTTACAGGTATGCCGTGGGATCACTGGAGTC
ACAGTTTTCAATGTGTACATGCGACTGTATGCCAGGGTAAACTTTCTGC
AGGGGCAGCAAGGTGCCCAGCTTCTCTCCCTTTCTGATAGAGCCCTTAT
ACTTAATTGGCTTAATGTAGAAAATTTTGACGCAGAAACCTCTTCCCGA
CAGTCGGACGCCATCATTGATGGCGTTTTTGTTTCTATAGGGTTTCTCC
TGGCCCACTATCTTCCCCGTGAATGGCGCATACACCACAGATCCATCTG
AGCACAGGACGTCCACACCTGGATGATGCCTTTGGGTTCTTTGAGTAGA
GTACTGTCCACAGCCATAGCTGTCACATGTCCGGATCTCGTTGGAAGAT
CTGCTGGCACATATGTTAGCCCATGGTCCTGCCAGGGCAGTGGAAATCA
AAGCAGCTGCATGAGGATTCTTGTGGGAAACATCTGGATTCTGCTTCC
CGTTTCTTCCTCTGGTTAGAATTGCTCCCATGCACACACAGTCCACGAC
TGAGTCCACCTTCTCTGGTAATTAAGCTTTGGAATCCCGTGTTTCTCCG
AGGTTTAGTACGAGACACGGAAAACAAAATGAGTCA

I claim:

1. A single-stranded antisense polynucleotide agent for inhibiting expression of LECT2, wherein the agent comprises at least 8 contiguous nucleotides differing by no more than 3 nucleotides from the sequence of GCACAUGC-GAUUGUAUGCCA (SEQ ID NO: 258), and wherein at least one of the contiguous nucleotides is a modified nucleotide.

2. The agent of claim 1, which is 10 to 40 nucleotides in length.

3. The agent of claim 1, wherein the modified nucleotide comprises a modified sugar moiety selected from the group consisting of: a 2'-O-methoxyethyl modified sugar moiety, a 2'-methoxy modified sugar moiety, a 2'-O-alkyl modified sugar moiety, and a bicyclic sugar moiety.

4. The agent of claim 1, wherein the agent is a gapmer comprising a gap segment comprised of linked 2'-deoxynucleotides positioned between a 5' and a 3' wing segment.

5. The agent of claim 4, wherein the 5'-wing segment is 1, 2, 3, 4, 5, or 6 nucleotides in length.

6. The agent of claim 4, wherein the 3'-wing segment is 1, 2, 3, 4, 5, or 6 nucleotides in length.

7. The agent of claim 4, wherein the gap segment is 5, 6, 7, 8, 9, 10, 11, 12, 13, or 14 nucleotides in length.

8. The agent of claim 1, wherein the agent further comprises a ligand.

9. The agent of claim 8, wherein the agent is conjugated to the ligand at the 3'-terminus, wherein the ligand is an N-acetylgalactosamine (GalNAc) derivative.

10. The agent of claim 9, wherein the ligand is

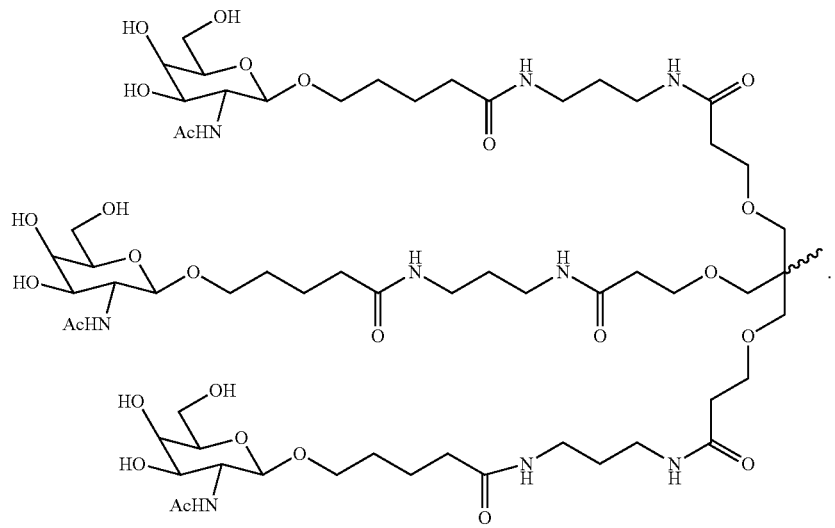 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

11. A pharmaceutical composition for inhibiting expression of a LECT2 gene comprising the agent of claim 1.

12. A pharmaceutical composition comprising the agent of claim 1, and a lipid formulation, wherein the lipid formulation comprises an LNP or an MC3.

13. A method of inhibiting LECT2 expression in a cell, the method comprising:
(a) contacting the cell with the agent of claim 1; and
(b) maintaining the cell produced in step (a) for a time sufficient to obtain antisense inhibition of a LECT2 gene, thereby inhibiting expression of the LECT2 gene in the cell.

14. The agent of claim 1, which is 10 to 30 nucleotides in length.

15. The agent of claim 1, which is 18 to 30 nucleotides in length.

16. The agent of claim 1, which is 10 to 24 nucleotides in length.

17. The agent of claim 1, which is 18 to 24 nucleotides in length.

18. The agent of claim 1, which is 14 or 20 nucleotides in length.

19. The agent of claim 1, wherein the modified nucleotide is a 5-methylcytosine.

20. The agent of claim 1, wherein the modified nucleotide comprises a modified internucleoside linkage.

21. The agent of claim 1, which comprises a plurality of 2'-deoxynucleotides flanked on each side by at least one nucleotide having a modified sugar moiety.

22. The agent of claim 21, wherein the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

23. The agent of claim 1, wherein the agent comprises at least 12 contiguous nucleotides differing by no more than 3 nucleotides from the sequence of GCACAUGCGAUUGUAUGCCA (SEQ ID NO: 258).

24. The agent of claim 1, wherein the agent comprises at least 11 contiguous nucleotides of the sequence of GCACAUGCGAUUGUAUGCCA (SEQ ID NO: 258).

25. The agent of claim 1, wherein the agent comprises the sequence of GCACAUGCGAUUGUAUGCCA (SEQ ID NO: 258).

26. The agent of claim 1, wherein the agent comprises the sequence and modifications of gscsascsasdTsdGs(5MdC)sdGsdAsdTsdTsdGsdTsdAsusgscscsa (SEQ ID NO: 66).

27. The agent of claim 1, wherein the agent consists of the sequence of GCACAUGCGAUUGUAUGCCA (SEQ ID NO: 258).

28. The agent of claim 1, wherein the agent consists of the sequence and modifications of gscsascsasdTsdGs(5MdC)sdGsdAsdTsdTsdGsdTsdAsusgscscsa (SEQ ID NO: 66).

* * * * *